United States Patent
Svendsen et al.

(10) Patent No.: US 6,890,902 B2
(45) Date of Patent: May 10, 2005

(54) CYTOTOXIC MODIFIED LACTOFERRIN PEPTIDES

(75) Inventors: John Sigurd Svendsen, Tromso (NO); Oystein Rekdal, Tromso (NO); Baldur Sveinbjornsson, Tromso (NO); Lars Vorland, Tromso (NO)

(73) Assignee: Alpharma AS, Oslo (NO)

( * ) Notice: Subject to any disclaimer, the term of this patent is extended or adjusted under 35 U.S.C. 154(b) by 274 days.

(21) Appl. No.: 09/798,869

(22) Filed: Feb. 27, 2001

(65) Prior Publication Data

US 2003/0022821 A1 Jan. 30, 2003

Related U.S. Application Data

(63) Continuation of application No. PCT/GB99/02851, filed on Aug. 31, 1999.

(30) Foreign Application Priority Data

Aug. 28, 1998 (GB) .............................................. 9818938

(51) Int. Cl.[7] ....................... A61K 38/03; A61K 38/40; C07K 7/00; C07K 14/00; C07K 14/79
(52) U.S. Cl. ............................. 514/11; 514/12; 514/13; 514/14; 514/15; 514/16; 514/21; 530/317; 530/324; 530/325; 530/326; 530/327; 530/328; 530/329; 530/345
(58) Field of Search ................................ 514/11, 12, 13, 514/14, 15, 16, 21; 530/317, 321, 324, 325, 326, 327, 328, 329, 345

(56) References Cited

U.S. PATENT DOCUMENTS

| | | | |
|---|---|---|---|
| 5,073,542 A | | 12/1991 | Zasloff .......................... 514/12 |
| 5,141,851 A | * | 8/1992 | Brown et al. .................. 435/15 |
| 5,304,633 A | * | 4/1994 | Tomita et al. ............... 530/326 |
| 5,411,942 A | * | 5/1995 | Widmer et al. ................ 514/17 |
| 5,428,016 A | * | 6/1995 | Tomita et al. ................ 514/15 |
| 5,565,425 A | * | 10/1996 | Yamamoto et al. ........... 514/12 |
| 5,593,866 A | | 1/1997 | Hancock et al. ........... 435/69.7 |
| 2003/0148936 A1 | | 8/2003 | Svendsen et al. ............. 514/12 |

FOREIGN PATENT DOCUMENTS

| | | |
|---|---|---|
| EP | 0 629 347 B1 | 7/1997 |
| WO | WO92/22317 | 12/1992 |
| WO | WO93/24138 | 12/1993 |
| WO | WO94/12206 | 6/1994 |
| WO | WO94/01451 | 1/1995 |
| WO | WO96/40768 | 12/1996 |
| WO | WO96/40770 | 12/1996 |
| WO | WO98/06425 | 2/1998 |
| WO | WO98/06860 | 2/1998 |
| WO | WO98/40091 | 9/1998 |
| WO | WO98/40401 | 9/1998 |

OTHER PUBLICATIONS

Yoo et al. Bovine Lactoferrin and Lactoferricin, a Peptide Derived from ... Japanese Journal of Cancer Research. Feb. 1997, vol. 88, pp. 184–190.*

Chapple et al. Structure–Function Relationship of Antibacterial Synthetic Peptides ... Infection And Immunity. Jun. 1998, vol. 66, No. 6, pp. 2434–2440.*

(Continued)

Primary Examiner—Jeffrey Edwin Russel
(74) Attorney, Agent, or Firm—Dorsey & Whitney LLP

(57) ABSTRACT

The present invention provides a modified lactoferrin peptide which is cytotoxic, 7 to 25 amino acids in length, with three or more cationic residues and which has one or more extra bulky and lipophilic amino acids as compared to the native lactoferrin sequence, as well as esters, amides, salts and cyclic derivatives thereof as well as methods of preparing such peptides, pharmaceutical compositions containing such peptides and use of the peptides as medicaments, particularly as antibacterials or anti-tumoural agents.

21 Claims, 10 Drawing Sheets

OTHER PUBLICATIONS

Kang et al. Structure–biological activity relationships of 11–residue highly basic peptide segment of bovine lactoferrin. International Journal Of Peptide and Protein Research. Oct. 1996, vol. 38, No. 4, pp. 357–363.*
European Patent Application Publication No. 0 510 912 A1m Oct. 28, 1992.
European Patent Application Publication No. 0 299 828 A1, Jan. 18, 1989.
Andreu et al. (1985) Biochemistry 24:1683–1688.
Bellamy et al. (1992) Journal of Applied Bacteriology 73:472–479.
Bellamy et al. (1992) Biochimica et Biophysica Acta 1121:130–136.
Bessalle et al. (1993) J. Med. Chem. 36:1203–1209.
Blondelle et al. (1992) Biochemistry 31:12688–12694.
Boman (1995) Ann. Rev. Immunol. 13:61–92.
Chen et al. (1988) FEB 236:462–466.
Cruciani et al. (1991) Proc. Natl Acad. Sci. USA 88:3792–3796.
Hancock et al. (1995) Advances in Microbial Physiol. 37:135–175.
Juretic et al. (1989) FEB 249:219–223.
Ludtke et al. (1996) Biochemistry 35:13723–13728.
Ranjalahy–Rasoloarijao et al. (1989) Int. J. Peptide Protein Res. 33:273–280.
Selsted et al. (1992) J. Biol. Chem. 267:4292–4295.
Stierandova et al. (1994) Int. J. Peptide Protein Res. 43:31–38.
Tomita et al. (1991) J. Fairy Sci. 74:4137–4142.
Vorland et al. (1999) APMIS. 107:971–981.
Wieprecht et al. (1997) FEBS Letters 417:135–140.
Zasloff et al. (1988) Proc. Natl. Acad. Sci. USA 85:910–913.

* cited by examiner

Table 1: Amino acid sequence and charge at pH7 for synthetic lactoferricins from different species

| Species | Sequence | | Name | Charge at pH7 |
|---|---|---|---|---|
| Human | TKCFQWQRNMRKVRGPPVSCIKRDS | (SEQ ID NO:20) | LFH(18-42) | 5.85 |
| Bovine | FKCRRWQWRMKKLGAPSITCVRRAF | (SEQ ID NO:21) | LFB(17-41) | 7.84 |
| Murine | EKCLRWQNEMRKVGGPPLSCVKKSS | (SEQ ID NO:22) | LFM(17-41) | 3.85 |
| Caprine | SKCYQWQRRMRKLGAPSITCVRRTS | (SEQ ID NO:23) | LFC(17-41) | 6.85 |
| Bovine | PEWFKCRRWQWRMKKLGA | (SEQ ID NO:24) | LFB(14-31) | 6.85 |
| Bovine | FKCRRWQWRMKKLGA | (SEQ ID NO:1) | LFB(17-31) | 5.88 |
| Bovine | KCRRWQWRMKKLGA | (SEQ ID NO:25) | LFB(18-31) | 5.88 |
| Bovine | CRRWQWRMKKLGA | (SEQ ID NO:26) | LFB(19-31) | 4.88 |
| Bovine | RRWQWRMKKLGA | (SEQ ID NO:27) | LFB(20-31) | 4.91 |
| Bovine | KKCRRWQWRMKKLGA | (SEQ ID NO:28) | LFB(17-31)K17 | 6.87 |
| Bovine | FKCFRWQWRMKKLGA | (SEQ ID NO:29) | LFB(17-31)F20 | 5.87 |
| Bovine | KKCFRWQWRMKKLGA | (SEQ ID NO:30) | LFB(17-31)K17,F20 | 4.88 |

| Secondary Structure | ←——— Helix ———→ ←⟨Turn⟩→ ←——— Sheet ———→ |

Figure 1

SEQUENCE LISTING

<160> NUMBER OF SEQ ID NOS: 30

<210> SEQ ID NO 1
<211> LENGTH: 15
<212> TYPE: PRT
<213> ORGANISM: BOVINE

<400> SEQUENCE: 1

Phe Lys Cys Arg Arg Trp Gln Trp Arg Met Lys Lys Leu Gly Ala
1               5                   10                  15

<210> SEQ ID NO 2
<211> LENGTH: 15
<212> TYPE: PRT
<213> ORGANISM: HOMO SAPIENS

<400> SEQUENCE: 2

Thr Lys Cys Phe Gln Trp Gln Arg Asn Met Arg Lys Val Arg Gly
1               5                   10                  15

<210> SEQ ID NO 3

```
<211> LENGTH: 15
<212> TYPE: PRT
<213> ORGANISM: CAPRINE

<400> SEQUENCE: 3

Ser Lys Cys Tyr Gln Trp Gln Arg Arg Met Arg Lys Leu Gly Ala
 1               5                  10                  15

<210> SEQ ID NO 4
<211> LENGTH: 15
<212> TYPE: PRT
<213> ORGANISM: MURINE

<400> SEQUENCE: 4

Glu Lys Cys Leu Arg Trp Gln Asn Glu Met Arg Lys Val Gly Gly
 1               5                  10                  15

<210> SEQ ID NO 5
<211> LENGTH: 15
<212> TYPE: PRT
<213> ORGANISM: PIG

<400> SEQUENCE: 5

Ser Lys Cys Arg Gln Trp Gln Ser Lys Ile Arg Arg Thr Asn Pro
 1               5                  10                  15

<210> SEQ ID NO 6
<211> LENGTH: 15
<212> TYPE: PRT
<213> ORGANISM: Artificial Sequence
<220> FEATURE:
<223> OTHER INFORMATION: SYNTHETIC PEPTIDE (modified form of Homo
      sapiens sequence)

<400> SEQUENCE: 6

Thr Lys Cys Phe Gln Trp Gln Trp Asn Met Arg Lys Val Arg Gly
 1               5                  10                  15

<210> SEQ ID NO 7
<211> LENGTH: 15
<212> TYPE: PRT
<213> ORGANISM: Artificial Sequence
<220> FEATURE:
<223> OTHER INFORMATION: synthetic peptide (modified form of homo
      sapiens sequence)

<400> SEQUENCE: 7

Ser Lys Cys Tyr Gln Trp Gln Trp Arg Met Arg Lys Leu Gly Ala
 1               5                  10                  15

<210> SEQ ID NO 8
<211> LENGTH: 15
<212> TYPE: PRT
<213> ORGANISM: Artificial Sequence
<220> FEATURE:
<223> OTHER INFORMATION: SYNTHETIC PEPTIDE (modified form of caprine
      sequence)

<400> SEQUENCE: 8

Glu Lys Cys Leu Arg Trp Gln Trp Glu Met Arg Lys Val Gly Gly
 1               5                  10                  15

<210> SEQ ID NO 9
<211> LENGTH: 15
<212> TYPE: PRT
<213> ORGANISM: Artificial Sequence
<220> FEATURE:
```

-continued

<223> OTHER INFORMATION: SYNTHETIC PEPTIDE (modified form of bovine
      sequence)

<400> SEQUENCE: 9

Phe Lys Trp Arg Arg Trp Gln Trp Arg Met Lys Lys Leu Gly Ala
 1               5                  10                  15

<210> SEQ ID NO 10
<211> LENGTH: 15
<212> TYPE: PRT
<213> ORGANISM: Artificial Sequence
<220> FEATURE:
<223> OTHER INFORMATION: SYNTHETIC PEPTIDE (modified form of bovine
      sequence)

<400> SEQUENCE: 10

Phe Lys Cys Arg Arg Trp Gln Trp Arg Met Lys Lys Leu Trp Ala
 1               5                  10                  15

<210> SEQ ID NO 11
<211> LENGTH: 15
<212> TYPE: PRT
<213> ORGANISM: Artificial Sequence
<220> FEATURE:
<223> OTHER INFORMATION: SYNTHETIC PEPTIDE (modified form of bovine
      sequence)

<400> SEQUENCE: 11

Phe Lys Trp Arg Arg Trp Gln Trp Arg Met Lys Lys Leu Trp Ala
 1               5                  10                  15

<210> SEQ ID NO 12
<211> LENGTH: 15
<212> TYPE: PRT
<213> ORGANISM: Artificial Sequence
<220> FEATURE:
<223> OTHER INFORMATION: SYNTHETIC PEPTIDE (modified form of bovine
      sequence)

<400> SEQUENCE: 12

Phe Lys Trp Arg Arg Trp Trp Trp Arg Met Lys Lys Leu Trp Ala
 1               5                  10                  15

<210> SEQ ID NO 13
<211> LENGTH: 15
<212> TYPE: PRT
<213> ORGANISM: Artificial Sequence
<220> FEATURE:
<223> OTHER INFORMATION: SYNTHETIC PEPTIDE (modified form of bovine
      sequence)

<400> SEQUENCE: 13

Phe Lys Cys Trp Arg Trp Gln Trp Arg Trp Lys Lys Leu Gly Ala
 1               5                  10                  15

<210> SEQ ID NO 14
<211> LENGTH: 11
<212> TYPE: PRT
<213> ORGANISM: Artificial Sequence
<220> FEATURE:
<223> OTHER INFORMATION: SYNTHETIC PEPTIDE

<400> SEQUENCE: 14

Tyr Arg Ala Trp Arg Trp Ala Trp Arg Trp Arg
 1               5                  10

<210> SEQ ID NO 15

```
<211> LENGTH: 11
<212> TYPE: PRT
<213> ORGANISM: Artificial Sequence
<220> FEATURE:
<221> NAME/KEY: D-amino acid
<223> OTHER INFORMATION: SYNTHETIC PEPTIDE
<220> FEATURE:
<223> OTHER INFORMATION: Xaa is D-amino acid

<400> SEQUENCE: 15

Xaa Arg Xaa Trp Xaa Trp Xaa Trp Xaa Trp Xaa
 1               5                  10

<210> SEQ ID NO 16
<211> LENGTH: 11
<212> TYPE: PRT
<213> ORGANISM: Artificial Sequence
<220> FEATURE:
<221> NAME/KEY: D-amino acid
<223> OTHER INFORMATION: SYNTHETIC PEPTIDE
<220> FEATURE:
<223> OTHER INFORMATION: Xaa is D-amino acid

<400> SEQUENCE: 16

Xaa Xaa Xaa Trp Arg Trp Xaa Trp Arg Trp Arg
 1               5                  10

<210> SEQ ID NO 17
<211> LENGTH: 7
<212> TYPE: PRT
<213> ORGANISM: Artificial Sequence
<220> FEATURE:
<223> OTHER INFORMATION: SYNTHETIC PEPTIDE

<400> SEQUENCE: 17

Arg Trp Trp Arg Tyr Trp Arg
 1               5

<210> SEQ ID NO 18
<211> LENGTH: 7
<212> TYPE: PRT
<213> ORGANISM: Artificial Sequence
<220> FEATURE:
<221> NAME/KEY: D-amino acid
<223> OTHER INFORMATION: SYNTHETIC PEPTIDE
<220> FEATURE:
<223> OTHER INFORMATION: Xaa is D-amino acid

<400> SEQUENCE: 18

Xaa Trp Xaa Arg Xaa Trp Xaa
 1               5

<210> SEQ ID NO 19
<211> LENGTH: 7
<212> TYPE: PRT
<213> ORGANISM: Artificial Sequence
<220> FEATURE:
<221> NAME/KEY: D-amino acid
<223> OTHER INFORMATION: SYNTHETIC PEPTIDE
<220> FEATURE:
<223> OTHER INFORMATION: Xaa is D-amino acid

<400> SEQUENCE: 19

Xaa Xaa Trp Arg Tyr Xaa Xaa
 1               5

<210> SEQ ID NO 20
<211> LENGTH: 25
<212> TYPE: PRT
```

```
<213> ORGANISM: Homo Sapiens

<400> SEQUENCE: 20

Thr Lys Cys Phe Gln Trp Gln Arg Asn Met Arg Lys Val Arg Gly Pro
 1               5                  10                  15

Pro Val Ser Cys Ile Lys Arg Asp Ser
            20                  25

<210> SEQ ID NO 21
<211> LENGTH: 25
<212> TYPE: PRT
<213> ORGANISM: BOVINE

<400> SEQUENCE: 21

Phe Lys Cys Arg Arg Trp Gln Trp Arg Met Lys Lys Leu Gly Ala Pro
 1               5                  10                  15

Ser Ile Thr Cys Val Arg Arg Ala Phe
            20                  25

<210> SEQ ID NO 22
<211> LENGTH: 25
<212> TYPE: PRT
<213> ORGANISM: MURINE

<400> SEQUENCE: 22

Glu Lys Cys Leu Arg Trp Gln Asn Glu Met Arg Lys Val Gly Gly Pro
 1               5                  10                  15

Pro Leu Ser Cys Val Lys Lys Ser Ser
            20                  25

<210> SEQ ID NO 23
<211> LENGTH: 25
<212> TYPE: PRT
<213> ORGANISM: CAPRINE

<400> SEQUENCE: 23

Ser Lys Cys Tyr Gln Trp Gln Arg Arg Met Arg Lys Leu Gly Ala Pro
 1               5                  10                  15

Ser Ile Thr Cys Val Arg Arg Thr Ser
            20                  25

<210> SEQ ID NO 24
<211> LENGTH: 18
<212> TYPE: PRT
<213> ORGANISM: BOVINE

<400> SEQUENCE: 24

Pro Glu Trp Phe Lys Cys Arg Arg Trp Gln Trp Arg Met Lys Lys Leu
 1               5                  10                  15

Gly Ala

<210> SEQ ID NO 25
<211> LENGTH: 14
<212> TYPE: PRT
<213> ORGANISM: BOVINE

<400> SEQUENCE: 25

Lys Cys Arg Arg Trp Gln Trp Arg Met Lys Lys Leu Gly Ala
 1               5                  10

<210> SEQ ID NO 26
<211> LENGTH: 13
```

```
<212> TYPE: PRT
<213> ORGANISM: BOVINE

<400> SEQUENCE: 26

Cys Arg Arg Trp Gln Trp Arg Met Lys Lys Leu Gly Ala
 1               5                  10

<210> SEQ ID NO 27
<211> LENGTH: 12
<212> TYPE: PRT
<213> ORGANISM: BOVINE

<400> SEQUENCE: 27

Arg Arg Trp Gln Trp Arg Met Lys Lys Leu Gly Ala
 1               5                  10

<210> SEQ ID NO 28
<211> LENGTH: 15
<212> TYPE: PRT
<213> ORGANISM: BOVINE

<400> SEQUENCE: 28

Lys Lys Cys Arg Arg Trp Gln Trp Arg Met Lys Lys Leu Gly Ala
 1               5                  10                  15

<210> SEQ ID NO 29
<211> LENGTH: 15
<212> TYPE: PRT
<213> ORGANISM: BOVINE

<400> SEQUENCE: 29

Phe Lys Cys Phe Arg Trp Gln Trp Arg Met Lys Lys Leu Gly Ala
 1               5                  10                  15

<210> SEQ ID NO 30
<211> LENGTH: 15
<212> TYPE: PRT
<213> ORGANISM: BOVINE

<400> SEQUENCE: 30

Lys Lys Cys Phe Arg Trp Gln Trp Arg Met Lys Lys Leu Gly Ala
 1               5                  10                  15
```

CYTOTOXIC MODIFIED LACTOFERRIN PEPTIDES

This is a continuation of copending international application Ser. No. PCT/GB9902851 filed Aug. 31, 1999, which application was published by the International Bureau in English on Mar. 9, 2000.

The present invention relates to bioactive peptides, more particularly to peptides which have been modified to enhance their cytotoxic activity.

A wide variety of organisms use peptides as part of their host defense mechanism, in vertebrates this supplements the highly specific cell-mediated immune system [Mor, a., Hani, K. and Nicolas, P. (1994) J. Biol. Chem. 269, 31635–31641. Boman, H. G. (1996) Scand. J. Immunol. 43, 475–482]. Antimicrobial peptides have been isolated from species as diverse as bacteria and mammals [Lehrer, R. I., Lichtenstein, A. K. and Ganz, T. (1993) Ann. Rev. Immunol. 11, 105–128] Generally, these antibiotic peptides have a net positive charge and a propensity to form amphiphilic α-helix or β-sheet structures upon interaction with the outer phospholipid bilayer in bacterial cell membranes [Besalle, R., Gorea, A., Shalit, J., Metger, J. W., Dass, C. Desiderio, D. M. and Fridkin, M. (1993) J. Med. Chem. 36 1203–1209]. In most cases the detailed molecular mechanisms of the antibiotic action are unknown, although some peptides categorised as class L (lytic) peptides are believed to interact with bacterial cell membranes, probably forming ion-channels or pores [Ludtke, S. J., He, K., Heller, W. T., Harroun, T. A., Yang, L. and Huang, H. W. (1996) Biochemistry 35 13723–13728] leading to permeability changes and consequent cell lysis.

Magainins are antibacterial peptides from the skin of the frog *Xenopus laeris* and are classified as class L antibiotics because they specifically lyse bacteria; other peptides such as mastroparans, a bee venom, lack this specificity as they lyse eukaryotic as well as prokaryotic cells and are called Class L Venoms [Tytler, E. M., Anantharamaiah, G. M., Walker, D. E., Mishra, V. K., Palgunachari, M. N. and Segrest, J. P. (1995) Biochemistry 34 4393–4401]. Antibiotic resistance exhibited by certain infectious microorganisms is an increasing problems and there is always a need for new antibiotics. Anti-bacterial peptides such as the class L peptides are known and more are being discovered, with the aim of finding a peptide which is highly cytotoxic and preferably specific for prokaryotic cells. There are differences in the structure and composition of lipid bi-layers between eukaryotes and prokaryotes and amongst prokaryotes themselves which mean that different peptides will have widely differing specificities.

As well as magainins and mastroparans, host defense peptides have been isolated from moths and flies (cecropins) and from Horseshoe crab. The direct action of these host defense peptides to repel predators, for example as venoms, is clear. The search for peptides which exhibit antibiotic effects has lead to the identification of other proteins/peptides which would not be expected to have cytotoxic properties. One of these is lactoferrin, an iron transporter which also shows a weak antibacterial effect.

As well as searching for new antimicrobial peptides, more recently it has been sought to enhance the activity of proteins or peptides with known antimicrobial properties. This has been done in the case of bovine lactoferrin by digesting the native protein with gastric pepsin to produce a peptide, lactoferricin B (LFB), which is much more active than the native bovine lactoferrin. LFB is a 25 residue peptide which corresponds to residues 17–41 of bovine lactoferrin. [Bellamy et al. (1992) Biochem. Biophys. Acta. 1121 pp 130 et seq.]. Structure-activity studies have been carried out on magainins and it has been shown, for example, that enhancement of helicity and of the cationic charge leads to higher antibacterial activity [Chen, Y. H., Brown, J. H., Morell, J. L. and Huang, C. M. (1988) FEBS Letters 236, 462–466]. However, such sequence modifications often result in higher hemolytic activity. It is thus an object of the present invention to prepare peptides and/or peptide derivatives which have significant antibacterial activity but preferably have low toxicity, i.e. little effect on normal eukaryotic cells, e.g. low hemolytic activity. While red blood cells may not be typical eukaryotic cells, they provide a convenient way of assaying for toxicity and in any event are a type of cell which should not be lysed to a significant extent by therapeutic bioactive peptides.

It has been found that by increasing the bulk or lipophilic nature of a peptide derived from lactoferrin, its bioactivity can be increased, in particular its cytotoxicity. Preferably, the bulk and lipophilicity of one or more amino acid residues is increased.

Thus, according to the present invention is provided a modified lactoferrin peptide which is cytotoxic, 7 to 25 amino acids in length, with three or more cationic residues which is optionally capable of forming an amphiphatic a-helix and which has one or more extra bulky and lipophilic amino acids as compared to the native lactoferrin sequence, as well as esters, amides, salts and cyclic derivatives thereof.

By "a modified lactoferrin peptide" is meant a peptide which is based on lactoferrin or, more particularly, on a fragment thereof. Lactoferrin has been identified in a large number of organisms and this invention relates to modifications of lactoferrin and fragments thereof from all species. In particular, the invention relates to modified fragments of lactoferrin derived from mammals, especially modified fragments of bovine, murine, human, porcine and caprine lactoferrin.

LFB has been found to be more antimicrobially active than bovine lactoferrin itself and the peptides of the invention will preferably be modified LFB or fragments thereof or the equivalent region to LFB in lactoferrin from other species.

The incorporation of an extra bulky and lipophilic amino acid into a lactoferrin derived peptide is considered to be a modification according to the invention.

The peptide will have 60% or more, preferably 70% or even 80% homology with the corresponding fragment of naturally occurring lactoferrin, e.g. of LFB or a fragment thereof.

For the purposes of the present invention, the term "sequence homology" is not used to refer to sequence identity but to the presence of either the same amino acid or one from the same functional group. The standard genetically coded amino acids can be grouped according to their characteristics, particularly of polarity and charge. Convenient groupings are, glycine and alanine, serine, threonine, asparagine, glutamine and cysteine, lysine, arginine and histidine, aspartic acid and glutamic acid and valine, leucine, isoleucine, methionine, phenylalanine, tryptophan and tyrosine.

Of the 20 standard genetically coded amino acids, valine, leucine, isoleucine, methionine, tyrosine, tryptophan and phenylalanine are intended to be covered by the term "bulky and lipophilic amino acid", isoleucine, tyrosine, tryptophan and phenylalanine being preferred. In certain circumstances therefore, because even within this group of bulky/lipophilic amino acids there is a gradual increase in the degree of bulkiness/lipophilicity, an enhanced effect may be caused by replacing one of the less bulky/lipophilic residues e.g. valine by one of the more bulky/lipophilic residues such as tyrosine or tryptophan. These amino acids are conveniently referred to herein as "genetic" amino acids and can be contrasted with a second group of amino acids which are "non-genetic", i.e. which may be naturally occurring but are not coded for by the 3 letter genetic code.

Throughout this specification, the widely used and understood three letter and one letter code for the 20 standard amino acids has been used. Replacement of an amino acid from one group with another amino acid in the same group is conveniently referred to as a "conservative substitution". Such substitutions do not generally materially effect the properties of the peptides of the invention and where any peptide differs from another only by such substitutions, if one peptide is a peptide according to the present invention then typically the other peptide will also be a peptide according to the invention.

"Non-genetic" bulky and lipophilic amino acids include naturally occurring and synthetic amino acids having a bulky and lipophilic character as well as genetic and non-genetic amino acids whose bulkiness and/or lipophilicity have been enhanced by chemical modification. A wide variety of amino acids and amino acid derivatives having a bulky and lipophilic character are known to the skilled man and are intended to be included within the term "bulky and lipophilic amino acid".

The "extra" amino acid may refer to the addition or substitution of a standard (genetic) bulky and lipophilic amino acid not present in the native peptide, to an amino acid present in the native peptide which has been modified to make it more bulky and lipophilic or to the addition or substitution of a non-genetic amino acid. When the extra amino acid is 'added', then all original amino acids in the peptide remain. When the extra amino acid is "substituted", it replaces one of the naturally occurring amino acids. The bulky and/or lipophilic amino acids are preferably present in place of other, naturally occurring, non-essential amino acids. By "non-essential" is meant an amino acid whose presence is not required for the peptide as a whole to demonstrate cytotoxic activity.

The different amino acids and their derivatives which fall within the definition of "bulky and lipophilic" amino acid may conveniently be grouped into three categories. The first group are those whose R group (a side chain), lends the amino acid a bulky and lipophilic character. The group of 'genetic' amino acids in this category has been defined earlier, for example, tryptophan has an indole R group and is considered a bulky and lipophilic amino acid. It has recently been found that one of the standard protecting groups for arginine, PMC (2,2,5,7,8-penta-methylchroman-6-sulphonyl) can, under certain conditions, be transferred to tryptophan, resulting in sulphonation of the R group of tryptophan. Peptides wherein one or more tryptophan residues have been modified in this way have surprising been shown to have greatly enhanced cytotoxic activity. PMC modified tryptophan is thus a further example of an R group type bulky and lipophilic amino acid.

It has surprisingly been found that amino acids or their derivatives which have R groups of a certain size can be used to provide modified peptides which are particularly suitable for use as cytotoxic peptides. Thus, according to a preferred aspect of the invention, the extra "bulky and lipophilic amino acid" is any amino acid or amino acid derivative, whose R group is uncharged and has at least 3, preferably 4 or more, e.g. 7 or 8, more preferably at least 9 non-hydrogen atoms. Particularly preferred non-genetic bulky and lipophilic amino acids will have at least 12, preferably at least 18 non-hydrogen atoms in the R group. By way of example, the R group of the amino acid phenylalanine has 7 non-hydrogen atoms and thus falls within our definition of "bulky and lipophilic amino acids".

Preferably, for 'non-genetic' amino acids, the R group in the extra bulky and lipophilic amino acid will have at least 8 or 9 non-hydrogen e.g. carbon atoms, more preferably it should have at least 2 closed rings of 5 or 6 atoms and conveniently these two rings are fused or bridged. The group may comprise only one ring which is substituted by heavily branched alkyl groups, i.e. by groups which include more than 1 branch site or 1 branch site which has attachments to 4 non-hydrogen atoms. The rings are formed of carbon atoms, optionally also including nitrogen, oxygen or sulphur atoms. Particularly preferred amino acids comprise a substituted or unsubstituted indole. The group should preferably be three-dimensional. Preferred non-genetic bulky and lipophilic amino acids include adamantylalanine, 3-benzothienylalanine, 4,4'-biphenylalanine, 3,3-diphenylalanine, homophenylalanine, 2,6-dichlorobenzyltyrosine, Cyclohexyltyrosine, 7-Benzyloxytryptophan, tri-tert-butyltryptophan, Homotryptophan, 3-(-Anthracenyl)-L-alanine, L-p-isopropylphenylalanine, L-Thyroxine, 3,3',5-Triiodo-L-thyronine.

Suitable bulky and lipophilic amino acid residues will therefore include naturally occurring and non-naturally occurring amino acids which have an R group as previously defined, e.g. tryptophan or adamantylalanine or any amino acid, including genetically coded amino acids, whose R groups have been modified to provide a bulky and lipophilic amino acid.

Bulky and lipophilic amino acids in this second category include modified tryptophan and phenylalanine residues, in particular tryptophan residues which have been substituted at the 1-, 2-, 5- and/or 7-position of the indole ring, positions 1- or 2-being preferred.

A variety of other non-genetically coded and synthetic amino acids and their derivatives having a bulky and lipophilic character are known to the skilled man and are intended to be included within the term "bulky and lipophilic" amino acid. Suitable amino acids include thyroxine and the following commercially available amino acids and their derivatives:

L-3-benzothienylalanine, CAS=72120-71-9 (Synthetech), D-3-benzothienylalanine, CAS=111139-55-0 (Synthetech), L-4,4'-biphenylalanine (Synthetech), D-4,4'-biphenylalanine (Synthetech), L-4-bromophenylalanine, CAS=24250-84-8 (Synthetech), D-4-bromophenylalanine, CAS=62561-74-4 (Synthetech), L-2-chlorophenylalanine, CAS=103616-89-3 (Synthetech), D-2-chlorophenylalanine, CAS=80126-50-7 (Synthetech), L-3-chlorophenylalanine, CAS =80126-51-8 (Synthetech), D-3-chlorophenylalanine, CAS=80126-52-9 (Synthetech), L-4-chlorophenylalanie, CAS=14173-39-8 (Synthetech), D-4-chlorophenylalanine, CAS=14091-08-8 (Synthetech), L-3-cyanophenylalanine, CAS=57213-48-6 (Synthetech), D-3-cyanophenylalanine (Synthetech), L-4-cyanophenylalanine (Synthetech), D-4-cyanophenylalanine (Synthetech), L-3,4-dichlorophenylalanine, CAS=52794-99-7 (Synthetech), D-3,4-dichlorophenylalanine, CAS=52794-98-6 (Synthetech), L-3,3-diphenylalanine (Synthetech), D-3,3-diphenylalanine (Synthetech), L-homophenylalanine, CAS= 943-73-7 (Synthetech), D-homophenylalanine, CAS= 82795-51-5 (Synthetech), L-2-indanylglycine (Synthetech), D-2-indanylglycine (Synthetech), L-4-iodophenylalanine, CAS=24250-85-9 (Synthetech), D-4-iodophenylalanine, CAS=62561-75-5 (Synthetech), L-1-naphthylalanine, CAS=55516-54-6 (Synthetech), D-1-naphthylalanine, CAS=78306-92-0 (Synthetech), L-2-Naphthylalanine, CAS=58438-03-2 (Synthetech), D-2-naphthylalanine, CAS=76985-09-6 (Synthetech), L-3-trifluoromethyl-phenylalanine, CAS=14464-68-7 (Synthetech), D-3-trifluoromethylphenyl-alanine (Synthetech), L-4-trifluoromethylphenylalanine, CAS=114926-38-4 (Synthetech), D-4-trifluoromethyl-phenylalanine, CAS=114872-99-0 (Synthetech), Boc-L-tert-leucine (Neosystem Laboratoire), Fmoc-L-tert-leucine (Neosystem Laboratoire), Fmoc-D-homoleucine (Neosystem Laboratoire), Fmoc-L-homoleucine (Neosystem Laboratoire), Boc-D-homophenylalanine (Neosystem Laboratoire), Boc-L-homophenylalanine (Neosystem Laboratoire), Fmoc-4-methyl-D-phenylalanine (Neosystem Laboratoire), Fmoc-4-methyl-L-phenylalanine (Neosystem Laboratoire), 2,6-dichlorobenzyltyrosine, CAS =40298-71-3 (Senn Chemicals), Benzyltyrosine Fmoc (Senn Chemicals), Cyclohexyltyrosine Fmoc (Senn Chemicals), L-t-butylcysteine, CAS 2481-09-6 (Senn Chemicals), D-t-butylcysteine (Senn Chemicals), 1-Aminocyclopentane-1-carboxylic acid, CAS=52-52-8 (Senn Chemicals), L-3,5-diiodotyrosine, CAS=300-39-0 (Senn Chemicals), D-3,5-diiodotyrosine (Senn Chemicals), L-3,5-dibromotyrosine (Senn Chemicals), D-3,5-dibromotyrosine (Senn Chemicals), L-t-butyltyrosine (Senn Chemicals), L-t-butyltyrosine (Senn Chemicals), N-Acetylhomotryptophan (Toronto Research), 7-Benzyloxytryptophan (Toronto Research), Homotryptophan (Toronto Research), 3-(-Anthracenyl)-L-alanine Boc (or Fmoc) (Peninsula Laboratories), 3-(3,5-Dibromo-4-chlorophenyl)-L-alanine (Peninsula Laboratories), 3-(3,5-Dibromo-4-chlorophenyl)-D-alanine (Peninsula Laboratories), 3-(2-Quinoyl)-L-alanine Boc (or Fmoc) (Peninsula Laboratories), 3-(2-Quinoyl)-D-alanine Boc (or Fmoc) (Peninsula Laboratories), 2-Indanyl-L-glycine Boc (Peninsula Laboratories), 2-Indanyl-D-glycine Boc (Peninsula Laboratories), Cyclopentyl-L-glycine Boc (Peninsula Laboratories), Cyclopentyl-D-glycine Boc (Peninsula Laboratories), L-γ-Methyl-leucine Fmoc (Peninsula Laboratories), L-p-t-butoxyphenylglycine Fmoc (RSP), L-2-t-butoxyphenylalanine Fmoc (RSP), L-3-t-butoxyphenylalanine Fmoc (RSP), L-homotyrosine, O-t-butyl ether Fmoc (RSP), L-p-t-butoxymethylphenylalanine Fmoc (RSP), L-p-methylphenylalanine Fmoc (RSP), L-p-ethylphenylalanine Fmoc (RSP), L-p-iso-propylphenylalanine Fmoc (RSP), L-p-methoxyphenylalanine Fmoc (RSP), L-p(tBu-thio) phenylalanine Fmoc (RSP), L-p-(Trt-thiomethyl) phenylalanine Fmoc (RSP), L-p-hydroxymethyl-phenylalanine, O-t-butyl (RSP), L-p-benzoylphenylalanine (Advanced ChemTech), D-p-benzoyl-phenylalanine (Advanced ChemTech), L-α-cyclohexylglycine HCl (Advanced ChemTech), D-α-cyclohexylglycine HCl (Advanced ChemTech), O-benzyl-L-homoserine Boc (Advanced ChemTech), O-benzyl-D-homoserine Boc (Advanced ChemTech), L-β-1-Naphthyl-alanine (Advanced ChemTech), D-β-1-Naphthyl-alanine (Advanced ChemTech), L-penta-fluorophenylalanine Boc (Advanced ChemTech), D-penta-fluorophenylalanine Boc (Advanced ChemTech), D-penta-fluorophenylalanine Fmoc (Advanced ChemTech), 3,5-Diiodo-L-tyrosine Fmoc (Boc) (Advanced ChemTech), L-Thyroxine Na, CAS=6106-07-6 (Novabiochem), 3,3',5-Triiodo-L-thyronine Na, CAS=55-06-1 (Novabiochem).

Surprisingly, it has been found that standard chemical protecting groups when attached to an R group and thus increasing the bulk and lipophilicity of the residue can increase the bioactivity of peptides. Such protecting groups are well known in the art. Suitable protecting groups which can significantly enhance anti-bacterial activity include Pmc (2,2,5,7,8-pentamethylchroman-6-sulphonyl), Mtr (4-methoxy-2,3,6-trimethylbenzenesulfonyl) and Pbf (2,2,4,6,7-pentamethyldihydrobenzofuransulfonyl) which may conveniently increase the bulk and lipophilicity of aromatic amino acids, e.g. Phe, Trp and Tyr. Also, the tert butyl group is a common protecting group for a wide range of amino acids and is capable of providing bulky and lipophilic amino acids as described herein, particularly when modifying aromatic residues. The Z-group (carboxybenzyl) is a further protecting group which can be used to increase the bulky and lipophilicity of an amino acid to provide a peptide in accordance with the invention.

Although an initial observation of increased bioactivity was as a result of a serendipitous transfer of the protecting group Pmc within the peptide from the guanidino group of arginine to tryptophan, amino acids such as Trp which carry the protecting group can be synthesised directly and incorporated into the peptide. This observation of the transfer of Pmc from Arg to Trp has been observed by Stierandova et al. in Int. J. of Peptide Science (1994) 43, 31–38. Peptides in accordance with the invention can be made by utilising this transfer of the protecting group from Arg to Trp. When these two amino acids are separated by 1–3 amino acids, the transfer of Pmc is most efficient. Peptides according to the invention may thus conveniently comprise an amino acid carrying a protecting group, e.g. Trp with Pmc attached in the 2 position of the indole ring. The Pmc group may be attached to a Trp which has been added or to a Trp residue present in the original peptide. In a preferred embodiment of the invention, peptides will incorporate one or more additional tryptophan residues which can then be modified to further increase its bulky and lipophilic character and thus provide a peptide according to the invention.

Secondly, the bulky and lipophilic nature of an amino acid and thus of the peptide can also be enhanced by N- or C-terminal modification and such modifications result in further peptides according to the present invention.

Thus peptides may, in addition to or instead of incorporating a bulky and lipophilic R group, therefore be modified to incorporate a bulky and lipophilic group at the N- and/or C-terminus. In this case, the N- or C-terminal residue which is modified to include a bulky and lipophilic N- or C-terminal group is the "extra bulky and lipophilic amino acid". The bulky and lipophilic N- or C-terminal groups include organic groups such as protecting groups, especially Fmoc, Boc or other standard N terminal protecting groups or branched, linear or cyclic alkyl groups of formula $CH_3(CH_2)_n$, wherein n is between 5 and 20, preferably between 8 and 14 and most preferably 10 to 12 or branched, linear or cyclic acyl groups having between 6 and 21, preferably 9 and 15 and most preferably 11 to 13 carbon atoms.

Particularly, it has been found that peptides having antibacterial and/or antitumor activity but a low toxicity can be made by incorporating N-terminal modifications which include a cyclic group, preferably a 5- or 6-membered ring which may be alkyl or aryl, e.g. benzyl. More preferably the group which comprises the N-terminal modification encompass 2 or more fused rings one or more of which may be a 5-membered ring e.g. adamantyl or Fmoc. It has surprisingly been found that groups which are three dimensional in character, such as those which incorporate a fused ring system which do not lie in a single plane have particularly advantageous properties.

More specifically, it has been found that peptides having antibacterial and/or antitumoral activity but a low toxicity can be made by incorporating N-terminal modifications which include a cyclic group, preferably a 5- or 6-membered ring which may be alkyl or aryl. More preferably the group which comprises the N-terminal modification encompasses 2 or more fused rings one or more of which may be a 5-membered ring e.g. adamantyl or Fmoc. It has surprisingly been found that groups which are three dimensional in character, such as those which incorporate a fused ring system which does not lie in a single plane have particularly advantageous properties.

Suitable molecules which could be used to modify the N-terminus include:

cis-Bicyclo[3.3.0]octan-2-carboxylic acid, [18209-43-3] (Aldrich); Abietic acid, [514-10-3] (Aldrich); Ursolic acid, [77-52-1] (Aldrich); (1,2-Methanofullerene $C_{60}$)-61-carboxylic acid, [155116-19-1] (Fluka); Dimethyl cubane-1,4-dicarboxylate, [29412-62-2] (Fluka); 2-Norbornaneacetic acid, [1007-01-8] (Aldrich); 4-Pentylbicyclo[2.2.2]octane-1-carboxylic acid, [73152-70-2] (Aldrich); 3-Noradamantanecarboxylic acid, [16200-53-6] (Aldrich); 9-Fluoreneacetic acid, [6284-80-6] (Aldrich); cis-Decahydro-1-naphthol, [36159-47-4] (Aldrich); 9-Ethyl-bicyclo[3.3.1]nonane-9-ol, [21915-33-3] (Aldrich); 3-Quinuclidinol, [1619-34-7] (Aldrich); [[(1S)-endo]-(−)-Borneol, [464-45-9] (Aldrich); (1R,2R,3R,5S)-(−)-Isopinocampheol, [25465-65-0] (Aldrich); Dehydroabietylamine [1446-61-3] (Aldrich); (±)-3-Aminoquinuclidine [6530-09-2] (Aldrich); (R)-(+)-Bornylamine, [32511-34-5] (Aldrich); 1,3,3-Trimethyl-6-aza-bicylo[3.2.1]octane [53460-46-1] (Aldrich); 1-Adamantylamine, [768-94-5] (Aldrich); 9-Aminofluorene, [5978-75-6] (Aldrich); (1R)-(−)-10-Camphorsulfonic acid, [35963-20-3] (Aldrich); 5-Isoquinolinesulfonic acid, [27655-40-9] (Aldrich); 2-Quinolinethiol, [2637-37-8] (Aldrich); 8-Mercaptomenthone, [38462-22-5] (Aldrich).

N-terminal modifications to provide peptides in accordance with the invention will therefore typically comprise a bulky and lipophilic group R which may be attached directly to the N-terminal amine to form a mono-, di- and possibly cationic trialkylated N-terminal amine. Alternatively, the R group may be attached via a linking moiety e.g. a carbonyl group (RCO) e.g. adamantyl or benzyl, carbamate (ROCO) e.g. Fmoc, or a linker which forms urea (RNHCO) or ($R_2$NCO) or by a linker which forms a sulfonamide, boronamide or phosphonamide. Sulfonamide forming linkers may be particularly useful when a more stable peptide is required. The bulky and lipophilic group R comprises a preferably saturated cyclic group, more preferably a polycyclic group wherein the cyclic groups are fused or bridged.

Peptides incorporating such N-terminal modifications are particularly effective as anti-tumour peptides and surprisingly, the presence of a cyclic, preferably multicyclic, N-terminal group provides peptides with an ability to kill tumour cells e.g. Meth A cells (from a fibrosarcoma) but have little cytotoxic activity against normal cells e.g. red blood cells or normal fibroblast cells. For example, cyclohexyl—LFB 17–31 at a concentration of 46 µg/ml killed 50% of Meth A cells (murine sarcoma cell line) but did not kill 50% of red blood cells or fibroblasts even at a concentration of 1000 µg/ml. This selectivity is, of course, highly desirable in the in vivo treatment of established tumours.

Particularly effective C-terminal modifications according to the present invention have also been investigated. Amidation of the C-terminus in order to manipulate the overall charge of a peptide is known but it has now been found that larger C-terminal modifications, including the formation of esters, including thioesters or substituted primary and secondary amides result in peptides with good cytotoxic activity. The C-terminal modifying groups will advantageously contain more than 4, preferably 6 or more non-hydrogen atoms and form e.g. a benzyl ester or amide. Other C-terminal groups include naphthylamine, substituted aromatic amines such as phenyl-ethylamine, mono, di- or tri-amino alkyl groups etc., groups incorporating a cyclic group being preferred. Standard C-terminal protecting groups are also available as activity enhancing modification.

C-terminal modifications to provide peptides in accordance with the invention will therefore typically comprise a bulky and lipophilic group R which may be attached directly to the C-terminal carboxy group to form a ketone. Alternatively, the R group may be attached via a linking moiety, e.g. (OR) which forms an ester at the C-terminus, (NH—R) or (NR$_2$, wherein the two R groups needs not be the same) which form primary and secondary amide groups respectively at the C-terminus or groups (B—(OR)$_2$) which form boronic esters or phosphorous analogs. The bulky and lipophilic group R preferably comprises at least 4 non-hydrogen atoms.

Typically, the peptides of this aspect of the invention can be represented by the following formula:

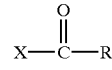

wherein

X=a lactoferrin derived peptide of 7–25 amino acids in length incorporating 3 cationic residues which is capable of forming an amphipathic α-helix;

R=SR$^1$, OR$^1$ or R$^1$; and

R=alkyl, cycloalkyl, aminoalkyl or aryl optionally substituted by hydroxy, alkoxy, acyloxy, alkoxycarbonyloxy, amino, oxo or fluoro groups and optionally interrupted by oxygen, nitrogen, sulphur or phosphorous atoms.

The substituted R$^1$ groups may be mono or polysubstituted. The term "acyl" as used herein includes both carboxylate and carbonate groups.

As used herein, the term "alkyl" includes a long or short chain straight-chained or branched aliphatic saturated or unsaturated hydrocarbon group. R$^1$ may contain up to 40 non-hydrogen atoms, preferably between 4 and 12, more preferably 6 to 10 such atoms.

A lipophilic molecule is one which associates with its own kind in an aqueous solution, not necessarily because the interactions between the lipophilic molecules are stronger than between the lipophilic molecule and water but because interactions between a lipophilic molecule and water would destroy the much stronger interactions between the water molecules themselves. It is therefore preferable that the group which gives the amino acid its bulky and lipophilic character, whether it be an R group or N- or C-terminal modifying group, should not contain many polar functional groups, e.g. no more than 4, preferably 2 or less, such groups would increase the binding interaction with the aqueous surroundings and hence lower the lipophilicity of the molecules. Highly lipophilic groups thus being preferred. For example, a phenyl group as a component of a bulky and lipophilic group would be preferred to a pyridyl group, even though they have the same number of non-hydrogen atoms and are of a similar overall size.

The bulky and lipophilic group would typically have at least 3 or 4, preferably at least 5 or 6, more preferably 7 or more, most preferably 9 or more non-hydrogen atoms. The term 'non-hydrogen' atoms is used to indicate that hydrogen atoms are not included when counting the number of atoms present in a group or molecule.

Peptides according to the invention may contain one or more of the above types of bulky and lipophilic groups, preferably the peptide will incorporate at least one additional bulky and lipophilic R group and either an N- or C-terminal modification as discussed above. Peptides may include all three types of bulky and lipophilic groups.

The peptides of the invention will typically contain between 1 and 12, preferably 3 and 9, more preferably 4 to 7 bulky and lipophilic amino acids, depending on the length of the peptide. One or more, e.g. 1 to 4 of these being extra bulky and lipophilic amino acids not present in the native sequence. The 'native sequence' being the corresponding sequence (which may be identified using alignment software) in naturally occurring lactoferrin from any species. The native sequences typically being a fragment of LFB or its equivalent in other species. The native sequence for modification is selected and the modifications are identified with reference to this sequence, e.g. LFB 17–31 W7 Pmc, a 15 mer peptide having the sequence of residues 17–31 of bovine lactoferrin but wherein the 7th residue has been replaced by tryptophan, one or more of the tryptophan residues also being modified by Pmc. The native sequence in terms of the order of amino acids is naturally occurring, although the particular fragment may be generated by chemical or enzymatic cleavage and not exist naturally at that length.

Sequence homology for such short peptides of the invention can most simply be calculated by comparing the two sequences, residue for residue, to determine whether the two amino acids at positions 1, 2, 3 etc are the same or in the same group as previously defined. Thus, LFB (17–31)W3 has a 93.3% homology with LFB (17–31). Computer programs for calculating sequence homology are also known in the art and these may allow for additions (insertions) or deletions (gaps) in the sequence.

Amino acid sequence homology may be determined using the BestFit program of the Genetics Computer Group (CGC) Version 10 Software package from the University of Wisconson. The program uses the local homology algorithm of Smith and Waterman with the default values: Gap creation penalty=8, Gap extension penalty=2, Average match=2.912, Average mismatch=−2.003. Such a program could therefore be used to assess homology of the peptides of the invention with the native sequence, particularly if the modified peptide also incorporates gaps or insertions. Such a program is most suited to establishing the alignment between two sequences, again particularly when the modified sequence incorporates gaps or insertions.

For such peptides which comprise only genetically coded amino acids, similarity of the modified peptides with a known or natural cytotoxic peptide can be expressed by stringency of hybridisation of nucleic acid molecules encoding the two sequences rather than % homology. In this case, the ssDNA molecule encoding the modified peptide should hybridise with the ssDNA molecule complementary to the ssDNa molecule which encodes the known or natural cytotoxic peptide.

Sequences which "hybridise" are those sequences binding (hybridising) under non-stringent conditions (e.g. 6×SSC, 50% formamide at room temperature) and washed under conditions of low stringency (e.g. 2×SSC, room temperature, more preferably 2×SSC, 42° C.) or conditions of higher stringency (e.g. 2×SSC, 65° C.) (where SSC= 0.15M NaCl, 0.015M sodium citrate, pH 7.2).

Preferbly, the sequences will hybridise under conditions of higher stringency as defined above, or but for the degeneracy of the code, the sequences would hybridise under high stringency conditions.

Preferably, the peptides will include 1 or 2 additional genetic bulky and lipophilic amino acids and may otherwise be identical to the known cytotoxic peptide or incorporate only conservative substitutions.

Further preferred peptides according to the present invention include those which have retained the original sequence of a fragment of lactoferrin (and could thus be considered to have 100% sequence homology with the native sequence) but wherein the extra bulky and lipophilic amino acid is in the form of a modification to one of the original residues. This modification may be to the N- or C-terminus of the peptide, in which case the N- or C-terminal residues would be the extra bulky and lipophilic amino acid or to the R group of one of the residues. Preferred amongst such modifications is modifying an already bulky amino acid such as tryptophan to make it more bulky, in the context of the present invention, this is still considered to be an "extra" bulky and lipophilic amino acid.

Peptides incorporating an extra bulky and lipophilic amino acid will preferably exhibit an enhanced cytotoxic effect against bacterial or tumour cells while the toxicity of the peptides, e.g. their hemolytic activity is reduced or only moderately increased as compared to the native or original peptide.

In the context of the present invention, "cyclic derivatives" refers to peptides which are cyclic as a result of one or more di-sulphide bridges. For some peptides incorporating two or cysteine residues, this will be the naturally occurring form and production of a linear peptide will require the modification of the cysteine residues.

Typically, the peptide prior to incorporation of an extra bulky and lipophilic amino acid will exhibit some cytotoxic activity, this activity being enhanced by the incorporation of a non-genetic bulky and lipophilic amino acid.

In absolute terms, the peptides according to the invention will incorporate a certain number of extra bulky and lipophilic amino acids. Typically between 1 and 6, preferably 1 and 4 extra bulky and lipophilic amino acids, depending on the overall length of the peptide. For example a 7 to 10 mer peptide may have between 1 and 3 extra bulky and lipophilic residues, a 19–25 mer peptide may have between 1 and 5, preferably between 2 and 3 extra bulky and lipophilic residues.

Peptides according to the invention may conveniently comprise an additional standard bulky and lipophilic amino acid, e.g. Trp, as well as an amino acid carrying a protecting group, e.g. Trp with Pmc attached in the 2 position of the indole ring. The Pmc group may be attached to the Trp which has been added or to a naturally occurring Trp residue.

In addition to the bulky and lipophilic modifications, the lactoferrin derived peptides according to the invention may advantageously incorporate further modifications. In particular, increasing the overall positive charge of the peptide, for example by replacing one or more naturally occurring amino acids, particularly non-essential amino acids, with positively charged residues such as lysine or arginine may further enhance the activity of the lactoferrin peptide. "Positively charged" refers to the side chain (R group) of the amino acid residue which has a net positive charge at pH 7.0. In the case of peptides for use as antitumour agents, where the peptide may advantageously be capable of forming α-helix, substitutions within the peptide sequence which serve to lower the angle subtended by the cationic sector, i.e. the angle of the positively charged face of the helix may further enhance activity. In fact, lowering the angle subtended may have a greater impact on activity than the net positive charge per se. Other residues may advantageously be replaced by alamine residues.

Peptides according to the invention may conveniently comprise an additional bulky and lipophilic amino acid, e.g. Trp, as well as an amino acid carrying a protecting group, e.g. Trp with Pmc attached in the 2 position of the indole ring. The Pmc group may be attached to the Trp which has been added or to a naturally occurring Trp residue.

For any lactoferrin derived peptide, suitable positions for incorporation of extra bulky and lipophilic amino acids in order to increase cytotoxicity can be identified in a number of ways. As discussed above, "incorporation" may include modification of an existing residue. An alanine scan (involving sequential substitution of the amino acids with alanine) can be used to identify non-essential amino acids which could be substituted by a bulky and lipophilic amino acid or modified to increase its bulk and lipophilicity. Alternatively, a candidate peptide which forms an amphiphatic a-helix can be represented as a 'helical wheel' of residues and the cationic residues identified. These cationic residues will form positively charged domains or regions within the three-dimensional helical peptide structure and suitable positions for incorporation of or modification to provide an extra bulky and lipophilic amino acids are generally adjacent to or between such cationic domains when viewed along the axis of the helical wheel.

It has even been found that peptides having enhanced antibacterial and/or antitumoural activity and preferably reduced toxicity can be prepared by moving a bulky and lipophilic amino acid from its position in the original/native sequence to a region adjacent to the cationic sector, thus the oveall amino acid composition of the peptide remains unchanged. Such 7–25 mer lactoferrin peptides which have 3 or more cationic residues and are capable of forming an amphipathic α-helix and which have an extra bulky and lipophilic amino acid adjacent to the cationic sector, said extra bulky and lipophilic amino acid being taken from another, non-preferred, position in the sequence constitute a further aspect of the present invention. In place of the bulky and lipophilic amino acid can be put the residue from adjacent to the cationic sector which the bulky and lipophilic amino acid replaces or any other less bulky and lipophilic amino acid. Suitable bulky and lipophilic amino acids in non-preferred positions which can be moved into the region adjacent to the cationic sector (preferred position) can be identified by e.g. an alanine scan which identifies non-essential amino acids or by studying a helical wheel arrangement, non-preferred positions typically being opposite a cationic domain.

It has also been found that peptides having reduced toxicity but still having reasonable antibacterial or antitumoural activity (i.e. having enhanced selectivity) may be prepared by replacing a non-essential highly bulky and lipophilic amino acid such as tryptophan or phenylalanine with a less bulky and lipophilic amino acid e.g. isoleucine or leucine or even alanine or lysine. Generally, a "non-essential" bulky and lipophilic amino acid will be positioned on the opposite side of the helix from the cationic sector, such non-essential bulky and lipophilic amino acids can be identified using a helical wheel diagram or by an alanine scan. These peptides should nevertheless retain at least 3 bulky and lipophilic amino acids as herein defined. Thus, modified cytotoxic peptides having 7 to 25 amino acids, at least three cationic residues and at least three bulky and lipophilic amino acids and being capable of forming an amphipathic α-helix, wherein one non-essential tryptophan or phenylalanine residue in the original/native sequence is replaced by a less bulky and lipophilic residue e.g. isoleucine or alanine constitute a further aspect of the present invention.

Other suitable sites for incorporation of a bulky and lipophilic amino acid are positions at or near, preferably adjacent, to an existing lipophilic amino acid. Proximity is judged in terms of the secondary rather than primary structure of the peptide. The techniques involved in performing an alanine scan and in constructing helical wheel diagrams are well known in the art.

In the case of LFB(17–31) (a 15 amino acid fragment of LFB which lacks the ten C-terminal residues), non-essential amino acids determined using an alanine scan were Cys(3), Gln(7) and Gly(14), here the numbering is in absolute terms relating to the peptide itself. Analogs of LFB(17–31) wherein these amino acids are replaced by bulky and lipophilic amino acids may be particularly effective.

Particularly preferred peptides according to the present invention are those which are based on bovine lactoferrin (LFB) or fragments (e.g. LFB 17–31) thereof or the equivalent fragment of lactoferrin from other animals.

A particular advantage of the peptides of the present invention is their small size, peptides having 15 or fewer amino acids being preferred, conveniently of 9 or 10 amino acids or less. One such effective small peptide is LFB (17–27) wherein the Lys28, Leu29, Gly30 and Ala31 from the C-terminal end of LFB(17–31) have been omitted. The peptides may be produced by any known method, conveniently by enzymatic digestion or chemical cleavage of native peptides and subsequent modification or by direct synthesis from the amino acid building blocks. The shorter the desired peptide the better as far as manufacture is concerned, particularly for direct synthesis which is the preferred method of manufacture, as this limits the problems associated with chirality of the amino acids. In addition, short peptides are good for biodelivery. There is a growing demand for antibiotics which can be administered without the need for an injection, such as by inhalation and absorption across the blood capillaries of the nasal passages. A 10 mer peptide could easily be administered in this way but peptides in excess of 25 amino acids in length could not be delivered by inhalation.

It would also be desirable to increase the circulating half-life of the peptide and this could be achieved by further modifying the peptides of the invention to include artificial amino acids as they are resistant to enzymatic breakdown. Long peptides are susceptible to breakdown by endopeptidases which cleave internally of the peptide, shorter peptides would be less vulnerable to cleavage by endopeptidases and breakdown by exopeptidases, which attack the ends of a peptide, could be reduced by acetylating the N terminus and otherwise blocking the C terminus.

It has also been observed that the incorporation of enantio amino acids can significantly increase the bioactivity of the peptides of the invention and such peptides constitute a further preferred embodiment of the present invention. Excellent antimicrobial activity has been shown for Enantio peptides which are the exact mirror image of the native peptide and Retro-Enantio peptides which adopt the same a-helical confirmation as the native peptide except the amide bonds point in opposite directions. Thus a further aspect of the present invention comprises the enantio or retro-enantio form of a lactoferrin derived peptide, particularly LFB or fragments thereof; as well as lactoferrin derived peptides which incorporate one or more D amino acids. Further preferred embodiments of the present invention are thus peptides as defined herein which incorporate one or more extra bulky and lipophilic amino acids and also comprise one or more D amino acids e.g. ⅓ or ½ or ⅔ of the amino acids in the peptide are in the D form and these may be arranged in any way throughout the sequence, e.g. alternately with L amino acids.

Enantio amino acids are also resistant to enzymatic breakdown and the resultant increase in half-life of the peptides may go some way to explaining the enhanced anti-bacterial activity. Enantio amino acids are expensive and this is a further reason why the relatively short peptides of the present invention are particularly advantageous.

By the term "capable" of forming an amphipathic α-helix is meant that the peptide may, in certain circumstances, form an α-helix. Peptides may not necessarily have the α-helix as their natural configuration in aqueous media but are able, for example in the presence of helix providing substances such as Sodium dodecylsulphate (SDSS, 2,2,2-trifluoroethanol (TFE), 1,1,1,3,3,3-hexafluoroisopropanol (HFIP) or micelles (other than SDS) and cell membranes (artificial and natural) to form an a-helix or substantially α-helical structure. Circular dichroism may conveniently be used to test for the presence of an α-helix. Of more importance than the formation of an α-helix is the fact that the peptides are amphipathic, i.e. that the 2° structure of the peptide, whether it is a α-helical or not is amphipathic. This is evidenced by the activity of the enantio peptides of the invention and peptides incorporating D amino acids which are not a-helical.

In addition, the present invention relates to non-peptide compounds showing the same cytotoxic activity as their proteinaceous counterparts. Such petidomimetics or "small molecules" capable of mimicking the activity of a protein or peptide are likely to be better suited for e.g. oral delivery due to their increased chemical stability. Such compounds will include a part which corresponds to the "extra bulky and lipophilic amino acid" as previously defined. They will include a group which corresponds to the R group, or N- or C-terminal modifying group of said extra bulky and lipophilic amino acid.

It is now commonplace in the art to replace peptide or protein-based active agents e.g. therapeutic peptides with such peptidomimetics having functionally-equivalent activity. Various molecular libraries and combinatorial chemistry techniques exist and are available to facilitate the identification, selection and/or synthesis of such compounds using standard techniques (Kieber-Emons, T. et al. Current Opinion in Biotechnology 1997 8: 435–441). Such standard techniques may be used to obtain the peptidomimetic compounds according to the present invention, namely peptidomimetic organic compounds which show substantially similar or the same cytotoxic activity as the peptides of the invention, e.g. as described herein in the Examples.

A further aspect of the invention thus provides a biomimetic organic compound based on the peptides of the invention, characterised in that said compound exhibits cytotoxic, e.g. antibacterial or antitumoural activity, at at least the level exhibited by the peptides of the invention as hereinbefore defined.

The term "cytotoxic" is intended to refer not only to an activity against prokaryotic cells but also against eukaryotic cells. Although in certain circumstances it is desirous to have a peptide which has a good anti-bacterial activity but does not lyse or otherwise destroy the cells of the patient, peptides within the scope of the present invention have been shown to have an anti-tumoural activity. The anti-tumoural activity of these peptides and medicaments containing them constitute further aspects of the present invention. Anti-tumoural activity includes the destruction or reduction in size or number of benign or malignant tumours and the prevention or reduction of metastasis.

In general, lactoferrin derived peptides according to the invention which have no non-genetic amino acids and have a good activity against tumour cells will have 25–10, preferably 12–20 e.g. 18 amino acids. Peptides according to a non genetic bulky and lipophilic group and having good anti-tumoural activity will generally be shorter, with 7–20, preferably 10–20, more preferably 10–15 amino acids. By way of example, LFB 17–27 A7, M3, R2,11W4, 10, Y1-NH$_2$ PMC and LFB 18–24 R1,7 W2,3,6-NH$_2$ PMC require only 50 and 38 µg/ml respectively to kill 50% of Meth A cells.

In general, peptides having good activity against tumours will be longer than those exhibiting good anti-bacterial activity. Anti-bacterial peptides will typically have 7 to 20, preferably 7 to 14, e.g. 8 or 9 amino acids.

The anti-tumoural activity of the modified peptides is much better than could be predicted merely from the fact that the peptides appear to have a lytic effect on bacterial cells. The observed lytic effect on tumour cells in vitro is powerful and tumour regression in mice is very rapid, occurring within 3–6 days. It appears that there is induction of an immunological memory, as inoculation of tumour cells in mice after the treatment and regression of the original tumour did not give rise to any secondary tumour growth.

Importantly, we have demonstrated regression of established tumours, even with unmodified LFE. In this context, "unmodified" refers also to fragments of LFB which exhibit this antitumoural activity, e.g. LFB(17–31). The peptide may be cyclic or linear, preferably cyclic. This new clinical use of LFB represents a further aspect of the present invention as we provide for the use of LFB and fragments thereof in the manufacture of a medicament for the treatment of solid tumours. The ability to treat solid tumours is particularly useful when a tumour is unresectable. A further advantage is that the observed cytolytic effect in tumours is not species specific and thus the peptides have utility in treating human tumours.

In a further aspect of the present invention, we provide a method of treating solid tumours which comprises administration of LFB or a fragment thereof in a dose sufficient to cause regression of the tumour.

Suitable doses for treatment of tumours with bioactive peptides will be known to the skilled man and doses used in the animal experiments described herein can be used to estimate an appropriate dose for other animal and human patients. Administration of a peptide may be daily, more usually on alternate days or on every 3rd or 4th day. 1 to 10, typically 2 to 5 administrations may result in successful treatment. Similar treatment protocols will be used for treatment of bacterial or viral infections.

Peptides according to the invention will preferably be at least as cytotoxic as LFB (17–31). Some peptides according to the invention will be more active in some respects (e.g. antitumoural) than LFB (17–31) but less active in other respects e.g. against E. coli. Some peptides may be less active but other properties e.g. a low hemolytic activity will render them useful in certain applications.

It has also been observed that in certain circumstances, reducing the bulk and lipophilicity of an amino acid may result in a significant decrease in toxicity and only a marginal decrease in anti-bacterial or anti-tumoural activity, thus resulting in a very useful therapeutic peptide. Specifically, replacing a tryptophan residue, the most bulky and lipophilic of the genetic amino acids or phenylalanine with another, less bulky and lipophilic amino acid, e.g. isoleucine or leucine or by alanine or even lysine can result in peptides with good to moderate anti-bacterial or anti-tumoural activity and very low toxicity. These peptides, wherein a tryptophan or phenylalanine residue has been replaced should nevertheless retain at least 3 bulky and lipophilic amino acids as herein defined. Thus, modified cytotoxic lactoferrin derived peptides having 7 to 25 amino acids, at least three cationic residues and at least three bulky and lipophilic amino acids and which is capable of forming an amphipathic α-helix, wherein a tryptophan or phenylalanine residue in the native sequence is replaced by a less bulky and lipophilic residue e.g. isoleucine constitute a further aspect of the present invention. The replaced tryptophan or phenylalanine residue should be non-essential and will typically be opposite a cationic sector of the helix. Non-essential residues can be determined by an alanine scan or helical wheel drawing.

The antibacterial activity of the peptides of the invention may manifest itself in a number of different ways. Certain modifications may result in peptides which are bacteriostatic and others in peptides which are bacteriocidal. Advantageously, the majority of peptides according to the invention are bacteriocidal. Thus, inter alia, the invention also provides a method of inhibiting the growth of bacteria comprising contacting the bacteria with an inhibiting effective amount of a cytotoxic peptide according to the invention.

The term "contacting" refers to exposing the bacteria to a peptide so that it can effectively inhibit, kill or lyse bacteria, bind endotoxin (LPS), or, permeabilize gram-negative bacterial outer membranes. Contacting may be in vitro, for example by adding the peptide to a bacterial culture to test for susceptibility of the bacteria to the peptide. Contacting may be in vivo, for example administering the peptide to a subject with a bacterial disorder, such as septic shock. "Inhibiting" or "inhibiting effective amount" refers to the amount of peptide which is required to cause a bacteriastatic or bacteriacidal effect. Examples of bacteria which may be inhibited include *E. coli, P. aeruginosa, E. cloacae, S. typhimurium* and *S. aureus*. The method of inhibiting the growth of bacteria may further include the addition of antibiotics for combination or synergistic therapy. The appropriate antibiotic administered will typically depend on the susceptibility of the bacteria such as whether the bacteria is gram negative or gram positive, and will be easily discernable by one of skill in the art.

In addition, different modifications may enhance the antibacterial activity against certain types of bacteria more than against other types. For example *S. aureus* is particularly susceptible to very large bulky and lipophilic groups, typically those having at least 12 or 18 non-hydrogen atoms in the R group e.g. those peptides which incorporate a Pmc modified tryptophan residue. In addition, R groups which are substantially planar have good activity against *E. coli*, while a more 3-dimensional group of comparable lipophilicity is preferred for producing good activity against *S. aureus*.

It has been found that the sequence of bovine lactoferricin (LFB 17–41) can be reduced by up to about 10 residues at the C-terminal end, e.g. to LFB(17–31) without significant loss of antibacterial activity. LFB 17–31= FKCRRWQWRMKKLGA. As well as bovine lactoferricins, we have identified the regions corresponding to LFB 17–31 in man, LFH=TKCFQWQRNMRKVRG, goat, LFC= SKCYQWQRRMRKLGA, mice, LFM=EKCLRWQNE-MRKVGG and pigs, LFP=SKCRQWQSKIRRTNP and such regions are also suitable for manipulation according to the invention.

A variant of the effects of an increase in lipophilicity of certain peptides discussed above has been observed and a further aspect of the present invention comprises a cytotoxic lactoferrin peptide of 15 amino acids or less characterised in that it has an additional bulky/lipophilic group at one end. In respect of this aspect of the invention, the bulky/lipophilic group includes organic groups such as protecting groups, especially Fmoc, Boc or other standard N terminal protecting groups or branched, linear or cyclic alkyl groups of formula $CH_3(CH_2)$ wherein n is between 5 and 20, preferably between 8 and 14 and most preferably 10 to 12 or branched, linear or cyclic acyl groups having between 6 and 21, preferably 9 and 15 and most preferably 11 to 13 carbon atoms. For example, an LFB(17–31) peptide having a $CH_3(CH_2)_n$ alkyl group at the N-terminal end had an up to 10 fold increase in antibacterial activity. The groups are attached to N- or C-terminal or close, preferably adjacent, to N- or C-terminal residues. These groups may be attached to native amino acid residues, or non-native amino acids carrying the bulky/lipophilic group may be incorporated into the peptide.

A still further aspect of the present invention is a method of preparing a peptide having enhanced cytotoxic activity and/or improved selectivity for target cell types which comprises incorporating a bulky and lipophilic amino acid into a 7 to 25 mer lactoferrin peptide with three or more cationic residues which is optionally capable of forming an amphiphatic α-helix. Such a method would include, as well as adding or substituting a genetic or non-genetic bulky and lipophilic amino acid, enhancing the bulky and lipophilic nature of one or more of the amino acids by modification of the R group or the N- or C-terminus.

"Incorporating" may include modification of an existing residue or introduction of such a residue into the peptide by addition or substitution, preferably substitution. A synthetic method may be used whereby the non-genetic bulky and lipophilic amino acid is included in sequence in the growing peptide so no post peptide formation processing is required.

When, herein, we refer to a peptide having "enhanced" cytotoxic activity, it is meant that the peptide which has been modified in accordance with the invention has enhanced cytotoxicity against one or more strains of bacteria or types of cancerous cells as compared to the peptide without said modification. By "improved selectivity for target cell types" is meant that the ratio of cytotoxic activity against target cells as compared to non target cell types is increased. In other words, selectivity can be improved if, for example, the antibacterial activity of a peptide is the same before and after modification but the hemolytic activity is decreased after modification. Similarly, useful peptides according to the invention may be made even when hemolytic activity increases, if the antibacterial or antitumoural activity increases by a greater amount. Selectivity may also refer to one type of bacteria over another.

Tryptophan rich analogs of lactoferrin have been shown to be effective as antimicrobial agents. Such analogs preferably have one or two tryptophan residues replacing other, non-essential residues.

In a further aspect, the invention provides a method of enhancing the cytotoxic activity of a lactoferrin peptide of 7 to 25 amino acids in length, which has three or more cationic residues and is optionally capable of forming an amphipathic a-helix which comprises introducing by addition or substitution, preferably substitution, an extra bulky and lipophilic amino acid (e.g. tryptophan).

A 'lactoferrin peptide' is a peptide derived from naturally occurring lactoferrin from any species. The peptides itself may not be naturally occurring, being a fragment of lactoferrin e.g. a fragment of LFB.

The peptides of the invention may be directly synthesised in any convenient way. Generally the reactive groups present (for example amino, thiol and/or carboxyl) will be protected during overall synthesis. The final step in the synthesis will thus be the deprotection of a protected derivative of the invention. As discussed above, certain peptides of the invention will carry a 'protecting group' as this is responsible for enhanced cytotoxicity.

In building up the peptide, one can in principle start either at the C-terminal or the N-terminal although the C-terminal starting procedure is preferred. The non-genetic amino acid can be incorporated at this stage as the sequence is extended or as a result of a post-synthetic modification.

Methods of peptide synthesis are well known in the art but for the present invention it may be particularly convenient to carry out the synthesis on a solid phase support, such supports being well known in the art.

A wide choice of protecting groups for amino acids are known and suitable amine protecting groups may include carbobenzoxy (also designated Z) t-butoxycarbonyl (also designated Boc), 4-methoxy-2,3,6-trimethylbenzene sulphonyl (Mtr) and 9-fluorenylmethoxy-carbonyl (also designated Fmoc). It will be appreciated that when the peptide is built up from the C-terminal end, an amine-protecting group will be present on the α-amino group of each new residue added and will need to be removed selectively prior to the next coupling step.

Carboxyl protecting groups which may, for example be employed include readily cleaved ester groups such as benzyl (Bzl), p-nitrobenzyl (ONb), pentachlorophenyl (oPClP), pentafluorophenyl (OPfp) or t-butyl (OtBu) groups as well as the coupling groups on solid supports, for example methyl groups linked to polystyrene.

Thiol protecting groups include p-methoxybenzyl (Mob), trityl (Trt) and acetamidomethyl (Acm).

A wide range of procedures exists for removing amine- and carboxyl-protecting groups. These must, however, be consistent with the synthetic strategy employed. The side chain protecting groups must be stable to the conditions used to remove the temporary α-amino protecting group prior to the next coupling step.

Amine protecting groups such as Boc and carboxyl protecting groups such as tBu may be removed simultaneously by acid treatment, for example with trifluoroacetic acid. Thiol protecting groups such as Trt may be removed selectively using an oxidation agent such as iodine.

Peptides according to the invention may be prepared by incomplete deprotection to leave groups which enhance the cytotoxic activity of the peptides. Alternatively, modified R and N- and C-terminal groups may be prepared after synthesis of the peptide and associated deprotection.

A particularly preferred method involves synthesis using amino acid derivatives of the following formula: Fmoc-amino acid-Opfp.

A proportion of the peptides of the invention, i.e. those wherein the extra bulky and lipophilic amino acid is one of the genetically coded amino acids will be capable of being expressed in prokaryotic and eukaryotic hosts by expression systems well known to the man skilled in the art. Methods for the isolation and purification of e.g. microbially expressed peptides are also well known. Polynucleotides which encode these peptides of the invention constitute further aspects of the present invention. As used herein, "polynucleotide" refers to a polymer of deoxyribonucleotides or ribonucleotides, in the form of a separate fragment or as a component of a larger construct, e.g. an expression vector such as a plasmid. Polynucleotide sequences of the invention include DNA, RNA and cDNA sequences. Due to the degeneracy of the genetic code, of course more than one polynucleotide is capable of encoding a particular peptide according to the invention.

When a bacterial host is chosen for expression of a peptide, it may be necessary to take steps to protect the host from the expressed anti-bacterial peptide. Such techniques are known in the art and include the use of a bacterial strain which is resistant to the particular peptide being expressed or the expression of a fusion peptide with sections at one or both ends which disable the antibiotic activity of the peptide according to the invention. In the latter case, the peptide can be cleaved after harvesting to produce the active peptide. If the peptide incorporates a chemical modification then the activity of the expressed peptide may be low, only enhanced to really cytotoxic levels by post-synthetic chemical modification e.g. addition of Pmc.

The present invention also provides pharmaceutical compositions containing the peptides of the invention as defined above together with physiologically acceptable excipients. Suitable diluents and carriers are known to the skilled man. The peptides of the invention for use in methods of treatment, particularly in the treatment of prevention of bacterial infections or as an anti-tumour agent (both in the destruction or reduction in size or number of benign or malignant tumours, which may be ascites and in the prevention of metastasis) constitute further aspects of the present invention.

The compositions according to the invention may be presented, for example, in a form suitable for oral, nasal, parenteral, intravenal, intratumoral or rectal administration.

As used herein, the term "pharmaceutical" includes veterinary applications of the invention.

The compounds according to the invention may be presented in the conventional pharmacological forms of administration, such as tablets, coated tablets, nasal sprays, solutions, emulsions, liposomes, powders, capsules or sustained release forms. The peptides of the invention are particularly suitable for topical administration, e.g. in the treatment of diabetic ulcers. Conventional pharmaceutical excipients as well as the usual methods of production may be employed for the preparation of these forms. Tablets may be produced, for example, by mixing the active ingredient or ingredients with known excipients, such as for example with diluents, such as calcium carbonate, calcium phosphate or lactose, disintegrants such as corn starch or alginic acid, binders such as starch or gelatin, lubricants such as magnesium stearate or talcum, and/or agents for obtaining sustained release, such as carboxypolymethylene, carboxymethyl cellulose, cellulose acetate phthalate, or polyvinylacetate.

The tablets may if desired consist of several layers. Coated tablets may be produced by coating cores, obtained in a similar manner to the tablets, with agents commonly used for tablet coatings, for example, polyvinyl pyrrolidone or shellac, gum arabic, talcum, titanium dioxide or sugar. In order to obtain sustained release or to avoid incompatibilities, the core may consist of several layers too.

The tablet-coat may also consist of several layers in order to obtain sustained release, in which case the excipients mentioned above for tablets may be used.

Organ specific carrier systems may also be used.

Injection solutions may, for example, be produced in the conventional manner, such as by the addition of preservation agents, such as p-hydroxybenzoates, or stabilizers, such as EDTA. The solutions are then filled into injection vials or ampoules.

Nasal sprays which are a preferred method of administration may be formulated similarly in aqueous solution and packed into spray containers either with an aerosol propellant or provided with means for manual compression. Capsules containing one or several active ingredients may be produced, for example, by mixing the active ingredients with inert carriers, such as lactose or sorbitol, and filling the mixture into gelatin capsules.

Suitable suppositories may, for example, be produced by mixing the active ingredient or active ingredient combinations with the conventional carriers envisaged for this purpose, such as natural fats or polyethyleneglycol or derivatives thereof.

Dosage units containing the compounds of this invention preferably contain 0.1–10 mg, for example 1–5 mg of the peptides of the invention. The pharmaceutical compositions may additionally comprise further active ingredients, including other cytotoxic agents such as other antimicrobial peptides. Other active ingredients may include different types of antibiotics, cytokines e.g. IFN-$\gamma$, TNF, CSF and growth factors, immunomodulators, chemotherapeutics e.g. cisplatin or antibodies.

A yet further aspect of the present invention provides the therapeutic use of the peptides of the invention as defined above i.e. the peptides for use as medicaments, e.g. antibacterians or antitumoural agents. Further aspects comprise a method of treating or preventing bacterial infections in a patient comprising the administration to said patient of one or more of the peptides of the invention and a method of treating tumours in a patient comprising the administration of one or more of the peptides of the invention. The treatment of tumours includes the destruction or reduction in size or number of benign or malignant tumours which may be ascites and the preventionn of metastasis.

A still further aspect of the present invention comprises the use of one or more of the peptides of the invention in the manufacture of a medicament for treating bacterial infections or tumours.

Anti-bacterial agents such as the peptides of the present invention have a wide variety of applications other than as pharmaceuticals. They can be used, for example, as sterilising agents for materials susceptible to microbial contamination. The peptides of the invention exhibit broad antimicrobial and antibiotic activity and thus are also suitable as anti-viral and anti-fungal agents which will have pharmaceutical and agricultural applications and as promoters of wound healing or spermicides. All of these uses constitute further aspects of the invention.

The peptides, when used in topical compositions, are generally present in an amount of at least 0.1%, by weight. In most cases, it is not necessary to employ the peptide in an amount greater than 1.0%, by weight.

Anti-tumour peptides may be administered in combination, possibly in synergistic combination with other active agents or forms of therapy, for example administration of a peptide according to the invention may be combined with chemotherapy, immunotherapy, surgery, radiation therapy or with the administration of other anti-tumour peptides.

In employing such compositions systemically (intramuscular, intravenous, intraperitoneal), the active peptide is present in an amount to achieve a serum level of the peptide of at least about 5 ug/ml. In general, the serum level of peptide need not exceed 500 ug/ml. A preferred serum level is about 100 ug/ml. Such serum levels may be achieved by incorporating the peptide in a composition to be administered systemically at a dose of from 1 to about 10 mg/kg. In general, the peptide(s) need not be administered at a dose exceeding 100 mg/kg.

Those peptides exemplified herein represent preferred peptides according to the invention. Any peptide whose specific sequence is disclosed herein, particularly those peptides which are more active against bacterial cells than LFB 17–31, constitute a further aspect of the present invention.

Some of the preferred non-genetic bulky and lipophilic amino acids incorporated into the peptides of the invention include substituted tryptophans which provide an increase in bulk and lipophilicity and a significant increase in bioactivity. Substitutions have been made at the 1-position (or the indole N-position) and the adjacent 2-position and these new compounds, described in Example 2 constitute a still further aspect of the present invention. New 1-substituted tryptophans include 1-benzyl and 1-tosyl tryptophan.

The following novel, 2-substituted Tryptophan residues have been made, Z-Trp (2-nitrophenylsulfenylchloride)-OH and oxides thereof and Z-Trp(2-Pmc)-OH wherein Z is a protecting group, e.g. Fmoc. Method II of Example 2E is a newly devised synthetic route suitable for the preparation of a range of 2-sulfones and constitutes a further aspect of the present invention. Therefore, we further provide a method of preparing tryptophan residues substituted at the 2-position of the indole ring which comprises transferring the group with which the tryptophan will be substituted from a guanidyl containing group to an N-protected tryptophan. Preferably the guanidyl containing group is an arylalkyl or alkyl guanidyl group, most preferably it is a phenylethylguanidyl group. Preferably the N-protecting group is Fmoc and preferably the tryptophan substituting group is Pmc.

LFB 17–41 whose cysteine residues have been blocked by pyridylethylation or acetamido-methylation but incorporate no further bulky and lipophilic amino acids are not per se peptides of the invention. However pharmaceutical compositions comprising these peptides as well as use of the peptides as therapeutic agents as herein described constitute further aspects of the present invention.

The invention will now be described with reference to the following non-limiting examples in which.

FIG. 1 shows the amino acid sequence and charge at pH 7 for synthetic lactoferricins from different species;

Figure 5:
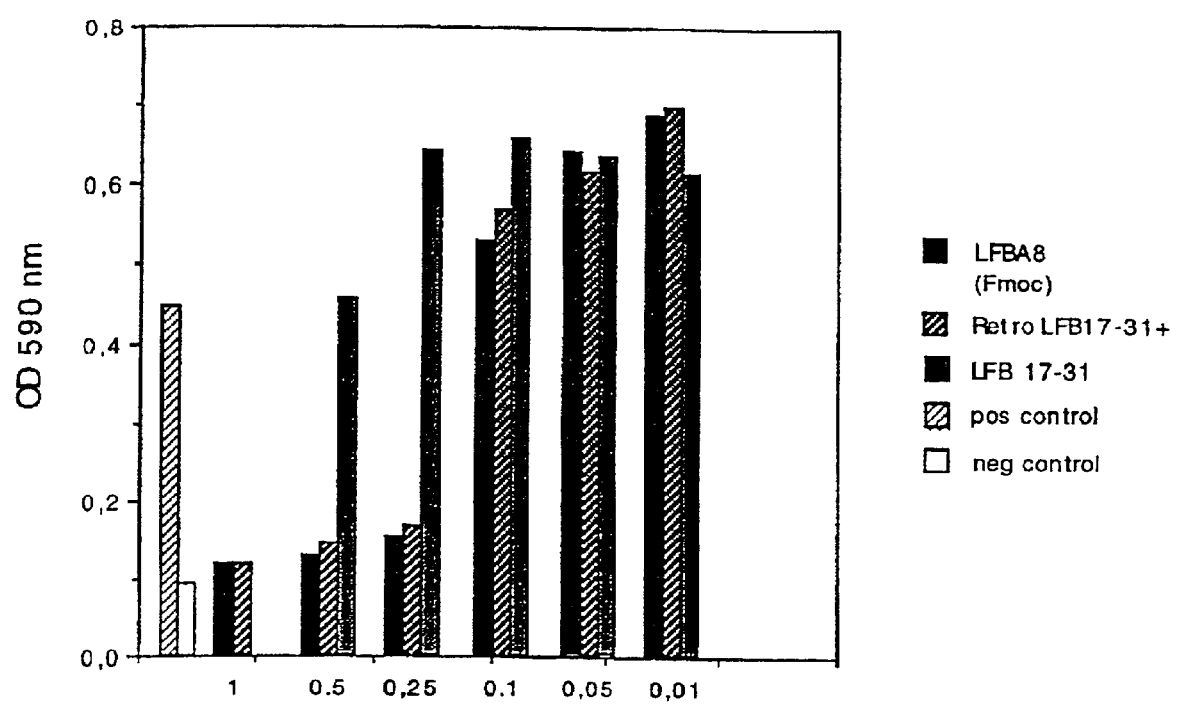
Figure 6:
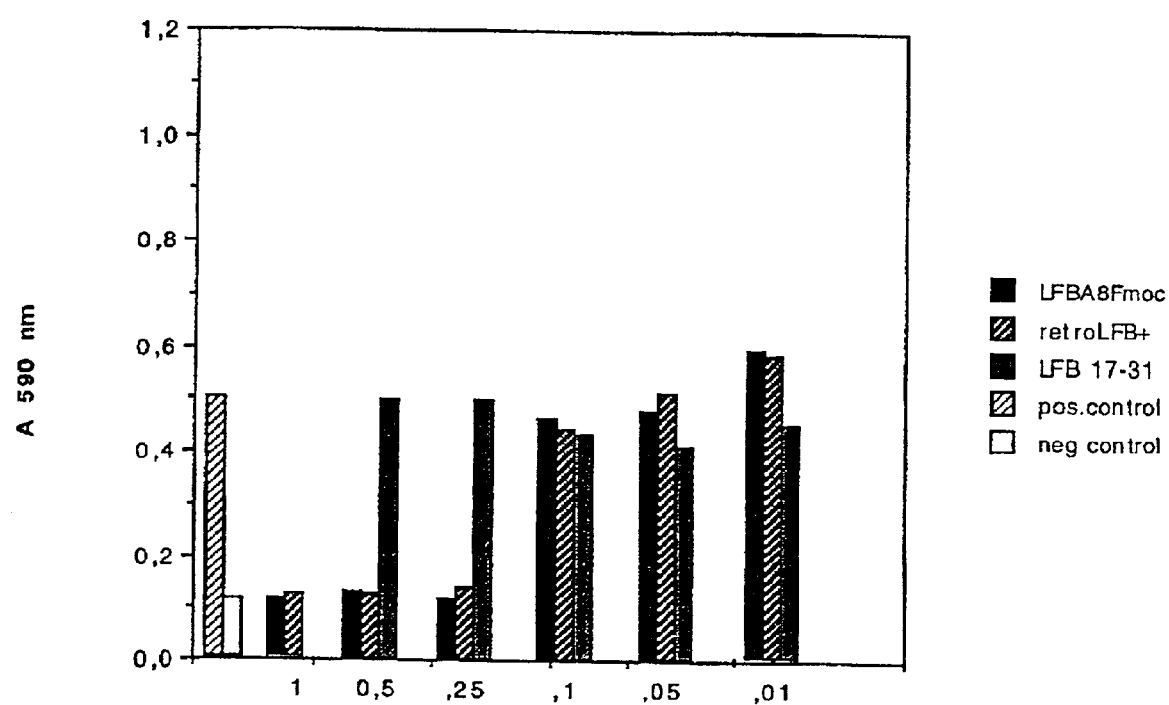
Figure 7:
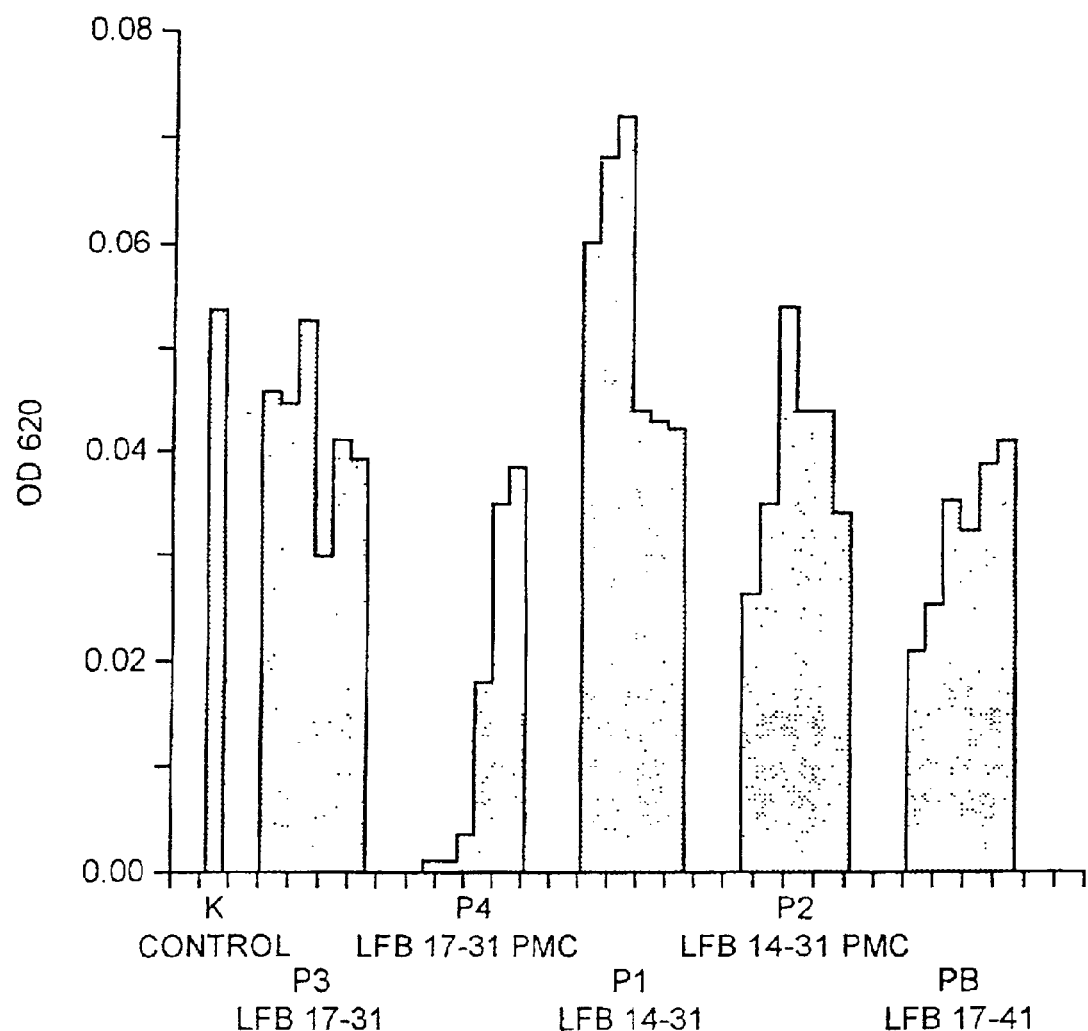
Figure 8:
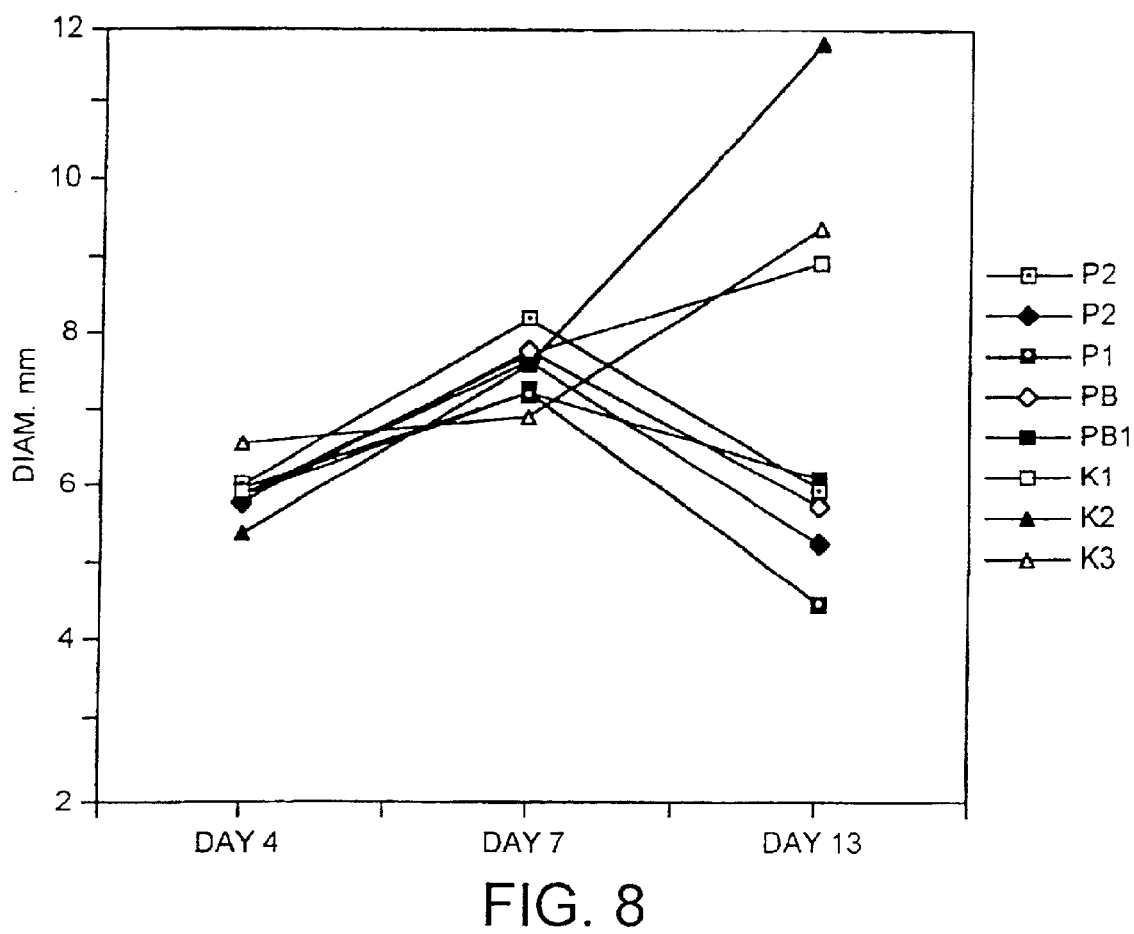
Figure 9:
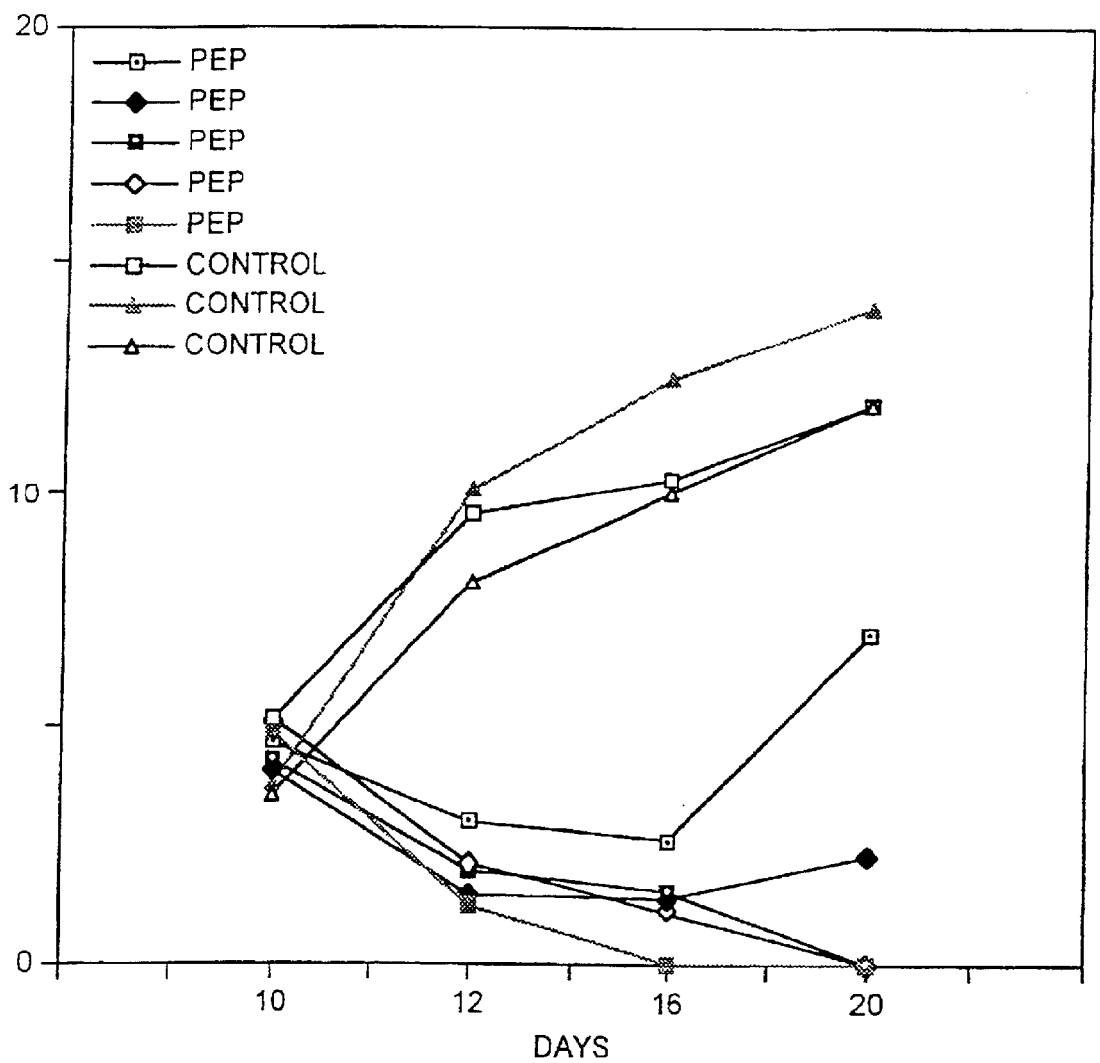
Figure 10:
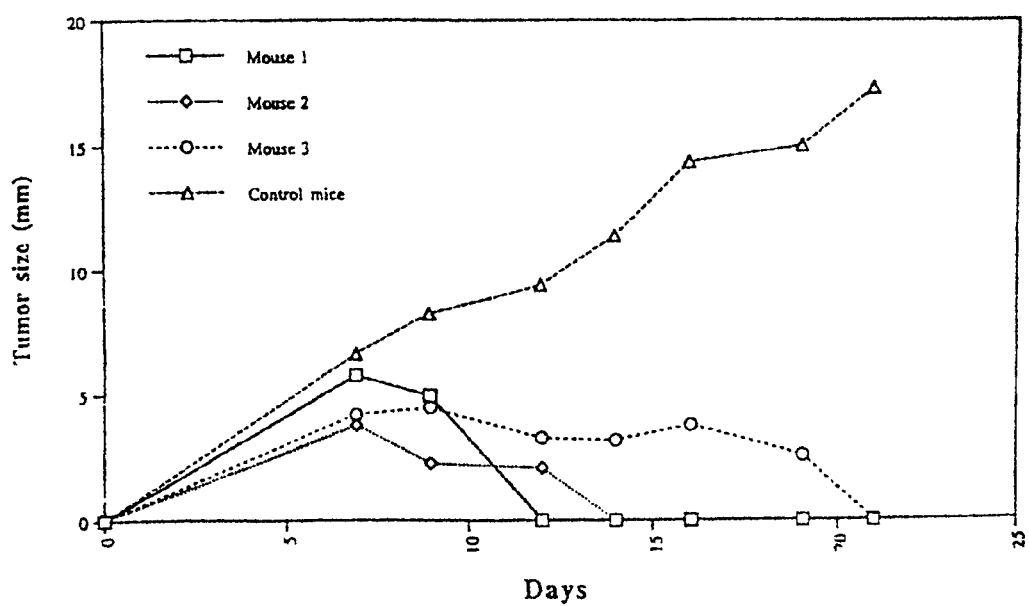

FIG. 5 shows the effects of pmc modified retro LFB 17–31(+), Fmoc LFB 17–31(A8) and LFB 17–31 on Meth A cells in vitro after 4 hour. RPMI was used as negative control and Triton 100× as positive control. Concentrations are in mg/ml;

FIG. 6 shows the effects of pmc modified retro LFB 17–31(+), Fmoc LFB 17–31(A8) and LFB 17–31 on Meth A cells in vitro after 4 hours. RPMI was used as negative control and Triton 100× as positive control. Concentrations are in mg/ml;

FIG. 7 shows the dose response on human promyelotic leukemia cell line HL 60 after 4 hours. HL 60 cells, $1\times10^4$ were incubated with peptides 50, 30, 20, 10, 5, 1 μg, 1000–20 μg/ml in 2 hours and coloured with MTT;

FIG. 8 shows inhibition of tumor growth; Meth A tumor cells ($5\times10^7$ cells) were inoculated on day 1 and treated on day 7 and day 10 with 0.5 mg (1 mg of P1) of the different peptides;

FIG. 9 shows the effect of D-LFB (17–31) A7 Pmc-$NH_2$ on B16F10 murine melanoma;

FIG. 10 shows the size of tumours established in Balb/c mice who are reinoculated with Meth A cells after successful treatment with cLFB. The mice were not treated with cLFB or other peptides in the study, thus some form of adoptive immunity is shown. Reinoculation of Meth A cells 1 month after the LFB-treatment of Meth A tumours.

EXAMPLE 1
Human, Bovine, Murine and Caprine Lactoferrin Derived Peptides
A) MIC (Minimum Inhibitory Concentration) Tests The bacterial strains used were: *Escherichia coli* ATCC 25922 and *Staphylococcus aureus* ATCC 25923. All strains were stored at −70° C. The bacteria were grown in 2% Bacto Peptone water (Difco 1807–17–4). All tests were performed with bacteria in mid-logarithmic growth phase. Determination of the minimum inhibitory concentration (MIC) of the peptides for bacterial strains were performed in 1% Bacto Peptone water. A standard microdilution technique with an inoculum of $2\times10^6$ CFU/ml was used. All assays were performed in triplets. Since the peptides are positively charged and therefore could adhere to the plastic wells, we controlled the actual concentration of the peptides in the solution by HPLC. There was no difference between the concentration of the peptides before or after adding the solution to the plastic wells.
B) Synthesis of Peptides Initially, the lactoferricin B used was a gift from Wayne Bellamy (Nutritional Science Laboratory, Morinaga Milk Industry Co. Ltd, Japan). Later in the study the peptides were synthesised with a 9050 Plus PepSynthesizer (Milligen). All peptides were synthesised on solid phase by use of fluorenylmethoxycarbonyl (Fmoc) chemistry. Cysteines in cystein containing peptides were protected with acetamidomethyl groups to prevent disulfide bridge formation. The peptides were analysed and purified by reversed phase HPLC on a Waters 600E chromatograph (Millipore) with UV detection at 254 nm. The fractions purified on HPLC were analysed on a liquid chromatography-mass spectrometer (LC-MS) with electrospray interface (Fisons VG Quattro) or/and with Fast Atom Bombardment Mass Spectrometry (FAB-MS) (Fisons VG Tribrid).
Structure of the Lactoferricins The structure of human lactoferrin is determined to 2.8 and 2.2 Å resolution by X-ray crystallography. Human lactoferricin (LFH) consists of residues 1–47 of human lactoferricin. LFH contains two peptide fragments; one consisting of residues 12–47 cyclised with a disulfide bridge between Cys20 and Cys37, the second fragment (residues 1–11) is connected to the 12–47 fragment through a disulfide bridge between Cys10 and Cys46. In the human lactoferrin structure, the corresponding residues comprises a β-strand (residues 4–11), an α-helix (residues 12–29), a turn (residues 30 and 31), followed by a β-strand (residues 31–47) [Day, C. L., Anderson, B. F., Tweedie, J. W. and Baker, E. N. (1993) J. Mol. Biol. 232, 1084–1100]. Bovine lactoferricin (LFB) with only 25 residues (residues 17–41) in a single chain is structurally much simpler than LFH.
Antibiotic Activity of Synthetic Lactoferricins with Sequences From Different Species The amino acid sequence of lactoferrins from goat [Provost, F. L., Nocart, M., Guerin, G. and Martin, P. (1994) Biochem. Biophys. Res. Commun. 203, 1324–1332] and mouse [Pentecost, B. T. and Teng, C. T. (1987) J. Biol. Chem. 262 10134–10139] have been determined and show high sequence homology with both the human and the bovine lactoferrins. The residues engaged in the helix-turn-strand motif can easily be identified in the sequence as shown in FIG. 1. As LFB is more antibacterial than LFH, the residues corresponding to LFB (17–41) were chosen in the amino acid sequence of human, murine and caprine lactoferrin to prepare analogous lactoferricin peptides; LFH (18–42), LFM (17–41) and LFC (17–41) respectively. The disulfide bridge is not essential for antibiotic activity in bovine and human lactoferricin [Bellamy et al. (1992)] and all peptides were prepared with ACM protection of the cysteine residues to avoid cyclisation or oxidation.

The antibacterial activities of the synthetic lactoferricins expressed as MIC are compiled in Table 1 which shows that LFB (17–41) displayed the most significant antibacterial activity against *E. coli* and *S. Aureus*.

TABLE 1

Minimum inhibitory concentration (MIC) in μg/ml (μM) of synthetic lactoferricins on *E. coli* ATCC 25922 and *S. aureus* ATCC 25923.

| Peptide | *E. coli* ATCC 25922 MIC | *S. aureus* ATCC 25923 MIC |
|---|---|---|
| LFH (18–42) | >200 | >200 |
| LFB (17–41) | 30 | 30 |
| LFM (17–41) | >200 | >200 |
| LFC (17–31) | 750 | 1000 |
| LFB (14–31) | 70 (28) | 200 (80) |
| LFB (17–31) | 40 (20) | 100 (50) |
| LFB (18–31) | 80 (43) | 200 (108) |
| LFB (19–31) | 200 (120) | >250 (150) |
| LFB (20–31) | 100 (62) | 200 (124) |
| LFB (17–31) K17 | 60 (30) | 100 (50) |
| LFB (17–31) F20 | 20 (10) | 200 (100) |
| LFB (17–31) K17, F20 | 20 (10) | 200 (100) |

LFB analogs with different chain length

A property considered to be important in determining the antibacterial activity of linear peptides, is their ability to adopt helical structures. In the intact lactoferrin protein, residues 14–28 are located in an α-helix, residues 29–31 comprise a turn and residues 32–41 are in a β-strand. We therefore anticipated that the antibacterial effect of the lactoferricins could originate from the part of the sequence that participates in the helix of the intact protein. As the bovine lactoferricin sequence, LFB (17–41), was the only peptide with significant antibacterial property, we chose to prepare a shorter variety of the bovine peptide, LFB (17–31), containing both the helix and turn residues of the protein, while the 10 residues encompassing the strand were removed. Despite the fact that LFB (17–31) has a lower net charge (FIG. 1) than LFB (17–41) and LFC (17–41), it still retains most of the antibacterial effect as shown in Table 1. These findings indicate that even if the overall charge is important, it is not sufficient for antibacterial activity.

EXAMPLE 2

Preparation of Novel Substituted Tryptophans

In the following Examples and throughout the text the following general formula: Z-XX(n-y)-OH refers to a substituted amino acid (XX) wherein the NH$_2$ group of the amino acid is Z-protected, the amino acid is y-substituted at the n position and the COOH group of the amino acid is free.

A) Preparation of Ac-Trp(1-Tos)-OH

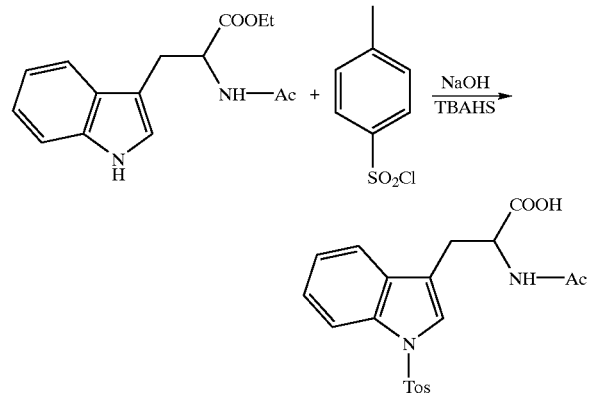

Experimental:

A mixture of Ac-Trp-OEt (0.19 g, 0.69 mmol), tosyl chloride (0.20 g, 1.04 mmol), tetrabutylammonium hydrogensulfate (2 mg, 0.01 equiv.) and NaOH (0.07 g, 1.73 mmol) in dichloromethane was stirred at room temperature for 2.5 hours. To the reaction mixture was added diluted HCl until a pH of 2–3 was reached and then washed with water. To the organic phase was added a diluted base and the aqueous phase was extracted with dichloromethane, acidified and again extracted with dichloromethane.

$^1$H NMR (CDCl$_3$): δ 1.89 (s, 3H), 2.24 (s, 3H), 3.1–3.35 (m, 2H), 4.87 (m, 1H), 6.63 (d, 1H), 7.1–7.3 (m, 4H), 7.46 (m, 2H), 7.68 (d, 2H), 7.89 (d, 1H), 9.34 (s, broad, 1H). MS (EI): m/z 382(10%), 284(84%), 157(8%), 155(61%), 130 (26%), 129(24%).

| Materials: | |
|---|---|
| Ac-Trp-OEt | Prepared according to procedure described under <<Peparation of diacetyltryptophan ethyl ester>>, Bodanszky, M and Bodanszky A, The Practice of Peptide Synthesis (1994) p 30; Vogel's Textbook of Practical Organic Chemistry 5th Ed. (1989) p. 1273. |

B) Preparation of Fmoc-Trp(1-Benzyl)-OH

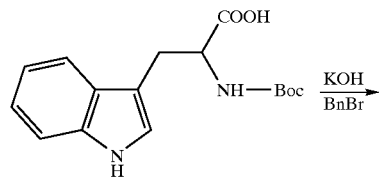

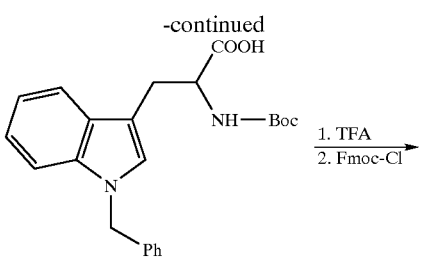

Boc-Trp(1-Benzyl)-OH$^1$:

Dimethyl sulfoxide (7 ml) was added to potassium hydroxide (0.73 g, 13 mmol) (crushed pellets) and the mixture was stirred for 5 min. Boc-Trp-OH (1 g, 3.3 mmol) was then added and the mixture stirred for 1 hour. Benzyl bromide (1.13 g, 6.6 mmol) was added and the mixture cooled briefly and stirred for a further 20 hours before water (20 ml) was added. The mixture was extracted with diethyl ether (3×20 ml). The pH of the combined aqueous phases was adjusted to 2–3 by addition of 1M HCl (20 ml) and extracted with diethyl ether (3×20 ml). Each extract was washed with water (3×20 ml). The combined diethyl ether phases were dried with MgSO$_4$ and the solvent removed under reduced pressure. The product was isolated as white crystals (0.89 g, 2.3 mmol). Yield 69%.

$^1$H NMR (CDCl$_3$): δ 1.41 (s, 9H), 3.33 (m, 2H), 4.64 (m, 1H), 5.02 (m, 1H), 5.24 (s, 2H), 6.95 (s, 1H), 7.01–7.38 (m, 8H), 7.59 (d, J=7.7 Hz, 1H).

H-Trp(1-Benzyl)-OH:

Boc-Trp(1-Bn)-OH was dissolved in 98% TFA and stirred for 3 hours at room temperature. Then the solvent was removed under reduced pressure. The product was isolated as an oil and used without further purification.

Fmoc-Trp(1-Benzyl)-OH:

H-Trp(1-Bn)-OH (1.90 g, 6.5 mmol) was dissolved in a 10% solutin of Na$_2$CO$_3$ in water (21 ml, 20 mmol). Dioxane (15 ml) was added and the mixture was stirred in an ice-water bath. 9-Fluorenylmethyl chlorocarbonate (1.69 g, 6.5 mmol) was added in small portions and stirring was continued at ice-water bath temperature for 4 hours and then at room temperature for 8 hours. The reaction mixture was poured into water (400 ml) and extracted with ether (3×200 ml). The combined ether phases were dried with MgSO$_4$ and the solvent removed under reduced pressure. The product was purified by chromatography on silica gel in solvent A (Solvent A=Ethylacetate: Methanol=4:1). After purification the product was obtained as a white crystalline compound. The yield was 2.429 (72%).

$^1$H NMR (400 MHz, CDCl$_3$): δ 3.34 (m, 2H) 4.18 (m, 1H) 4.37 (m, 2H), 4.78 (s, 1H), 5.19 (s, 2H), 5.31 (d, 1H), 6.91–7.74 (m, 19H).

| Materials: | |
|---|---|
| Boc-Trp-OH | BACHEM no A-2360 |
| Fmoc-ONSu | Fluka no 46920 |
| Trifluoroacetic acid | Fluka no 91700/KEBO no 1.8341-100 |

Reference 1: Heaney, H., and Ley, S. V. J. Chem. Soc. Perkin 1. (1973) 499–500

C) Preparation of Fmoc-Trp(2-Nps)-OH

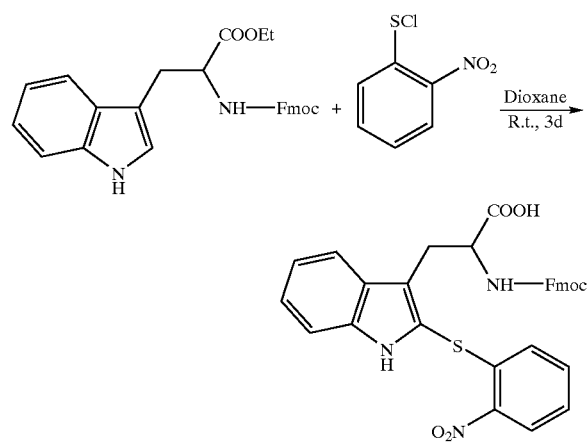

To a solution of 2.0 g (4.7 mmole) Fmoc-L-tryptophan in 12 ml dioxane, 0.87 g (4.6 mmole) of 2-nitrophenyl-sulfenylchloride (2-Nps-Cl) in 25 ml dioxane was added under stirring at room temperature. After standing for 3 days, 50 ml ethyl ether was added to the reaction mixture and the solvent was evaporated. The product was purified by chromatography on silica gel in solvent A (Solvent A=Chloroform: Ethanol:Neptane—1:1:1). $R_f$ 0.43. After purification the product was obtained as a yellow-brown crystalline compound. The yield was 2.5 g (89%).

HPLC (C18): $t_R$ 8.3 min, 85–100% B in 20 min. (A:$H_2O$+ 0.1% TFA; B:$CH_3CN$+0.1% TFA).

$^1$H NMR (DMSO-$d_6$): δ 3.16 (m, 1H), 3.38 (m, 1H), 4.00–4.10 (m, 3H), 4.19 (m, 1H), 6.72 (d, J=8.1 Hz, 1H), 7.03 (t, J=7.3 Hz, 1H), 7.18 (t, 1H), 7.22–7.49 (m, 7H), 7.60 (dd, J=7.3 and 12.1 Hz, 2H), 7.86 (m, 3H), 8.24 (d, J=8.1 Hz, 1H), 11.51 (s, 1H)

After incorporation of Fmoc-Trp(2-Nps)-OH into a peptide, MS electrospray analysis confirmed the expected molecular weight.

| Materials: | |
|---|---|
| Fmoc-Trp-OH | BACHEM No B-1445/ SENN No 02019 |
| 2-Nitrophenylsulfenyl chloride | Fluka No 73740 |

D) Oxidation of Fmoc-Trp(2-Nps)-OH

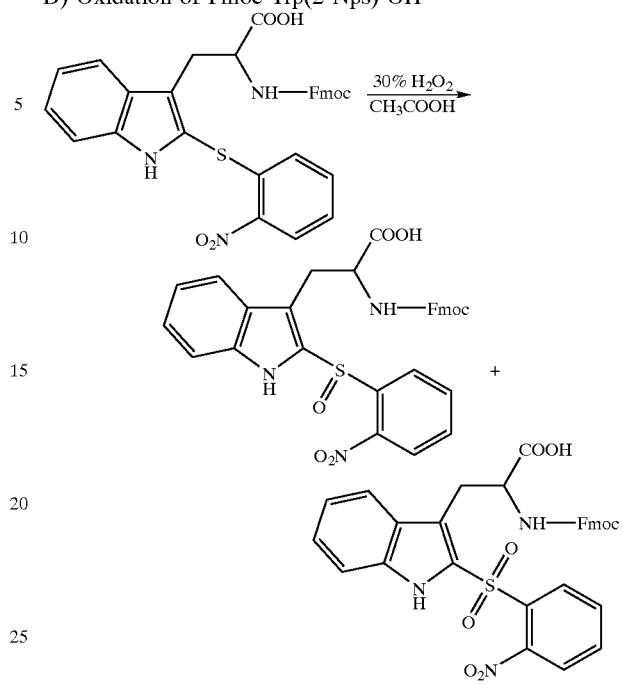

To a solution of 1.12 g (1.9 mmol) Fmoc-Trp(2-Nps)-OH in 15 ml glacial acetic acid, was added 12 ml 30% $H_2O_2$ under stirring at room temperature. The reaction mixture was heated for 2 hours at 65° C. The precipitate was collected, added water and lyophilised. The yield was 0.59 g (52%). The product was obtained as a yellow crystalline compound.

HPLC (C18): $t_R$ 6.4 min, 85–100% B in 20 min. (A:$H_2O$+ 0.1% TFA; B:$CH_3CN$+0.1% TFA).

$^1$H NMR (DMSO-$d_6$): δ 3.25 (dd, J=9.0 and 14.5 Hz, 0.5H), 3.54 (m, 1H), 3.77 (dd, J=5.9 and 14.3 Hz, 0.5H), 4.01–4.26 (m, 3H), 4.32 (m, 0.5H), 4.40 (m, 0.5H), 7.00–7.98 (m, 15H), 8.23 (m, 1H), 8.35 (m, 1H), 8.56 (d, J=8.1 Hz, 1H), 11.08 (s, 0.5H), 11.17 (s, 0.5H).

After incorporation of Fmoc-Trp(2-NpsO$_2$)-OH into a peptide, MS electrospray analysis revealed that the oxidation of Fmoc-Trp(2-Nps)-OH had been incomplete; the product was a circa 3:1 mixture of the sulfoxide Fmoc-Trp (2-NpsO)-OH and the sulfone Fmoc-Trp(2-NpsO$_2$)-OH. Proton NMR indicates a 1:1 mixture of the two compounds based on double sets of signals for β-, α- and carboxyl-protons.

E) Preparation of Fmoc-Trp(2-Pmc)-OH

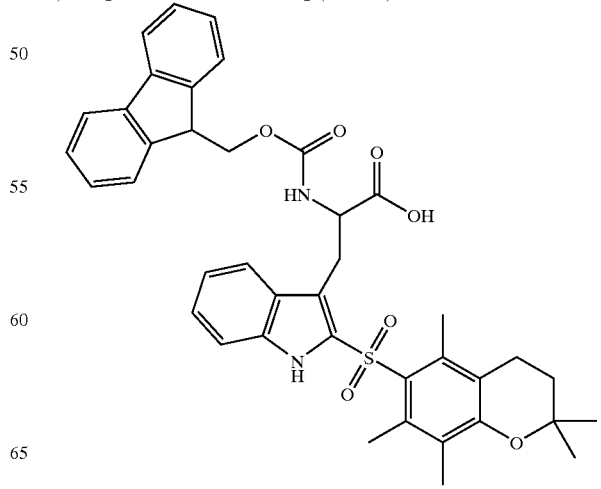

Method I: By Transferral of the Pmc-Group from Fmoc-Arg(Pmc)-OH

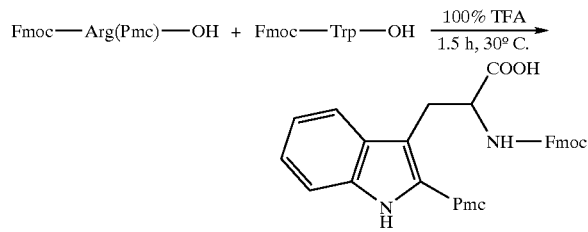

Fmoc-Arg(Pmc)-OH (0.5 g, 0.75 mmol) and Fmoc-Trp-OH (0.43 g, 0.1 mmol) was dissolved in 10 ml 100% TFA and heated at 30° C. for 1.5 hours. After evaporation of TFA, Fmoc-Arg-OH was removed by column chromatography on silica gel with heptane/ethyl acetate 2:1 as mobile phase. Fmoc-Trp(2Pmc)-OH was isolated by preparative HPLC (C18, 70–100% B in 15 min., $t_R$ 14.8 min, (A: $H_2O$+0.1% TFA; B: $CH_3CN$ +0.1% TFA)). Isolated yield 130 mg (0.19 mmol, 25%).

$^1$N NMR (400 MHz, CDCl$_3$): δ 1.30 (s, 6H), 1.79 (t, 2H), 2.07 (s, 3H), 2.43 (s, 3H), 2.48 (s, 3H), 2.59 (t, 2H), 3.03 (m, 1H), 3.25 (m, 1H), 4.1–4.3 (m, 3H), 4.42 (m, 1H), 6.53 (d, 1H), 7.15–7.78 (m, 12H), 8.90 (s, 1H)

| Materials: | |
|---|---|
| Fmoc-Arg(Pmc)-OH | BACHEM no B-1670 |
| Fmoc-Trp-OH | BACHEM no B-1445/SENN no 02019 |
| Trifluoroacetic acid | KEBO no 1.8341-100/Fluka no 91700 |

Method II: By Transferral of the Pmc-Group from Phenylethylguanidyl-Pmc

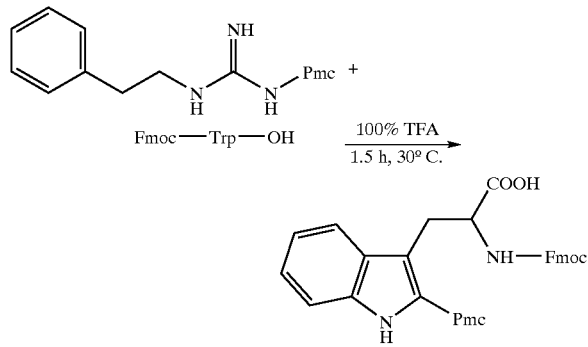

2,2,5,7,8-Pentamethylchroman:

References:

Robert Ramage, Jeremy Green and Alexander J. Blake, *Terahedron* Vol. 47, No. 32, pp. 6353–6370, 1991.

Reaction:

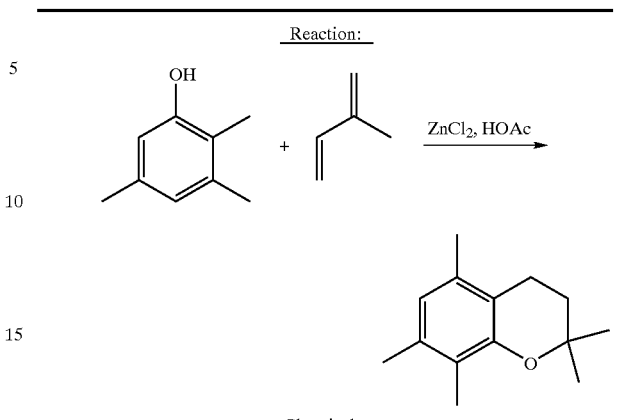

Chemicals:

| Substance | Quantity | MW | mmoles | eqv. | Source |
|---|---|---|---|---|---|
| 2,3,5-Trimethylphenol | 50.03 g | 136.20 | 367.33 | 1.0 | Fluka |
| Isoprene | 25.09 g | 68.12 | 368.32 | 1.0 | Jannsen Chimica |
| ZnCl$_2$ | 5.94 g | 136.29 | 43.58 | 0.12 | Fluka |
| Acetic acid | 47 ml | — | — | — | KEBO lab |

Procedure:

2,3,5-Trimethylphenol (50.03 g, 0.367 moles), isoprene (25.09 g, 0.368 moles) and fused zinc chloride (5.94 g, 0.044 moles) was stirred with anhydrous acetic acid (47 ml) for 14 hours at room temperature. The cloudy red coloured mixture was then gradually heated and it became clear. Upon refluxing the reaction mixture turned black, and after 8 hours of reflux it was cooled to room temperature. The reaction mixture was poured into 250 ml water and the black oil separated. The water was extracted with pentane (3×200 ml) and the combined organic phases washed with Claisen's alkali (2×150 ml), water (3×250 ml) and brine (2×200 ml), dried over CaCl$_2$ and evaporated to a brown oil under reduced pressure. The crude product was distilled at 0.48 mBar affording the product as a pale yellow liquid (36.90 g, 49% yield); b.p. 82–96° C. (0.48 mBar); >95% pure (GC).

Results:

The product was isolated as a pale yellow liquid which solidified upon cooling in 49% yield.

$^1$H NMR (CDCl$_3$, 400 MHz): δ=1.30 (6H,s, 2×CH$_3$), 1.78 (2H, t, J=7 Hz, CH$_2$), 2.07 (3H, s, CH$_3$), 2.15 (3H, s, CH$_3$), 2.19 (3H, s, CH$_3$), 2.59 (2H, t, J 7 Hz, CH$_2$), 6.54 (1H, s, aromatic H).

$^{13}$C NMR (CDCl$_3$, 400 MHz): δ=11.42 (CH$_3$), 18.91 (CH$_3$), 19.84 (CH$_3$), 20.49 (CH$_2$), 26.97 (2×CH$_3$), 32.79 (CH$_2$), 73.10 (C(CH$_3$)$_2$), 116.67 (Ar—C), 122.03 (Ar—C), 122.29 (Ar—C), 133.44 (Ar—C), 134.70 (Ar—C), 151.72 (Ar—C). MS (GC/MS): m/z=204(100), 189(14), 149(91).

2,2,5,7,8-Pentamethylchroman-6-sulfonyl Chloride:

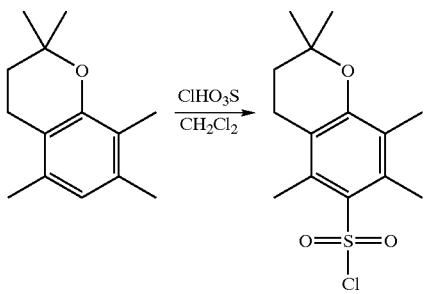

To a solution of 2,2,5,7,8-pentamethylchroman (3.39 g, 16.6 mmol) in 30 ml dichloromethane at −8° C. was added under stirring chlorosulfonic acid (3.98 g, 34.2 mmol) in 30 ml dichloromethane within 3 minutes. The mixture was stirred at −8° C. for 15 minutes and at room temperature for 2.5 hours. The reaction mixture was carefully shaken with 50 ml dichloromethane and 100 ml ice a couple of times and the phases separated. The crude product contained circa 16% of starting material as judged by $^1$H NMR. When hot pentane was added to the crude product, a dark oil was formed which was removed by decanting. The product was then isolated by crystallisation from pentane as a light brown powder (2.80 g, 9.3 mmol). Yield 56%.

$^1$H NMR (CDCl$_3$) δ 1.34 (s, 6H), 1.85 (t, J=7.0 Hz, 2H) 2.14 (s, 3H), 2.60 (s, 3H), 2.62 (s, 3H), 2.68 (t, J=7.0 Hz, 2H).

2-Phenylethylquanidine Hemisulfate:

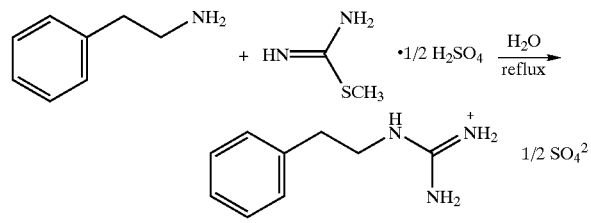

2-Phenylethylamine (8.49 g, 70.1 mmol) and S-methylisothiourea sulfate (9.43 g, 33.9 mmol) was dissolved in 100 ml destilled water. Air was passed over the reaction mixture and through 50% NaOH (500 ml) and then through 5% cuprous sulfate (250 ml). The reaction mixture was heated at reflux for 5 hours. Evaporation of the solvent yielded a white powder. The product was isolated by crystallisation from 96% ethanol, washed with cold acetone and diethyl ether and dried in a desicator. After three crystallisations, the product contained only minor amounts of starting material. The reaction yielded 61.5% (9.14 g) 2-phenylethylguanidine hemisulfate.

$^1$H NMR (D$_2$O): δ 2.87 (t, J=6.6 Hz, 2H), 3.44 (t, J=6.6 z, 2H), 7.24–7.38 (m, 5H)

Phenylethylguanidyl—Pmc:

Reaction: Ian Michael Eggleston, Ph.D. thesis, University of Oxford, 1990.

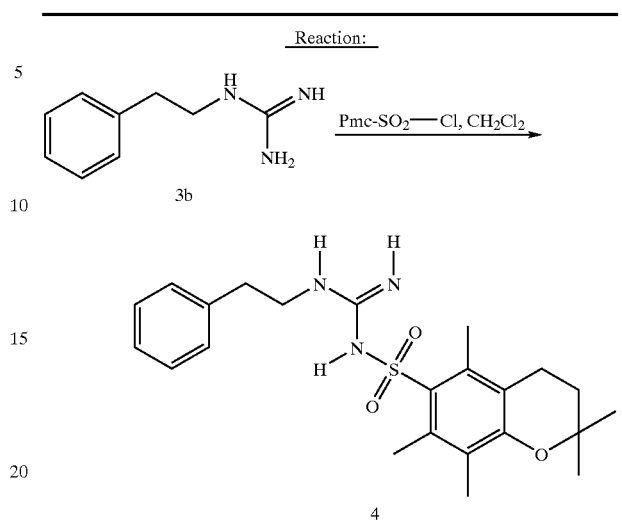

Chemicals:

| Substance | Quantity | MW | mmoles | eqv. | Source |
|---|---|---|---|---|---|
| 2-Phenylethyl-guanidine hemisulfate | 7.40 g | 212.24 | 34.87 | 1.5 | B11-01 |
| Pmc-SO$_2$—Cl | 7.00 g | 302.07 | 23.17 | 1.0 | B15-02 |
| CH$_2$Cl$_2$ | 150 ml | — | — | — | KEBO lab |

Procedure:

2-Phenylethylguanidine hemisulfate (3) (7.40 g, 34.87 mmoles) was suspended in 6M NaOH (80 ml) and extracted into chloroform (2×80 ml). After evaporation of the solvent in vacuo the oily residue was co-evaporated with benzene (2×10 ml). The free guanidine (3 b) was dissolved in 75 ml dichloromethane in a 250 ml round bottomed flask equipped with a magnetic stirring bar and a 100 ml addition funnel with pressure equaliser. The funnel was charged with Pmc-SO$_2$—Cl (7.00 g, 23.17 mmoles) dissolved in 75 ml dichloromethane. The equipment was flushed with nitrogen, and the reaction was performed under a weak nitrogen flow. The round bottomed flask was cooled in an ice/water bath, and the Pmc-SO$_2$Cl solution added over a period of 20–25 minutes. The reaction mixture was allowed to attain room temperature overnight. The dichloromethane was evaporated in vacuo and the residue partitioned between water (100 ml) and ethyl acetate (120 ml). The organic layer was then washed with water (100 ml). Upon cooling of the ethyl acetate the product appeared as a white/pale yellow powder, which was filtered off and dried in vacuo.

Results:

3.32 g of a pale yellow powder was isolated. The yield of the reaction is 33%. Melting point: 145–147° C.

$^1$H NMR (CDCl$_3$): δ=1.30 (6H, s, 2×CH$_3$) 1.80 (2H, t J 7.0 Hz, CH$_2$), 2.09 (3H, s, CH$_3$), 2.51 (3H, s, CH$_3$), 2.52 (3H, s, CH$_3$), 2.61 (2H, t J 6.6 Hz, CH$_2$), 2.81 (2H, t J 7.0 Hz, CH$_2$), 3.43 (2H, m, CH$_2$), 6.21 (3H, broad s, 3×NH), 7.12–7.25 (5H, m, aromatic protons).

MS: m/z=429(6), 204 (37), 149(100), 105(24), 92 (37).
Fmoc-Trp (2-Pmc)-OH:

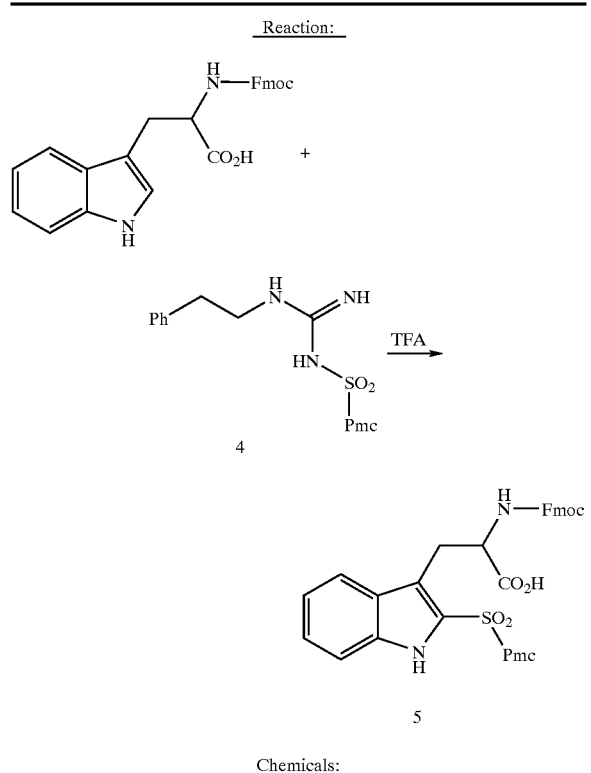

Reaction:

| Substance | Quantity | MW | mmoles | eqv. | Source |
|---|---|---|---|---|---|
| Fmoc-Trp-OH | 4.14 g | 426.49 | 9.71 | 1.0 | SENN |
| $N^G$-(6-SO$_2$-Pmc)-2-phenylethylguanidine | 2.08 g | 429.59 | 4.84 | 1.0 | BEH-B17 |
| Trifluoroacetic acid | 25 ml | — | — | — | Fluka |

Procedure:

$N^G$-(6-SO$_2$-Pmc)-2-phenylethylguanidine (2.08 g, 4.84 mmoles) and Fmoc-Trp-OH (4.149, 9.71 mmoles) was stirred with trifluoroacetic acid (25 ml) at room temperature for 2 hours. The reaction mixture was then evaporated in vacuo and the residue partitioned between chloroform and 1 M hydrochloric acid. By cooling of the chloroform solution the excess of Fmoc-Trp-OH could be removed by filtration.

The product was purified by flash chromatography (ethyl acetate/heptane, 1:1).

Results:
The title compound was isolated as a white powder in 26% yield.

Materials:

| Chlorosulfonic acid | Fluka no 26388 |
|---|---|
| Phenylethylamine | Fluka no 77900 |
| S-Methylisothiourea sulfate | Fluka no 67730 |
| Fmoc-Trp-OH | BACHEM no B-1445/ SENN no 02019 |
| Trifluoroacetic acid | KEBO no 1.8341-100/ Fluka no 91700 |

F) Preparation of Fmoc-2,5,7-tritertbutyltryptophan
2,5,7-tritertbutyltryptophan Tryptophan (4.00 g, 19.59 mmol), trifluoroacetic acid 98% (60 ml) and tert-butanol (15.54 g, 209.66 mmol) were mixed. The reaction mixture was stirred at room temperature for 48 hours. The trifluoroacetic acid was evaporated. The residue was suspended in 40 ml distilled water, and the pH adjusted to neutral with addition of sodium hydrogen carbonate. The crude product was obtained by filtration. Crystallisation from 50% ethanol affored the product as a white powder (85–90% pure).

$^1$H NMR (CDCl$_3$): δ=1.34 (9H, s, 3 CH$_3$), 1.46 (9H, s, 3 CH$_3$), 1.49 (9H, s, 3CH$_3$), 7.45 (1H, s, CH arom), 7.18 (1H, S, CH arom), 5.29 (1H, s, NH).

Fmoc-2,5,7-tritertbutyltryptophan:
The title compound was prepared as described for Fmoc-Trp(1-benzyl)-OH.

EXAMPLE 3

Bioactivity of Lactoferricin Analogs
Synthesis of the Analogs

All the peptides were synthesized on a 9050 Millipore Automatic Peptide Synthesizer using Fmoc protection and activation with pentafluorophenyl (Pfp)esters or in situ activation with the coupling reagent HATU (O-(7-azabenzotriazol-1-yl)-1,1,3,3-tetramethyl uronium hexafluorophosphate). In the case of coupling with pentafluorophenyl esters, 1-HOBt (1-hydroxy-benzotriazole) was added to catalyse the reaction, and when using the coupling reagent HATU the reaction was base catalysed with DIPEA (diisopropylethylamine). All amino acids with reactive side chains were protected with acid labile protecting groups and cleaved upon treatment with TFA (trifluoroacetic acid) containing scavengers. (See below for scavenger mixture). At the same time the peptides were cleaved from the solid support on treatment with the TFA solution.

A) Attachment of the First Amino Acid to the Solid Support when Synthesizing All D-Peptides The solid support PAC-PEG-PS (Peptide Acid—Poly Ethylene Glycol—Poly Styrene resin) (1 eq.) was mixed together with Fmoc-D-amino acid-OPfp (5 eq.) and DMAP (dimethylaminopyridine) (1 eq.) in a small volume of DMF (dimethylformamide) and left to swell for 30 minutes. The solution was then stirred slowly for 4½ hours. Ac$_2$O (acetic acid anhydride) (2.5 eq.) and DMAP (0.1 eq.) were then added to the solution in order to acetylate any remaining hydroxyl groups on the solid support. The solution was then stirred for another hour. The solid support with the C-terminai amino acid attached was isolated by filtration and washed several times on the filter with DMF. The solid support was then used in the synthesis of the target peptide on the 9050 Millipore Automatic Peptide Synthesizer.

B) Acetylation of the N-Terminal H$_2$N-Group using Acetic Acid Anhydride

The peptide-resin complex was dissolved in a small volume of DMF and treated with an excess of acetic acid anhydride (20 eq.) and DMAP (5 eq.) for four hours while slowly stirring the solution with a small magnet. Complete acetylation was verified by a ninhydrin test/Kaiser's test (see below).

C) Ninhydrin Test/Kaiser's Test

Less than 1 mg of the peptide-resin complex was treated with small equal volumes of a 5% ninhydrin solution in ethanol, a solution of 80 g phenol in 20 ml ethanol and a solution of dried, distilled pyridine. The reaction mixture was heated for two minutes at 110° C., and investigated under a microscope. (In this test a yellow reaction mixture indicates successful acetylation, while a blue solution indicates still free amino groups.)

D) Cleavage of Acid Labile Protecting Groups

Cleavage of acid labile protection groups and cleavage of the peptides from the solid support was achieved using a mixture of 2% anisol, 2% ethandithiol (EDT), 2% water and 2% phenol in TFA, and with cleavage times of no more than four hours. The solid support was then removed by filtration and the peptide precipitated in diethyl ether. The ether solution containing TFA was removed using a pasteur pipette, and the peptide was washed several times with diethylether and dried under high vacuum.

E) Purification

The peptides were purified by HPLC using a C18-reversed phase column (*) and a mixture of water and acetonitrile (both added 0.1% TFA) as mobile phase. Selected wavelength for detection of peptide fractions was 254 nm.

(*) PrePak®Cartridge 25×100 mm. DeltaPak™ C18 15 μm 100 Å. (Waters Corporation.)

F) Analysis

All peptides were analysed for impurities on an analytical HPLC C18-reversed phase column using a mixture of water and acetonitrile (both added 0.1% TFA) as mobile phase. The molecular weight of the peptides were determined by positive ion electrospray ionization mass spectrometry (VG Quattro Quadrupole)

Amino Acid Derivatives used in Synthesis of Both L- and D-Analogs of Lactoferricin

| | |
|---|---|
| Fmoc-AlaPEG-PS (solid support) | Fmoc-Lys(tBoc)-OPfp |
| Fmoc-Arg(Pbf)-OH | Fmoc-Met-OPfp |
| Fmoc-Arg(Pmc)-OH | Fmoc-β-(2-naphthyl)-alanine-OH |
| Fmoc-Asn(Trt)-OPfp | Fmoc-Phe-OPfp |
| Fmoc-Cys(Acm)-OPfp | Fmoc-Ser(tBu)-OPfp |
| Fmoc-Gln-OPfp | Fmoc-Thr(tBu)-OPfp |
| Fmoc-Glu(OtBu)-OPfp | Fmoc-Trp-OPfp |
| Fmoc-Gly-OPfpFmoc-Tyr(tBu)-OPfp | Fmoc-Leu-OPfp |

Amino acid derivatives were purchased from either Bachem, MilliGen/Biosearch (Division of Millipore) or PerSeptive Biosystems.

Antimicrobial Activity of Alanine Scan Peptides Containing a Tryptophan-Pmc Residue During deprotection of acid labile protecting groups and cleavage of the peptide from the resin with trifluoro acetic acid, a side reaction involving transfer of the Pmc (2,2,5,7, 8-pentamethylchroman-6-sulphonyl group) protecting group from arginine to the second position of the indole of tryptophan was observed. Isolation of these byproducts have been done, and the results from MIC analyses are given in Table 2. This table also shows the results of an alanine scan performed on LFB with no Pmc groups.

During an alanine scan, a series of peptides are produced wherein successive amino acids have been substituted by alanine.

The sequence of native bovine lactofericin from amino acids 17 to 31 (LFB 17–31) is $H_2N$-Phe-Lys-Cys-Arg-Arg-Trp-Gln-Trp-Arg-Met-Lys-Lys-Leu-Gly-Ala-COOH (SEQ ID No. 1).

TABLE 2

MIC results for alanine scan peptides with a Pmc group attached to one of the two tryptophan residues. Results also shown for an alanine scan performed on LFB with no Pmc groups.

| | Pmc | | Without Pmc | |
|---|---|---|---|---|
| Peptide | MIC E. coli | MIC S. aureus | MIC E. coli | MIC S. aureus |
| LFBA 1 | 8.75 | 10 | 70 | >200 |
| LFBA 2 | 11.25 | 10 | 80 | >200 |
| LFBA 3 | 7.5 | 7.5 | 25 | 100 |
| LFBA 4 | 15 | 27.5 | 70 | >200 |
| LFBA 5 | 10 | 50(*) | 120 | >200 |
| LFBA 6 | 25 | 17.5 | >200 | >200 |
| LFBA 7 | 20 | 7.5 | 30 | 150 |
| LFBA 8 | 15 | 17.5 | >200 | >200 |
| LFBA 9 | 10 | 12.5 | 55 | >200 |
| LFBA 10 | 20 | 22.5 | 140 | >200 |
| LFBA 11 | 22.5 | 22.5 | 70 | >200 |
| LFBA 12 | 20 | 20 | 50 | >200 |
| LFBA 13 | 15 | 15 | 50 | >200 |
| LFBA 14 | 15 | 17.5 | 25 | 160 |
| LFBA 17–31 | 10 | 10 | 50 | 100 |

(*)MIC of 25 has been observed

The results show that a Pmc group attached to one of the tryptophan residues increases the activity four times for E. coli. Even more marked is the effect on S. aureus. This gram positive bacteria was found to be nearly totally resistant to all the alanine scan analogs, but shows now a MIC between 10 and 22.5 μg/ml. This represents a ten fold increase in antibacterial activity relative to native LEB 17–31. The tryptophan-Pmc residue, which is hydrophobic, seems therefore to increase the peptide; affinity for the hydrophobic parts of the bacterial cell membrane to such an extent that the antibacterial activity of the peptide is no longer so sequence dependent as for the peptide without this residue. Comparison of Antimicrobial Activity Between Native Bovine Lactoferricin (LFB 17–31) and Enantio-, Retro- and Retro-Enantio LFB 17–31 and these Same Peptides Incorporating a Tryptophan-Pmc Residue Peptides containing a Pmc-group transferred from an arginine residue to a tryptophan residue was also isolated after synthesis of Enantio-, Retro- and Retro-Enatio LFB 17–31.

TABLE 3

MIC results for native bovine lactoferricin (LFB 17–31), Enantio-, Retro- and Retro-Enantio LFB 17–31 and for these peptides with a Pmc group attached to one of the two tryptophan residues.

| Peptide | MIC E. coli | MIC S. aureus | % Hemolysis 10 μg/ml |
|---|---|---|---|
| Native LFB 17–31 | 50 | 100 | 2.6 |
| Enantio LFB 17–31 | 7.5 | 60 | 3.05 |
| Retro LFB 17–31 | 80 | 200 | 2.01 |
| Retro-Enantio LFB 17–31 | 6.25 | 80 | 3.31 |
| LFB 17–31 Pmc | 10 | 10 | 2.8 |
| Enantio LFB 17–31 Pmc | 7.5(*) | 100 | 3.17 |
| Retro LFB 17–31 Pmc | 10 | 10 | 2.5 |
| Retro-Enantio LFB 17–31 Pmc | 7.5 | 12.5 | 5.28 |

(*)MIC of less than 5 has been observed.

The Enantio peptide, which is the exact mirror image of the native peptide, shows remarkable improvements in antibacterial activity. (In fact, this peptide shows the same activity as the native peptide LFB 17–31 with a tryptophan- Pmc residue, in the case of *E. coli*.) Configurationally this means that an all-D-amino acid analog of LFB 17–31 interacts better with the chiral phospholipids of the bacterial cell membrane than the native all-L-amino acid peptide LFB 17–31. It may also imply that this Enantio peptide is more resistant to degradable proteases of the bacteria.

The Retro peptide, with an inverted sequence in respect to LFB 17–31, shows no improvements in antibacterial activity, which is consistent with the theory of the antibacterial activity of LFB 17–31 being sequence specific. This peptide is not really an isomer of bovine lactoferricin since the amino acid sequence is totally different. The low antibacterial activity of this peptide does therefor not come as any surprise.

A remarkably high antibacterial activity against *E. coli* was observed for the Retro-Enantio peptide which, as already mentioned, adopts the same a-helical conformation as the native peptide LFB 17–31, except that the amide bonds point in opposite directions. The all-L-amino acid stereoisomer, Retro LFB 17–31, shows low antibacterial activity. The reason may be that all-D-amino acid peptides either interact more strongly with the chiral phospholipids of the bacterial cell membrane or that they are more resistant to proteases than their all-L-amino acid counterparts.

The activity of the peptides against *S. aureus* is not as high as observed for *E. coli*, indicating that the interactions of the peptides with the lipopolysaccharide layer of gram negative bacteria might be stronger than the interactions with the lipid cell membrane of gram positive bacteria.

The activity of the tryptophan-Pmc containing peptides do not show the same differences between all-D- and all-L-amino acid isomers as was observed for the peptides without the Pmc group. The effect of the tryptophan-Pmc residue seems to be more pronounced than the configurational effects found among the peptides without this residue, especially in the case of *S. aureus*. Most noticable is the tremendous increase in activity of the Retro-Pmc peptide. The activity of this peptide is increased eight times in the case of *E. coli* and more than ten times in the case of *S. aureus* just because of the tryptophan-Pmc residue.

The improvements observed upon Pmc modification in the case of *E. coli* is neglible, but the modification increases the activity against *S. aureus* about six times. The gram positive bacteria are obviously more vulnerable towards tryptophan-Pmc containing peptides than their non tryptophan-Pmc containing counterparts.

Antimicrobial Activity of Tryptophan Modified Human (LFH), Porcine (LFP) and Caprine (LFG) Lactoferricin The results from the alanine scan of bovine lactoferricin (LFB 17–31) showed that the two tryptophan residues in positions six and eight could not be substituted by alanine without a major loss of antibacterial activity. Examination of the similar sequence parts of native LFH, LFP and LFG lactoferricin shows that these peptides lack the tryptophan residue in position eight, but have during evolution conserved the tryptophan residue in position six. We have synthesized LFH, LFP and LFG analogs with a tryptophan residue substituted in the position eight to see if the antimicrobial activity of these peptides could be increased. The MIC values for the native sequences are given in Table 4, together with the tryptophan modified peptides.

H$_2$N-Thr-Lys-Cys-Phe-Gln-Trp-Gln-Trp-Asn-Met-Arg-Lys-Val-Arg-Gly-COOH

Sequence of modified human lactoferricin (LFHW8) Substituted tryptophan is high-lighted. (Arg-Trp)

H$_2$N-Ser-Lys-Cys-Tyr-Gln-Trp-Gln-Trp-Arg-Met-Arg-Lys-Leu-Gly-Ala-COOH

Sequence of modified caprine lactoferricin (LFGW8). Substituted tryptophan is high-lighted. (Arg-Trp)

H$_2$N-Glu-Lys-Cys-Leu-Arg-Trp-Gln-Trp-Glu-Met-Arg-Lys-Val-Gly-Gly-COOH

TABLE 4

MIC results for tryptophan modified human (LFHW8) and caprine (LFGW8) lactoferricin. (MIC values for native LFB 17–31 and native sequences of LFH and LFG are also listed for the sake of comparison.)

| Peptide | MIC *E. coli* | MIC *S. aureus* | % Hemolysis 10 µg/ml |
|---|---|---|---|
| LFHW8 | 110 | >1000 | 2.5 |
| LFPW8 | 500 | >1000 | 2.9 |
| LFGW8 Y13 | 110 | >1000 | NT |
| LFGW8 | 500 | >1000 | 2.7 |
| Native LFB 17–31 | 50 | 100 | 2.6 |
| Native LFH | >1000 | >1000 | NT |
| Native LFP | >1000 | >1000 | |
| Native LFG | 750 | N.T | 2.4 |

N.T = Not tested

Both LFHW8 and LFGW8 show improvements in activity against *E. coli* compared to the native sequences of the same peptides.

Antimicrobial Activity of LFH, LFP and LFG with a Tryptophan-Pmc Residue

During acidic cleavage of the peptide (either with or without the above modifications to the native sequence) from the resin and cleavage of acid labile protecting groups, a byproduct with a Pmc-group attached to one of the tryptophan residues was isolated and analysed for antibacterial activity. The results are shown in Table 5.

TABLE 5

MIC results for LFH, LFG and LFP with a Pmc group attached to one of the two tryptophan residues, for LFC Pmc and LFH Pmc, the PMC group will be attached to the only available tryptophan.

| Peptide | MIC *E. coli* | MIC *S. aureus* |
|---|---|---|
| LFG Pmc | 25 | 25 |
| LFH Pmc | 25 | 50 |
| LFHW8 Pmc | 25 | 20 |
| LFGW8 Pmc | 50 | 75 |
| LFPW8 Pmc | 20 | 50 |
| LFHW8 Y13Pmc | 25 | 20 |

As for all tryptophan-Pmc containing peptides analysed so far, these peptides generally show remarkable improvements in antibacterial activity against both *E. coli* and *S. aureus*.

Antimicrobial Activity of Tryptophan Rich Analogs of Bovine Lactoferricin (LFB 17–31)

The alanine scan showed that the two tryptophan residues in the sequence of bovine lactoferricin 17–31 were absolutely essential to the antibacterial activity of the peptide. Alanine substitution of any of these two residues led to a major loss of antibacterial activity. The alanine scan also showed that the nonessential amino acids in the sequence of bovine lactoferricin 17–31 were the three residues Cys(3), Gln(7) and Gly(14). Based on this knowledge we therefore synthesized a series of five tryptophan rich analogs of bovine lactoferricin 17–31 with one, two or three of the nonessential amino acids substituted by tryptophan. This technique of performing an alanine scan and then replacing seeming non-essential amino acids with Tryptophan or other bulky and/or lipophilic amino acids can be used to enhance the cytotoxicity of peptides generally, and is not limited to lactoferricin. The sequences of the tryptophan rich bovine lactoferricin analogs are shown below.

lowed by postfixation, dehydration and embedding in Epon Araldite according to standard procedures. Ultrathin sections were cut on a Reichert Ultracut S and then contrasted LFBW3:
$H_2N$-Phe-Lys-Trp-Arg-Arg-Trp-Gln-Trp-Arg-Met-Lys-Lys-Leu-Gly-Ala-COOH LFBW14:
$H_2N$-Phe-Lys-Cys-Arg-Arg-Trp-Gln-Trp-Arg-Met-Lys-Lys-Leu-Trp-Ala-COOH LFBW3, 14:
$H_2N$-Phe-Lys-Trp-Arg-Arg-Trp-Gln-Trp-Arg-Met-Lys-Lys-Leu-Trp-Ala-COOH LFBW3, 7, 14:
$H_2N$-Phe-Lys-Trp-Arg-Arg-Trp-Trp-Trp-Arg-Met-Lys-Lys-Leu-Trp-Ala-COOH LFBW4, 10:
$H_2N$-Phe-Lys-Cys-Trp-Arg-Trp-Gln-Trp-Arg-Trp-Lys-Lys-Leu-Gly-Ala-COOH

TABLE 6

MIC results for five tryptophan rich analogs of bovine lactoferricin (LFB 17–31) together with native LFB 17–31.

| Peptides | MIC E. coli | MIC S. aureus |
|---|---|---|
| LFB 17–31 | 50 | 100 |
| LFBW3 | 20 | 20 |
| LFBW14 | 20 | 25 |
| LFBW3, 14 | 10 | 10 |
| LFBW3, 7, 14 | 20 | 20 |
| LFBW4, 10 | 5 | 10 |

Substitution of nonessential amino acids in the sequence of LFB 17–31 by tryptophan residues improves the antibacterial activity of these peptides by at least two times that of the native sequence in the case of E. coli and by four times in the case of S. aureus.

Peptide W3714, with three additional tryptophan residues (a total of five tryptophan residues in the peptide), has decreased activity. This is probably more a result of a solubility problem, this peptide being less soluble in aquous solutions and therefore giving lower concentrations than calculated. This has been physically observed during MIC testing procedures when the peptide tended to precipitate at high concentrations.

EXAMPLE 4
Antitumoral Effects of Different Peptides

Cyclic LFB 17–41 was from Morinaga, Milk Industri, Japan

Cytotoxicity

Different murine and human tumor cells ($4 \times 10^6$) were applied in 96-well culture plates (Costar) in a volume of 0.1 ml RPMI 1640 medium. Peptide solutions (0.1 ml) were added and the plates incubated at 37° C. for 30 minutes, 4 hours or 24 hours. The cytotoxicity was measured using the MTT method (Mosmann et al., J. Immunol. (1986) 136, 2348–2357).

Electron Microscopy
Scanning Electron Microscopy (SEM)

For scanning electron microscopy, Meth A cells were cultivated in a 12 well culture plate and treated with different peptides as described above. Cells were fixed in McDowell's fixative postfixated in 1% $OsO_4$, dehydrated and critical point dried according to standard procedures. The cells were examined in a Jeol JSM-5300 Scanning microscope.

Transmission Electron Microscopy (TEM)

Meth A cells were harvested from 12 culture plates by aspiration and fixed in McDowell's fixative overnight, folin 5% Uranyl acetate and Reynold's lead citrate. Sections were examined in a Jeol LEM-1010 transmission electron microscope.

Experimental Animals

Specific pathogen-free CB6F1 (Balb/c×C57 BL/6) female mice of about 8 weeks of age were obtained from Charles River (Germany). The mice were kept on standard laboratory chow and water. Tumor bearing mice were serologically screened for viral (LDH, CMV) and mycoplasmic infection and in all cases tested negative.

Tumors

Meth A is a non-adhesive murine sarcoma cell line [Sveinbjørnsson et al, (1996) BBRC 223: 643–649] syngenic in Balb/c and was maintained in vitro in RPMI 1640 containing 2% Foetal calf serum. Cells in the growth phase were harvested and washed in fresh medium and injected subcutaneously into the abdominal region of the mice. Each mouse received a single inoculation of $5 \times 10^6$ viable tumor cells in RPMI 1640.

Figure 2:
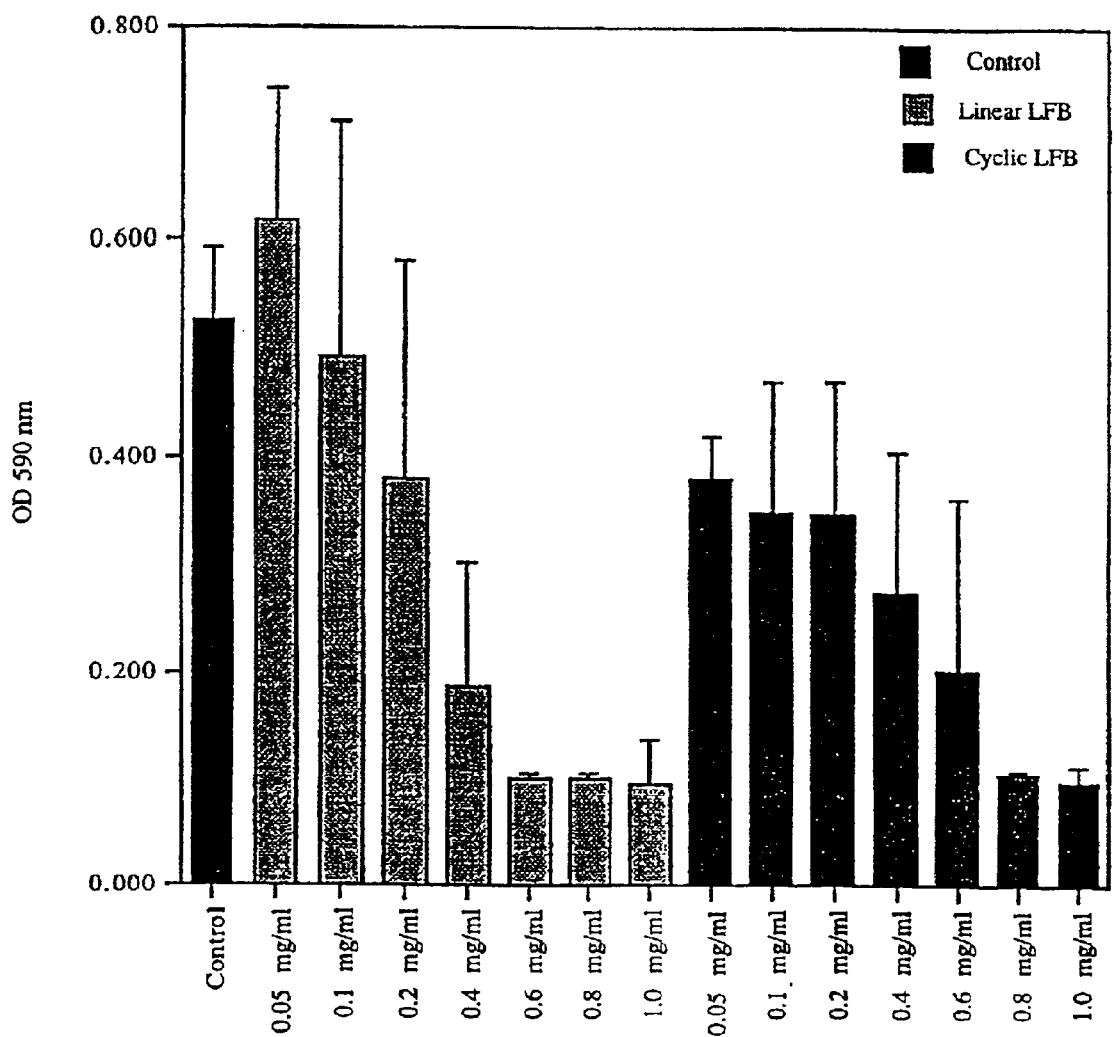
FIG. 2 shows the effects of linear and cyclic lactoferricin B on a Meth A fibrosarcoma cell line in vitro after 24 hours incubation.

Results
In Vitro
Cytotoxicity
Lactoferricin B Derivatives
A) Meth A
1. Cyclic and Linear LFB The cytotoxic effect of cyclic and linear LFB (17–41) on Meth A cells was studied. Linear LFB, with the cysteins protected with Acm, killed the Meth A cells ($1 \times 10^4$/ml) effectively at concentrations higher than 0.6 mg/ml after 4 h incubation (FIG. 2). Cyclic LFB, which is an enzymatically cleaved fragment of bovine lactoferrin effectively killed more than 99% of the cells at concentrations higher than 0.8 mg/ml.

2. LFB Derivatives

Figure 3:
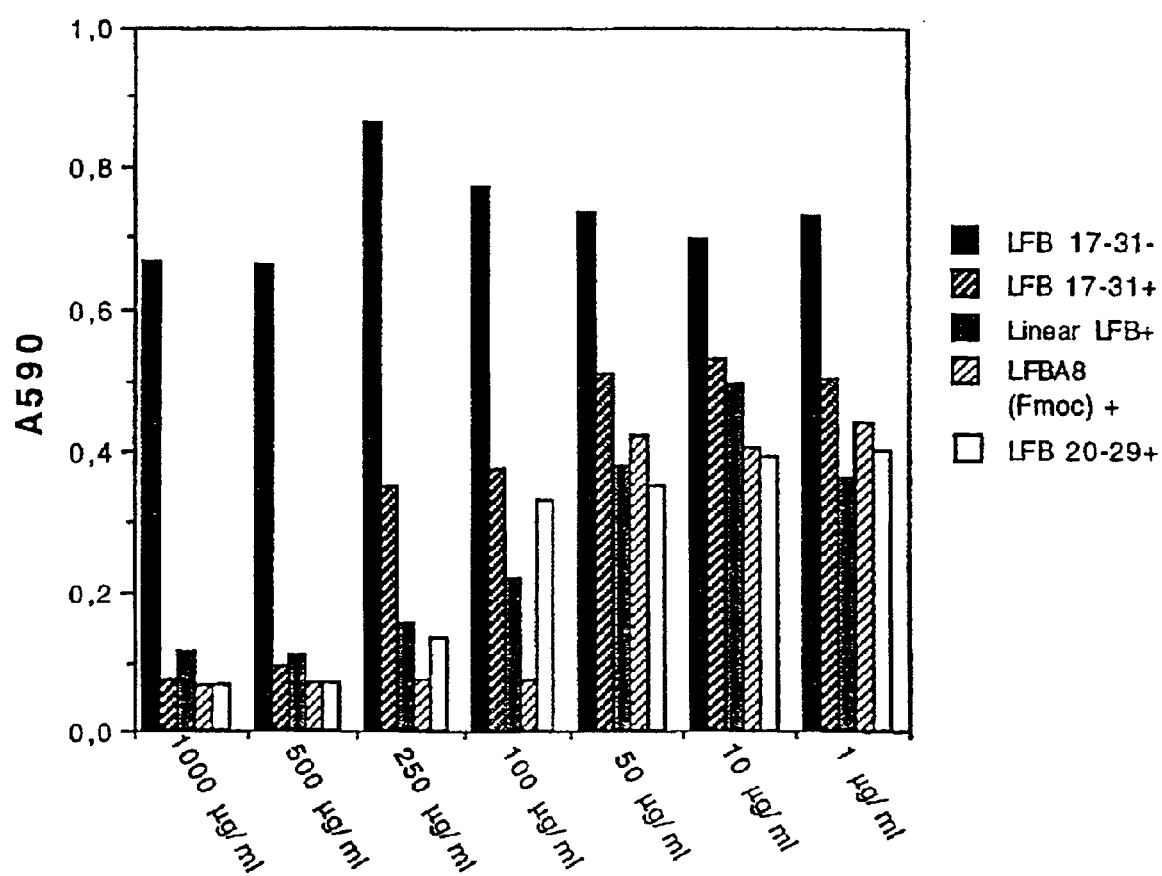
FIG. 3 shows the effects of different LFB derivatives on Meth A cells in vitro after ½ hour incubation, +=pmc-modified; −=unmodified.
Figure 4:
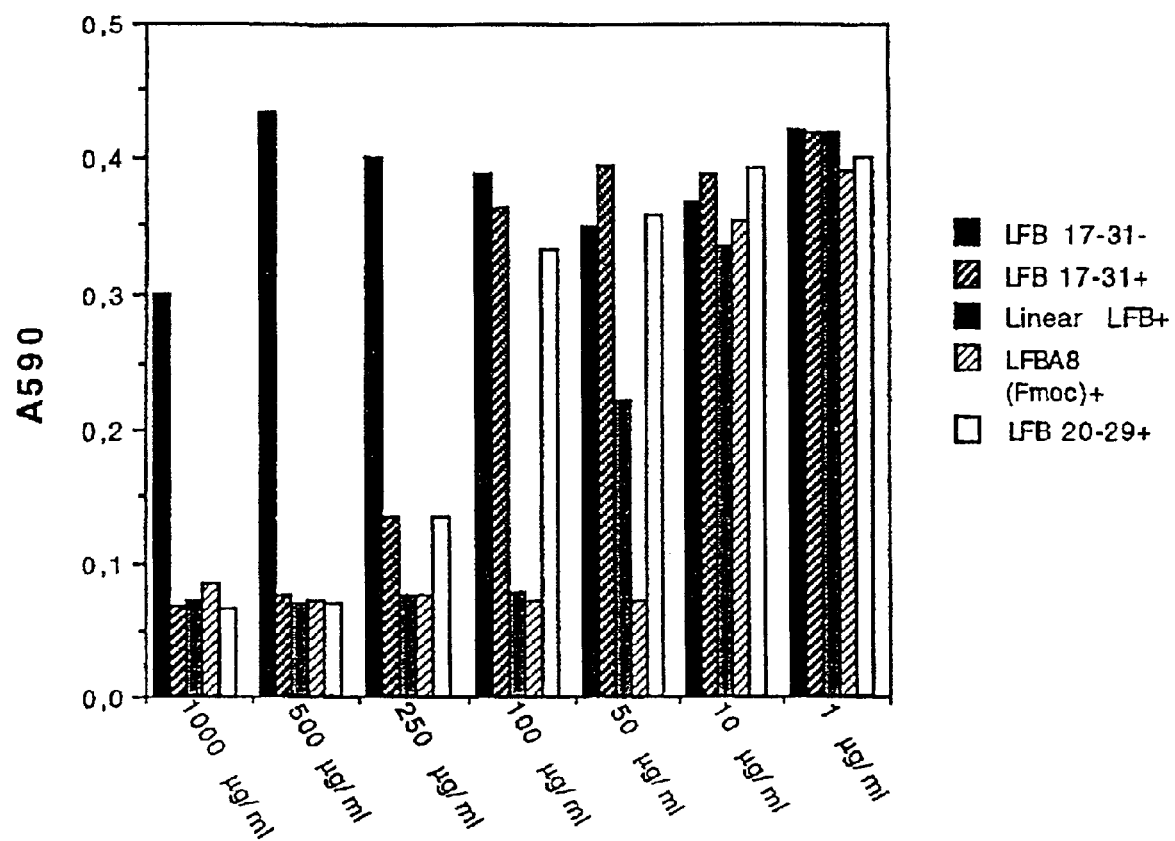
FIG. 4 shows the effects of different LFB derivatives on Meth A cells in vitro after 4 hours incubation, +=pmc-modified; −=unmodified.

LFB derivatives with different lengths and modifications were tested for their cytotoxic properties. Meth A cells were incubated with different concentrations of the different LFB derivatives, for ½ hour and 4 hours. As shown in FIG. 3, Unmodified LFB 17–31 had no significant cytotoxic effect on the Meth A cells at concentrations up to 1 mg/ml after ½ hour incubation. In this experiment it had a weak effect at 1 mg/ml after 4 hours incubation (FIG. 4). The PMC modified LFB 17–31 analoge killed the tumor cells at concentrations higher than 500 µg/ml after ½ hour incubation. The same concentration was needed to achieve effective killing after 4 hours. Linear LFB (17–41) modified with Pmc was slightly more effective than Pmc modified LFB 17–31.

In the figures "–" denotes no Pmc and "+" denotes with PMC modification.

A shorter sequence LFB 20–29 modified with PMC killed more than 90% of the cells at 250 µg/ml. An LFB 17–31 analogue (alanine substitution in position 8) that was modified with PMC and N-terminal Fmoc protected was effective at concentrations higher than 100 µg/ml after ½ hour and at 50 µg/ml after 4 hours. An Fmoc protected LFB peptide (Alanine substitution in position 8) killed most of the cells at 250 µg/ml at ½ hour and 4 hours (FIGS. 5 and 6). So it seems that a combination of Fmoc and Pmc modification enhanced the cytotoxic effect of LFB more than each of the two modifications alone. The retro LFB analog was also tested. The retro-Pmc-modified LFB 17–31 also possessed an enhanced cytotoxic effect compared to unmodified LFB 17–31 (FIGS. 5 and 6).

B) Human Promelocytic Leukemia Cell Line HL60.

The cytotoxic effect of LFB 17–41 (PB), LFB 14–31 (P1), LFB 14–31 Pmc (P2), LFB 17–31 (P3) and LFB 17–31 Pmc (P4) on human HL 60 cells was studied. LFB 14–31 and LFB 17–31 showed no cytotoxic effect at the concentration tested whereas LFB 17–41 possessed a weak concentration dependant cytotoxic effect. The LFB 17–31 Pmc peptide induced a markedly stronger effect (appr. 5 fold higher) than the other peptides tested. See FIG. 7.

3. EM Studies

The SEM and TEM results show that the cell membranes are strongly disrupted by lactoferricin peptides, resulting in effective release of intracellular material. The lysis seems to be very rapid, i.e. within minutes by the most effective peptides.

In Vivo

1. Tumor Regression

Murine Meth A Fibrosarcoma

After a single inoculation of 5×10$^7$ viable Meth A cells, different LF peptides were injected intratumorally (LFB-14–31, LFB 17–31 Pmc, 500 µg in a 50 µl dose; LFB 17–31, 1000 µg in a 50 µl dose), on day 7 and day 10. LFB 14–31 was also injected intraperitoneally (PBI), 500 µg/ml. Saline only was injected in the control mice (50 µl) (K1,K2,K3). The tumor diameter (mean of transversal and longitudinal) were measured with an electronic caliper.

The in Vivo Effect of LFB 17–31. LFB 17–31pmc and LFB on Murine MethA Fibrosarcoma As shown in FIG. 8, all three peptides tested, LFB 17–31 (PB), LFB 14–31 pmc (P2), LFB 14–31 (P1), induced regression of the Meth A tumors, after treatment on day 7 and 10. "Diam. mm." refers to diameter of the tumours.

Interestingly, tumors were also eradicated in the mice that were treated intraperitoneally with LFB 14–31 (PBI). Mice treated with saline only are represented as K1, K2 and K3.

EXAMPLE 2

Murine Melanoma B16F10

After a single inoculation of 5×10$^6$ viable B16F10 murine melanoma cells, D-LFB A7 Pmc-NH$_2$ was injected intratumorally in the tumors on day 10 and 12 (500 µg/injection in 50 µl saline). Saline only was injected in the control mice (50 µl). The tumor diameter (mean of transversal and longitudinal) were measured every second day with an electronic calliper.

The in Vivo Effect of D-LFB A7 Pmc-NH2 on Murine Melanoma B16F10

As shown in FIG. 9, D-LFB A7 Pmc-NH$_2$ (pep) was able to effectively induce regression of the solid tumors. The y axis represents the diameter of the tumour in mm. Three out of five were totally eradicated after only two injections. After six days after the first treatment, one of the tumor started to grow again, and 10 days after the first treatment a second tumors started to grow.

2. Adaptive Immunity

After successful treatment of established Meth A tumors, some mice were kept for one month before reinoculation of tumor cells as described above. In some of these mice a third inoculation of tumor cells were performed one month later than the second inoculation. No tumors were established in these mice and the mice were kept for a longer period without any effect on the normal condition of these mice.

EXAMPLE 5

The effect of chemical modification of a further moderately active peptide has also been investigated. The stating peptide is a fragment of bovine lactoferrin, which corresponds to residues 14–31 of the native sequence (see Table 1 in FIG. 1 for the full sequence). The antimicrobial activity in the form of MIC values against *E. coli* and *S. aureus*, the toxicity expressed as the concentration which caused 50% hemolysis (EC 50) and the anti-tumour activity in the form of the number of µg/ml of peptide required to kill 50% of MethA cells for the peptides are shown below in Table 7.

TABLE 7

| Peptide | MIC E. coli µg/ml | MIC S. aureus µg/ml | EC 50 (µM) | MethA IC 50 µM/ml |
|---|---|---|---|---|
| LFB 14–31 | 70 | >250 | >404 | no activity |
| LFB 14–31 PMC | 15 | 20 | 244 | 14.6 |
| LFB 14–31 A2, 6, 10, 17 | 20 | 2.5 | >440 | 165 |
| LFB 14–31 A2, 6, 10, 17 PMC | 20 | 2.5 | >165 | 12.8 |
| LFB 14–31 A2, 6, 10, 17R4 | 30 | 20 | >438 | 75.8 |
| LFB 14–31 A2, 6, 10, 17R4 PMC | 10 | 2.5 | 290 | 6.9 |
| LFB 14–31 A2, 6, 10, 17R4, 11 | | | >444 | 75.5 |
| LFB 14–31 A2, 6, 10, 17R4, 11 PMC | | | 327 | 5.2 |
| LFB 14–31 A2, 6, 10, 17F7R4 | 10 | 2.5 | >440 | 30.2 |
| LFB 14–31 A2, 6, 10, 17F7R4 PMC | 10 | 2.5 | 20 | 7.7 |
| LFB 14–31 A2, 6, 10, 17F7K16L14 | 10 | 10 | >440 | 28.1 |
| LFB 14–31 A2, 6, 10, 17F7K16L14 PMC | 10 | 2.5 | 89 | 5.2 |

As before, the presence of the bulky/lipophilic group PMC on one or more of the tryptophan residues enhances the antimicrobial and anti-tumour activity. Interestingly, the presence of this artificial bulky and lipophilic group is able to selectively enhance bacteriocidal activity, activity against *S. aureus* generally being more enhanced than against *E. coli*.

EXAMPLE 6

Table 8 shows anti-bacterial activity and toxicity data for LFB based peptides incorporating a non-genetic bulky and lipophilic amino in place of one of the amino acids in the native sequence. Further peptides also incorporate a group (PMC) which increases the bulk and lipophilicity of one of the naturally occurring tryptophan residues.

TABLE 8

| Peptide | MIC E. coli µg/ml | MIC S. aureus µg/ml | % Hemolysis 10 µg/ml | % Hemolysis 100 µg/ml |
|---|---|---|---|---|
| LFB | 50 | 100 | 2.6 | 3.47 |
| LFB Bip3 | 10 | 10 | | |
| LFB Bip6 | 25 | 25 | | |
| LFB Bip8 | 15 | 15 | | |
| LFB Bip6, 8 | 10 | 5 | | |
| LFB Bip3 PMC | 37.5 | 2.5 | | |
| LFB Bip8 PMC | 25 | 5 | | |
| LFB Tbt3 | 25 | 5 | | |
| LFB Tbt3 PMC | 37.5 | 10 | | |
| LFB Tbt6 | 12.5 | 10 | | |
| LFB Tbt6 PMC | 37.5 | 10 | | |
| LFB Tbt8 | 12.5 | 5 | | |
| LFB Tbt8 PMC | 25 | 5 | | |
| LFB Tbt6, 8 | 25 | 5 | | |
| LFB Nal6 | 20 | 75 | 2.2 | 4.4 |
| LFB Nal6 PMC | 25 | 20 | 2.8 | 17.8 |
| LFB Nal6, 8 | 10 | 20 | 2.8 | 4.9 |
| LFB Nal8 | 10 | 50 | 3 | 4.7 |
| LFB Nal8 PMC | 20 | 10 | 6.96 | 18.86 |
| LFB NPS-O6 | 20 | 100 | 2.8 | 4.1 |
| LFB NPS6 | 23 | 50 | 4.2 | 5.9 |

In the above table,
Bip = biphenylalanine
Tbt = tri-tert-butyltryptophan
Nal = 2-naphthylalanine
NPS = ortho-nitrophenylsulfinyl
NPS-O = ortho-nitrophenylsulfonyl
PMC = 2,2,5,7,8-pentamethylchroman-6-sulphonyl All peptides are LFB 17–31 and modifications thereof.

EXAMPLE 7

Experiments were performed to investigate the effect of PMC and varying peptide length on anti-tumour activity and toxicity (hemolytic activity)

The results of these experiments are presented in Table 9 below.

TABLE 9

| Peptide | Meth A IC$_{50}$ (µM) -PMC | Meth A IC$_{50}$ (µM) +PMC | RBC EC$_{50}$ (µM) -PMC | RBC EC$_{50}$ (µM) +PMC | Selectivity +PMC |
|---|---|---|---|---|---|
| LFB 14–31 A$_{2, 6, 10, 17}$ | 165 | 15 | >440 | 118 | 8 |
| LFB 14–30 A$_{2, 6, 10, 17}$ | >227 | 14 | >454 | 184 | 13 |
| LFB 14–29 A$_{2, 6, 10}$ | >235 | 18 | >469 | 367 | 20 |
| LFB 14–28 A$_{2, 6, 10}$ | >248 | 12 | >438 | >438 | >36 |

The presence of a PMC group on one or more of the tryptophan residues of an LFB peptide significantly increased its anti-tumour activity and to a lesser extent its hemolytic activity. Surprisingly it was found that by reducing the length of the peptide the selectivity, i.e. the anti-tumour verus the hemolytic activity of the peptide increased.

EXAMPLE 8

Methods for the Preparation of Peptide Esters
Transesterification from Resin

Fully protected peptide esters can be obtained by base catalysed transesterification from SASRIN™ and Merrifield-like resins. Good yields have been obtained with methanol and benzyl alcohol. The best results were obtained employing either KCN2, or LiBr/DBU as catalyst.
Standard Procedure for KCN-Catalysed Transesterification:

The peptide resin and the solvent employed have to be dried carefully before use, all have to withstand prolonged KCN-treatment. Transesterification will occur, even if the solubility of KCN is low; residual salt did not disturb. The peptide resin is suspended in a mixture of the desired alcohol and the cosolvent, e.g. dimethylacetamide, (usually 1:1, 10 ml/g resin). After 30 min sufficient solid KCN is added, so that a 0.08 M solution is obtained (or at least saturation). After stirring for 24 hours, the resin is filtered off and washed with the cosolvent. The catalyst must be destroyed immediately, e.g. by rigourously shaking the filtrate with sufficient solid anhydrous FeCl$_2$. Iron blue will flock out, it is left to settle for approx. 30 min and filtered off. The filtrate may remaine greenish. Further work-up depends on the solubility of the product, but it should be treated with water: After removing alcohol and cosolvent, the residue is taken up in an organic solvent, e.g. ethyl acetate or chloroform, for further aqueous extraction to remove salts.

Direct Benzyl Esterification Of N-Acylpeptides (p-Hydroxyphenyl)benzylmethylsulfonium derivatives (HOBMX) easily generate benzyl cations, which convertes N-terminal- and side chain-protected peptides into thier benzyl esters without racemization.

General Procedure: The petide and potassium carbonate are dissolved in dichloromethane, and the mixture is stirred at room temperature. After 10 min, HOBMCl is added to the solution and it is stirred for 8 hours. Inorganic salts in the reaction mixture are filtered off and the filtrate evaporated in vacuo. The residue is dissolved in toluene and washed with 0.5 M NaOH aqueous solution and then with water. The organic layer is dried over anhydrous sodium sulfate and the filtrate evaporated in vacuo.

EXAMPLE 9

A series of further modified peptides were prepared based on murine lactoferrin. In the following data (see Table 10), LFM refers to residues 17–31 of murine lactoferrin. Shorter peptides are indicated by the notation wherein e.g. LFM 17–24 represents an 8-mer peptide corresponding to the amino acids at positions 17 through to 24 of murine lactoferrin.

The murine equivalent of LFB is generally much less active than its bovine equivalent, however, by modifying the peptide in accordance with the present invention peptides with greatly enhanced anti-bacterial activity can be prepared. LFM does not possess a tryptophan residue at position 8, unlike its more active bovine counterpart. The inventors have identified this residue as important to the activity of LFB and thus this substitution of asparagine for tryptophan has been made.

This substitution alone did not significantly enhance the activity against the bacterial strains tested. Activity could be further enhanced by substituting one or both of the anionic residues at positions 1 and 9 with unchanged alanine or more preferably a cationic residue such as arginine.

By incorporating further bulky/lipophilic residues, e.g. a tyrosine residue at position 13 in place of the less bulky valine and/or by modifying the tryptophan residue by incorporation of the more bulky PMC group, peptides with good antimicrobial activity could be made.

In addition it was surprisingly found that shorter peptides based on fragments of LFM when modified to introduce additional bulky/lipophilic amino acids e.g. tryptophan or tyrosine and to increase the overall charge of the peptide by replacing native residues with cationic residues such as arginine were particularly effective.

TABLE 10

| Peptide | MIC E. coli µg/ml | MIC S. aureus µg/ml | % Hemolysis 10 µg/ml | % Hemolysis 100 µg/ml |
|---|---|---|---|---|
| LFM | >1000 | >1000 | 2.3 | 3.1 |
| LFM W8 | >1000 | 1000 | 2.6 | 4.8 |
| LFM W8 Y13 | >1000 | >1000 | | |
| LFM A1 W8 | 750 | >1000 | 2.4 | 3 |
| LFM A1 W8 Y13 | 500 | >1000 | | |
| LFM A9 W8 | >1000 | >1000 | 2.5 | 3.5 |
| LFM A9 W8 Y13 | >1000 | >1000 | | |
| LFM A1, 9 W8 | 200 | >1000 | 2.8 | 3.7 |
| LFM A1, 9 W8 Y13 | 150 | >1000 | | |
| LFM R1, W8 | 75 | 500 | 2.8 | 3.48 |
| LFM R1 W8 PMC | >200 | >200 | | |
| LFM R1 W8 Y13 | 50 | 50 | | |
| LFM R9 W8 | 500 | >1000 | 3.1 | 4.59 |
| LFM R9 W8 PMC | 20 | 50 | | |
| LFM R9 W8 Y13 | 150 | 1000 | | |
| LFM R1, 9 W8 | 25 | 75 | 3.69 | |
| LFM R1, 9 W8 PMC | 10 | 5 | | 4.9 |
| LFM R1, 9 W8 Y13 | 25 | 50 | | |
| LFM A1 R9 W8 Y13 | 50 | 200 | | |
| LFM 17–24 R1, 2, 8 W3, 7Y4NH2 | 5 | 2.5 | | |
| LFM 17–24 R1, 2, 8 W3, 7Y4NH2 PMC | 25 | 1–2.5 | | |
| LFM 18–24 R1, 7 W2, 3, 6Y5NH2 | 10 | 0.5–1 | | |
| LFM 17–25 A4R2, 8, 9W3, 7Y1NH2 | 10 | 5 | | |
| LFM 17–25 A4R2, 8, 9W3, 7Y1NH2 PMC | 20 | 2.5 | | |
| LFM 17–26 A7R2, 8, 9W3, 4, 10Y1NH2 | 10 | 2.5 | | |

EXAMPLE 10

Table 11 below illustrates the effect of further chemical modifications which provide peptides in accordance with the invention.

TABLE 11

| Peptide | MIC E. coli µg/ml | MIC S. aureus µg/ml | % Hemolysis 10 µg/ml | % Hemolysis 100 µg/ml | MethA IC$_{50}$ µg/ml |
|---|---|---|---|---|---|
| LFB | 50 | 100 | 2.6 | 3.47 | 500 |
| LFB PMC | 10 | 10 | 2.8 | 4.4 | 120 |
| LFB PMC6 | 10 | 10 | 3.4 | 6 | 148 |
| LFB PMC8 | 18 | 10 | 3.6 | 9.79 | 150 |
| LFB 18–31 | 80 | 200 | | | |
| LFB 18–31 PMC | 10 | 10 | | | |
| LFB 19–31 | 200 | >250 | | | |
| LFB 19–31 PMC | 10 | 15 | | | |
| LFB 20–28 A4 | >100 | >100 | 0 | 1.68 | 500 |
| LFB 20–28 A4 FMOC | | | | | 120 |
| LFB 20–28 A4 FMOC PMC | | | | | 35 |
| LFB 20–28 A4 PMC | 15 | | 3.9 | 12.6 | 110 |
| LFB 20–29 | 60 | >100 | 1.75 | 2.74 | 500 |
| LFB 20–29 FMOC | 5 | 10 | 10.3 | 28.2 | 140 |
| LFB 20–29 FMOC PMC | | | 22.5 | 60.2 | 50 |
| LFB 20–29 PMC | 10 | 10 | 5.6 | 18.9 | 160 |
| LFB 20–30 | 40 | >100 | 2.16 | 3.1 | |
| LFB 20–30 PMC | 15 | 10 | 5.54 | 15.8 | |
| LFB 20–31 | 100 | 200 | | | |
| LFB 20–31 PMC | 10 | 10 | | | |
| LFB A1 | 70 | >200 | | | |
| LFB A1 PMC | 8.75 | 10 | | | |
| LFB A2 | 80 | >200 | | | |
| LFB A2 PMC | 11.25 | 10 | | | |
| LFB A3 | 25 | 100 | | | 500 |
| LFB A3 PMC | 7.5 | 7.5 | 2 | 3.67 | 130 |
| LFB A4 | 7.0 | >200 | | | |
| LFB A4 PMC | 15 | 27.5 | | | |
| LFB A5 | 120 | >200 | | | |
| LFB A5 PMC | 10 | 50 | | | |
| LFB A6 | >200 | >200 | 2.78 | 3.27 | |
| LFB A6 PMC | 25 | 17.5 | | | |
| LFB A7 | 30 | 150 | | | 500 |
| LFB A7 PMC | 20 | 7.5 | 2.1 | 3.8 | 88 |
| LFB A8 | >200 | >200 | 2.8 | 3.45 | 500 |
| LFB A8 FMOC | 60 | 10 | 2.87 | 7.79 | |
| LFB A8 FMOC PMC | | | 6.75 | 45.4 | |
| LFB A8 PMC | 15 | 17.5 | | | 275 |
| LFB A9 | 55 | >200 | | | |
| LFB A9 PMC | 10 | 12.5 | | | |
| LFB A10 | 140 | >200 | | | |
| LFB A10 PMC | 20 | 22.5 | | | |
| LFB A11 | 70 | >200 | | | |
| LFB A11 PMC | 22.5 | 22.5 | | | |
| LFB A12 | 50 | >200 | | | |
| LFB A12 PMC | 20 | 20 | | | |
| LFB A13 | 50 | >200 | | | |
| LFB A13 PMC | 15 | 15 | | | |
| LFB A14 | 25 | 160 | | | 500 |
| LFB A14 PMC | 15 | 17.5 | | | 100 |

Unless otherwise indicated, LFB represents LFB 17–31.

EXAMPLE 11

Table 12 below illustrates the antibacterial activity as well as toxicity (% hemolysis) data and some anti-tumoural activity for further peptides according to the invention. LFB stands for LFB 17–31.

TABLE 12

| Peptide | MIC E. coli μg/ml | MIC S. aureus μg/ml | % Hemolysis 10 μg/ml | % Hemolysis 100 μg/ml | Meth A IC$_{50}$ μg/ml |
|---|---|---|---|---|---|
| LFB F4 | 20 | 200 | 2.4 | 3.2 | |
| LFB F4 PMC | 20 | 20 | | | |
| LFB F4K1 | 20 | 200 | | | |
| LFB F4K1 PMC | 10 | 10 | | | |
| LFB K1 | 60 | 100 | | | |
| LFB K1 PMC | 10 | 10 | | | |
| LFB W3 | 20 | 20 | 2.3 | 3.8 | |
| LFB W3 PMC | >50 | 10 | 3.55 | 17.35 | |
| LFB W3, 14 | 10 | 10 | 3.1 | 5.1 | |
| LFB W3, 14 PMC | 20 | 20 | | | |
| LFB W3, 7, 14 | 20 | 20 | 4.02 | 66.1 | |
| LFB W3, 7, 14 PMC | 30 | 20 | 18.1 | 85.9 | |
| LFB W4, 10 | 5 | 10 | 4.45 | 27.8 | 500 |
| LFB W4, 10 PMC | 20 | 20 | 2.27 | 14.2 | 110 |
| LFB W14 | 20 | 25 | 3 | 4.1 | |
| LFB W14 PMC | 25 | 10 | | | |

EXAMPLE 12

Antibacterial peptides which are active against bacterial strains which have been shown to demonstrate resistance to other antibiotics are potentially very useful peptides. Table 13 below gives the antibacterial activity and toxicity data for some preferred peptides of the invention. MRSA is methicillin resistant *S. aureus* and MRSE is methicillin resistant *S. epidermidis*.

In Table 13, LFB=LFB 17–31 unless otherwise indicated. The previously identified one and three letter codes are used and in addition, the following N-terminal modifying groups are represented:

Bz=benzyl, CHx=cyclohexyl, Ad=adamantyl

TABLE 13

| Peptide | MIC E. coli μg/ml | MIC E. coli μM | MIC S. aureus μg/ml | MIC S. aureus μM | MIC MRSA μg/ml | MIC MRSA μM | MIC MRSE μg/ml | MIC MRSE μM | EC 50 μg/ml | EC 50 μM |
|---|---|---|---|---|---|---|---|---|---|---|
| Bz LFB | | | | | | | | | | |
| Chx LFB | | | >20 | >9.2 | 2.5–5 | 1.1–2.3 | | | | |
| Ad LFB | | | 7.5–10 | 3.3–4.5 | 2.5–5 | 1.1–2.2 | | | | |
| LFB PMC 6 | 10.0 | 4.3 | 2.5 | 1.1 | 2.5 | 1.1 | | | >1000 | >429 |
| LFB A3 PMC | 7.5 | 3.4 | 5.0 | 2.2 | | | | | >1000 | >449 |
| LFB A7 PMC | 20.0 | 8.8 | 15.5–20 | 6.8–8.8 | ≧20 | ≧8.8 | 17.5 | 7.7 | >1000 | |
| LFB A3, 7 | | | >20 | >10.5 | 17.5–20 | 9.2–10.5 | 5.0 | 2.6 | >1000 | >525 |
| LFB A3, 7 PMC | | | 2.5 | 1.2 | 2.5 | 1.2 | 2.5 | 1.2 | >1000 | >461 |
| LFB W3, 14 | 10.0 | 4.5 | 2.5 | 1.1 | 2.5 | 1.1 | 2.5 | 1.1 | >1000 | >453 |
| LFB retro PMC | 10.0 | 4.3 | 5–7.5 | 2.1–3.2 | | | | | >1000 | >429 |
| LFB enantio PMC | 7.5 | 3.2 | 2.5–5 | 1.1–2.1 | 2.5–5 | 1.1–2.1 | 2.5 | 1.1 | >1000 | >429 |
| LFB 20–30 PMC | 15.0 | 8.3 | 10.0 | 5.5 | | | | | | |
| LFB 17–27 A3, 7 R2, 11 W4, 10 Y1 NH2 | 10.0 | 5.9 | 2.5 | 1.5 | 0.5–1 | 0.3–0.6 | 2.5 | 1.5 | 700 ± 300 | 400 ± 200 |
| LFB 17–27 A7 M3 R2, 11 W4, 10 Y1 NH2 | 10.0 | 5.7 | 0.5–1 | 0.3–0.6 | | | | | 510 ± 160 | 291 ± 91 |
| LFB 17–27 A3, 7 R2, 11 W4, 10 Y1 NH2 PMC | | | 1–2.5 | 0.5–1.3 | | | | | 43 ± 8 | 22 ± 4 |
| LFM 17–26 A7R2, 8, 9W3, 4, 10Y1NH2 | 10.0 | 6.2 | 1.0 | 0.6 | 2.5 | 1.5 | | | 880 ± 90 | 543 ± 56 |
| LFM 17–26 A7R2, 8, 9W3, 4, 10Y1NH2 PMC | 200.0 | 106.0 | 2.5 | 1.3 | 2.5 | 1.3 | | | 150 ± 90 | 79 ± 48 |
| LPB Bip 3 | 12.5 | 5.9 | 2.5–5 | 1.2–2.4 | 2.5 | 1.2 | | | | |
| LFB Bip 6, 8 | ≧12.5 | ≧5.8 | 3.0 | 1.4 | 2.5 | 1.2 | | | | |
| LFB Bip 3 PMC | ≦25 | ≦10.5 | 2.5 | 1.1 | 2.5–5 | 1.1–2.1 | | | | |
| LFB Bip 8 PMC | 15.0 | 6.3 | 2.5 | 1.1 | 2.5 | 1.1 | | | | |
| LFB Nal 6, 8 | 10.0 | 4.8 | 20.0 | 9.6 | 5.0 | 2.4 | | | >1000 | >479 |
| LFB Tbt6 | 12.5 | 5.6 | 2.5 | 1.1 | 1–2.5 | 0.4–1.1 | 2.5 | 1.1 | >1000 | >448 |
| LFB Tbt6 PMC | 37.5 | 15.0 | 2.5–5 | 1.0–2.0 | 5.0 | 2.0 | | | 410 ± 70 | 164 ± 28 |
| LFB Tbt8 | 12.5 | 5.6 | 2.5–5 | 1.1–2.2 | 0.5–2.5 | 0.2–1.1 | 2.5 | 1.1 | >1000 | >448 |
| LFB Tbt8 PMC | 25–50 | 10–23 | 2.5–7.5 | 1.0–3.0 | 5.0 | 2.0 | | | 290 ± 70 | 116 ± 28 |
| LFB Tbt6, 8 | 25–37.5 | 12–18 | 2.5 | 1.2 | 5.0 | 2.3 | 2.5 | 1.2 | 230 ± 30 | 107 ± 14 |
| LFB Tbt3 | 25.0 | 11.1 | 2.5 | 1.1 | 2.5 | 1.1 | | | 500 ± 40 | 223 ± 18 |

EXAMPLE 13

Table 14 below gives MIC values for a variety of peptides according to the invention which incorporate a proportion of D amino acids.

| Peptide | Sequence* | MIC µg/ml E. coli | MIC µg/ml S. aureus | MIC µg/ml MRSA |
|---|---|---|---|---|
| LFM 17–27 A7R2, 8, 9W3, 4, 10Y 1 NH2 | TYR-ARG-ALA-TRP-ARG-TRP-ALA-TRP-ARG-TRP-ARG-CONH2 | 10 | 2.5 | |
| | tyr-ARG-ala-TRP-arg-TRP-ala-TRP-arg-TRP-arg-CONH2 | 7.5 | 7.5 | 2.5 |
| | tyr-arg-ala-TRP-ARG-TRP-ala-TRP-ARG-TRP-ARG-CONH2 | 7.5 | 5 | 2.5 |
| LFM 18–24 R1, 7W2, 3, 6Y5 NH2 | ARG-TRP-TRP-ARG-TYR-TRP-ARG-CONH2 | 10 | 1 | |
| | arg-TRP-trp-ARG-tyr-TRP-arg-CONH2 | 7.5 | 5 | 2.5 |
| | arg-trp-TRP-ARG-TYR-trp-arg-CONH2 | 7.5 | 5 | 2.5 |

*Upper case letters represents L-amino acids, lower case letters denote D-amino acids

EXAMPLE 14
Cytotoxicity of the Peptides of the Invention

The cytotoxic effect of the peptides on different murine and human tumor cells were measured using the MTT method (Mosmann et al., J. Immunol. (1986) 136, 2348–2357). MTT is a soluble tetrazolium salt yielding a yellow solution when prepared in media or salt solutions lacking phenol red. Dissolved MTT is converted to an insoluble purple formazan by cleavage of the tetrazolium ring by dehydrogenase enzymes. This water insoluble formazan can be solubilized using isopropanol or other solvents and the dissolved material is measured spectrophotometrically. The absorbance was measured as a function of concentration of converted dye.

The conversion of the soluble dye to the insoluble purple formazan is utilized in assays for measurement of cell proliferation. Active mitochondrial dehydrogenases of living cells cause this change, while dead cells do not.

We used this assay to measure the degree of cell death caused by peptides.

Cells:

Cells were maintained in RPMI-1641 medium containing 10% FBS, 1% L-glutamine and 0.1% penicillin and streptomycin. Cells to be used in the assay were grown to confluency, trypsinated and split to single cell suspension, counted and centrifuged at 1500 rpm for 10 min. The cell pellet was resuspended to a concentration of 4×105 cells/ml in RPMI-1640 without FBS and L-glutamine (assay-medium). 100 ml of cell suspension was transferred to each well on a 96-well microtiter plate. The cells were stimulated by adding 100 ml of various concentrations of peptides diluted with assay medium to each well. The final concentrations of peptide were for example: 5, 10, 20, 40, 60, 80, 100, and 200 mg/ml. Because there is a twofold dilution upon adding the peptide solution to the wells containing the cell suspension, the peptide solution had to be made twofold concentrated. As a negative control only medium was added to the cells, and as a positive control (100% killing) 1% triton X-100 was added. Following an incubation period of 4 h., 20 ml MTT dissolved in PBS at a concentration of 5 mg/ml was added to each well, and the plate was incubated further for 2 h. 130 ml of the supernatant were then removed and 100 ml acid alcohol (0.04–0.1 N HCl in isopropanol) added to each well to dissolve the dark blue crystals. The plate was placed on a shaker for 1 h and read spectrophotometrically at 590 nm in a microtiterplate reader using the Softmaxâ program.

Hemolytic Assay

The hemolytic activities of the peptides were determined using fresh human red blood cells. 8 ml blood was taken from a healthy person. 4 ml blood was transferred to a polycarbonate tube containing heparin to a final concentration of 10 U/ml, and the remaining 4 ml blood was transferred to a glass tube containing EDTA with final concentration of 15% EDTA. The erythrocytes were isolated from heparin-treated blood by centrifugation in 1500 rpm for 10 min and washed three times with phosphate-buffered saline (PBS) to remove plasma and buffy coat. The cell pellet was resuspended in PBS to make the final volume of 4 ml. The peptide was diluted to a concentration of 2 mg/ml and 0.1 mg/ml. The peptide was further diluted to the concentrations as stated in Table 15. For each tube PBS was added first, then RBCs and peptide solutions. The hematocrit in the blood treated with EDTA was determined after 30 min with Sysmex K-1000, and the resuspended RBCs were diluted into 10% hematocrit. RBCs in PBS (1%) with and without peptides (Table 15) were incubated in a shaker at 370 for 1 hour and then centrifuged at 4000 rpm for 5 min. The supernatant were carefully transferred to new polycarbonate tubes and the absorbance of the supernatant was measured at 540 nm. Baseline hemolysis was hemoglobin released in the presence of PBS, and 100% hemolysis was hemoglobin released in the presence of 0.1% Triton X-100.

TABLE 15

| Tube No. | Final peptide concentration (μg/ml) | Peptide or Triton X-100 (μl) | Red blood cells (μl) | PBS (μl) | Total Volume (μl) |
|---|---|---|---|---|---|
| 1 (2 mg/ml peptide) | Neg. control | | 70 | 630 | 700 |
| 2 (2 mg/ml peptide) | Pos. control | 7 | 70 | 623 | 700 |
| 3 (2 mg/ml peptide) | 1000 | 250 | 50 | 200 | 500 |
| 4 (2 mg/ml peptide) | 500 | 125 | 50 | 325 | 500 |
| 5 (2 mg/ml peptide) | 100 | 35 | 70 | 595 | 700 |
| 6 (2 mg/ml peptide) | 50 | 17.5 | 70 | 612.5 | 700 |
| 7 (0.1 mg/ml peptide) | 10 | 70 | 70 | 560 | 700 |
| 8 (0.1 mg/ml peptide) | 1 | 7 | 70 | 623 | 700 |

EXAMPLE 15
Solid Phase Peptide Synthesis

Initially the lactoferricin B used was a gift from Wayne Bellamy (NutritiOnal Science Laboratory, Morinaga Milk industry Co. Ltd, Japan). All the other peptides were synthesized on a 9050 Millipore Automatic Peptide Synthesizer. Generally, in solid phase synthesis, peptide chains are assembled from the carboxy teminus to the amino acid terminus. The first (C-terminal) amino acid was covalently attached to an insoluble support (the resin) by a linker (4-hydroxymethyl-phenoxyacetic acid). The remaining amino acids were added, one by one, until the peptide sequence was completed.

Using the Fmoc method, the a-amino end of the amino acid was temporary protected by the base labile 9-fluorenylmethoxycarbonyl (Fmoc) group. Not only the α-amino group of the amino acid was protected. Some of the amino acids have reactive side chains which are necessary to protect during the synthesis to prevent side reactions. These protecting groups, except for cysteine, were acid labile and cleaved upon treatment with TEA (trifluoroacetic acid) and scavengers (see below).

Prior to the synthesis, to the solid support PEG-PS (Poly Ethylene Glycol-Poly Styrene resin) was added a small volume of DMF (dimethylformamide) and left to swell for 30 minutes. Packed into a column, the Fmoc group was removed by treatment with a 20% piperidine solution in DMF. The incomming protected amino acid was now able to bind to the free amino end of the resin-linked amino acid with its carboxy end. However, coupling or acylation does not occur spontanously, the carboxylate must be activated., This was achieved by the use of preactivated amino acids, such as pentafluorophenyl (Pfp) esters, or amino acids with free carboxylates able to react with the coupling reagent HATU (O-(7-azabenzotriazol-1-yl)-1,1,3,3-tetramethyl-uronium hexafluoro-phosphate) in situ. Using Pfp esters, 1.3 eq. of HOBt (1-hydroxy-benzotriazole) was added to catalyse the reaction, while when using the coupling reagent HATU, the reaction was base catalysed with 2.4 eq. of DIPEA (diisopropylethylamine). A four-fold excess of activated amino acids was generally employed. The amino acids were dissolved in the activator solution in sufficient quantity, as calculated by the Express-Peptide program.

Amino acids were then delivered to the support-bound amino acid/peptide with fully deprotected α-amine group, and recycled through the loop mixed to achieve peptide bond formation. The capacity of the resins used scaled from 0.15 to 0.23 mmol/g, meaning available binding sites for the incomming amino acids, wherefrom the amount of activator eqvivalents was calculated. The standard coupling cycle for amino acids was 30 minutes, with the exception of arginine, isoleucine, threonine, tyrosine, valine, and the amino acids coupled thereafter, requiring 60 minutes. Extended coupling times for these amino acids were chosen because of their large side chains which are known to cause sterical hindrance during the coupling reaction. Once coupling was complete, the excess amino acid solution and reaction by-products were removed by washing with DMF. The next cycle begun with deblocking of the α-amino group of the N-teminal amino acid. The process of α-amino group deblocking followed by coupling was repeated for as many cycles as necessary to assemble the desired peptide.

After the synthesis was complete, the column material was transferred to a funnel and washed with methanol (3×) and dichloromethane (2×). The cleavage of the acid labile side chain protecting groups and cleavage of the peptides from the solid support was achieved using a mixture of 2% anisol, 2% ethandithiol, 2% water and 2% phenol in TFA, and with cleavage times of no more than four hours. The solid support was then removed by filtration, the filtrate concentrated under a high vacuum and the peptide precipitated in diethyl ether. The ether solution containing TFA was removed using a pasteur pipette, and the peptide was washed several times with diethyl ether and dried under a high vacuum.

Amino Acid Derivatives:

Fmoc-L-Ala-OPfp
Fmoc-L-Arg(Pmc)-OPfp
Fmoc-L-Cys(Acm)-OPfp
Fmoc-L-Gln-OPfp
Fmoc-L-Glu(OtBu)-OPfp
Fmoc-L-Gly-OPfp
Fmoc-L-Ile-OPfp
Fmoc-L-Leu-OPfp
Fmoc-L-Lys(tBoc)-OPfp
Fmoc-L-Met-OPfp
Fmoc-L-Phe-OPfp
Fmoc-L-Ser(tBu)-OPfp
Fmoc-L-Trp-OPfp
Fmoc-L-Tyr(tBu)-OPfp
Fmoc-L-Val-OPfp Amino Acid Derivatives:

Amino acid derivatives were purchased from either Bachem, MilliGen/Biosearch (Division of Millipore) or PerSeptive Biosystems. Phenol was purchased from Fluka, and anisole was purchased from Sigma. DMF, PIP, DIPEA TFA and PEG-PS resin were all purchased from PerSeptive Biosystems.

EXAMPLE 16

Table 16 below shows the anti-tumour activity and toxic data for a LFB 14–31 derivative incorporating either of two non-genetic bulky and lipohilic amino acids in place of a Trp or incorporating a group (Pmc) which increases the bulk and lipophilicity of one of the naturally occuring Trp or Phe residues.

TABLE 16

| Variable Peptide | RBC EC$_{50}$ ($\mu$M) | Meth A EC$_{50}$ ($\mu$M) |
| --- | --- | --- |
| LFB1431A2, 6, 10, 17 | >440 | 165 |
| LFB1431A2, 6, 10, 17Bip4 | 336 | 23.4 |
| LFB1431A2, 6, 10, 17Pmc | 165 | 12.8 |
| LFB1431A2, 6, 10, 17Tbt9 | 25.6 | 9.5 |

The presence of either of the three non-genetically modifications on a LFB 14–31 derivative significantly increased its anti-tumor activity. The Tbt modified peptide however possesed the highest hemolytic activity among the three modified analogs tested.

EXAMPLE 17

Table 17 below shows the anti-bacterial and anti-tumoural activity and toxicity of further peptides according to the invention. In particular, the substitutions show how replacement of non-essential tryptophan residues may result in peptides with advantageously low toxicity (activity against red blood cells and normal fibroblasts).

TABLE 17

| Substituion | Peptide | Meth A IC$_{50}$ ($\mu$M) (4 h) | Mic E-coli ($\mu$M) | Mic S. Aureus ($\mu$M) | RBC EC$_{50}$ ($\mu$M) | Fibroblast IC$_{50}$ ($\mu$M) |
| --- | --- | --- | --- | --- | --- | --- |
|  | LFB 14–31A$_{2, 6, 10, 17}$F$_7$K$_{16}$L$_{14}$R$_4$ | 6.6 | 2/4 | 2 | 110 | 17 |
| Alanine |  |  |  |  |  |  |
| W3 → A3 | LFB 14–31A$_{2, 3, 6, 10, 17}$F$_7$K$_{16}$L$_{14}$R$_4$ | 24.1 | 15 | 10 | >463 | 190 |
| W9 → A9 | LFB 14–31A$_{2, 6, 9, 10, 17}$F$_7$K$_{16}$L$_{14}$R$_4$ | 16.2 | 10 | 5 | 382 | 46.3 |
| W11 → A11 | LFB 14–31A$_{2, 6, 10, 11, 17}$F$_7$K$_{16}$L$_{14}$R$_4$ | 11.1 | 10 | >2.5 | 278 | 46.3 |
| W9, 11 → A9, 11 | LFB 14–31A$_{2, 6, 9, 10, 11, 17}$F$_7$K$_{16}$L$_{14}$R$_4$ | 110.1 | 30 | 30 | >489 | >489 |
| Lysine |  |  |  |  |  |  |
| W3 → K3 | LFB 14–31A$_{2, 6, 10, 17}$F$_7$K$_{3, 16}$L$_{14}$R$_4$ | 230 |  |  | >451 | 230 |
| W9 → K9 | LFB 14–31A$_{2, 6, 10, 17}$F$_7$K$_{9, 16}$L$_{14}$R$_4$ | 13.5 | 30 | 10 | >451 | 58.7 |
| W11 → K11 | LFB 14–31A$_{2, 6, 10, 17}$F$_7$K$_{11, 16}$L$_{14}$R$_4$ | 7.9 | 5 | <2.5 | >451 | 30.7 |
| W9, 11 → K9, 11 | LFB 14–31A$_{2, 6, 10, 17}$F$_7$K$_{9, 11, 16}$L$_{14}$R$_4$ | >300 |  |  | >463 | >463 |
| Isoleucine |  |  |  |  |  |  |
| W3 → I3 | LFB 14–31A$_{2, 6, 10, 17}$F$_7$I$_3$K$_{16}$L$_{14}$R$_4$ | 9 | 2/4 | 2/4 | 323 | 20 |
| W9 → I9 | LFB 14–31A$_{2, 6, 10, 17}$F$_7$I$_9$K$_{16}$L$_{14}$R$_4$ | 12 | 5 | <1 |  | 26 |
| W11 → I11 | LFB 14–31A$_{2, 6, 10, 17}$F$_7$I$_{11}$K$_{16}$L$_{14}$R$_4$ | 6 | 2/5 | <1 |  | 15 |
| W9, 11 → I9, 11 | LFB 14–31A$_{2, 6, 10, 17}$F$_7$I$_{9, 11}$K$_{16}$L$_{14}$R$_4$ | 22 |  |  |  | 26 |
| W3, 9 → I3, 9 | LFB 14–31A$_{2, 6, 10, 17}$F$_7$I$_{3, 9}$K$_{16}$L$_{14}$R$_4$ | 36 | 5 | 5 | >470 | 108 |
| W3, 11 → I3, 11 | LFB 14–31A$_{2, 6, 10, 17}$F$_7$I$_{3, 11}$K$_{16}$L$_{14}$R$_4$ | 16 | 2.5 | 5 | 413 | 45 |
| W3, 9, 11 → I3, 9, 11 | LFB 14–31A$_{2, 6, 10, 17}$F$_7$I$_{3, 9, 11}$K$_{16}$L$_{14}$R$_4$ | 47 | 2.5 | 10 | >487 | 280 |
| F7 → A7 | LFB 14–31A$_{2, 6, 10, 17}$F$_7$K$_{16}$L$_{14}$R$_4$ | 34.6 | 15 | 10 | >455 | 288.9 |

What is claimed is:

1. A modified lactoferrin peptide which is cytotoxic, 7 to 18 amino acids in length, with three or more cationic residues and which has one or more extra bulky and lipophilic amino acids as compared to the native lactoferrin sequence, wherein the extra bulky or lipophilic amino acid is a non-genetic amino acid, trytophan or phenylalanine, as well as esters, amides, salts and cyclic derivatives thereof, wherein the extra bulky and lipophilic amino acid comprises a bulky and lipophilic R group having 7 or more non-hydrogen atoms.

2. A peptide as claimed in claim 1 wherein the non-genetic amino acid is selected from biphenylalanine, tri-tert-butyltryptophan, 2-naphtylalanine, ortho-nitrophenylsulfinyl-tryptophan, ortho-nitrophenylsulfonyl-tryptophan and adamantylalanine.

3. A peptide as claimed in claim 1 wherein the non-genetic amino acid is a standard genetic amino acid whose R group has been modified.

4. A peptide as claimed in claim 3 wherein the R group is modified by a protecting group.

5. A peptide as claimed in claim 4 wherein the protecting group is selected from the group consisting of Pmc, Pbf, tert-buyl and carboxybenzyl.

6. A modified lactoferrin peptide which is cytotoxic, 7 to 18 amino acids in length, with three or more cationic residues and which has one or more extra bulky and lipophilic amino acids as compared to the native lactoferrin sequence, as well as esters, amides, salts and cyclic derivatives thereof, wherein the extra bulky and lipophilic amino acid comprises a bulky and lipophilic N-terminal group which is a cyclic group comprising at least 5 non-hydrogen atoms.

7. A peptide as claimed in claim 6 wherein the N-terminal group comprises 2 or more fused rings.

8. A modified lactoferrin peptide which is cytotoxic, 7 to 18 amino acids in length, with three or more cationic residues and which has one or more extra bulky and lipophilic amino acids as compared to the native lactoferrin sequence, as well as esters, amides, salts and cyclic derivatives thereof, wherein the extra bulky and lipophilic amino acid comprises a bulky and lipophilic C-terminal group which comprises at least 4 non-hydrogen atoms.

9. A pharmaceutical composition comprising a peptide as claimed in claim 1 together with a physiologically acceptable diluent, carrier or excipient.

10. A method of treating bacterial infections in a patient comprising the administration to said patient of one or more of the peptides claimed in claim 1.

11. A method of treating tumours in a patient comprising the administration to said patient of one or more modified lactoferrin peptides which are cytotoxic, 7 to 25 amino acids in length, with three or more cationic residues and which have one or more extra bulky and lipophilic amino acids as compared to the native lactoferrin sequence, as well as esters, amides, salts and cyclic derivatives thereof, wherein the extra bulky and lipophilic amino acid comprises a bulky and lipophilic R group having 7 or more non-hydrogen atoms but excluding the peptide LFB (17–41) wherein the cysteine residues are pyridylethylated.

12. A method of inhibiting the growth of bacteria comprising contacting the bacteria with an inhibiting effective amount of a peptide as claimed in claim 1.

13. A method of enhancing the cytotoxicity or selectivity of a 7 to 18 mer lactoferrin originating peptide with three or more cationic residues by incorporating therein an extra bulky and lipophilic amino acid as defined in claims 1.

14. The enantio or retro-enantio form of LFB and peptide fragments thereof.

15. A peptide as claimed in claim 1 wherein the peptide is 15 or fewer amino acids in length.

16. A peptide as claimed in claim 6 wherein the peptide is 15 or fewer amino acids in length.

17. A peptide as claimed in claim 8 wherein the peptide is 15 or few amino acids in length.

18. A method of treating tumors in a patient comprising the administration to said patient of one or more modified lactoferrin peptides which are cytotoxic, 7 to 25 amino acids in length, with three or more cationic residues and which have one or more extra bulky and lipophilic amino acids as compared to the native lactoferrin sequence, as well as esters, amides salts and cyclic derivatives thereof, wherein the extra bulky and lipophilic amino acid comprises a bulky and lipophilic N-terminal group which is a cyclic group comprising at least 5 non-hydrogen atoms.

19. A method of treating tumors in a patient comprising the administration to said patient of one or more modified lactoferrin peptides which are cytotoxic, 7 to 25 amino acids in length, with three or more cationic residues and which have one or more extra bulky and lipophilic amino acids as compared to the native lactoferrin sequence, as well as esters, amides, salts and cyclic derivatives thereof, wherein the extra bulky and lipophilic amino acid comprises a bulky and lipophilic C-terminal group which comprises at least 4 non-hydrogen atoms.

20. A method of causing regression of a solid tumor in a patient comprising the administration to said patient of lactoferrin B or a fragment thereof that causes tumor regression.

21. The method of claim 20 wherein sad lactoferrin B or said fragment is cyclic.

* * * * *